US 8,962,801 B2

(12) United States Patent
Jennings et al.

(10) Patent No.: US 8,962,801 B2
(45) Date of Patent: Feb. 24, 2015

(54) *NEISSERIA* PORIN PROTEINS

(75) Inventors: Michael Paul Jennings, Manly (AU); Ian Richard Anselm Peak, Upper Coomera (AU)

(73) Assignee: Griffith University, Nathan, Queensland (AU)

( * ) Notice: Subject to any disclaimer, the term of this patent is extended or adjusted under 35 U.S.C. 154(b) by 0 days.

(21) Appl. No.: 13/812,872

(22) PCT Filed: Aug. 1, 2011

(86) PCT No.: PCT/AU2011/000971
§ 371 (c)(1),
(2), (4) Date: Mar. 13, 2013

(87) PCT Pub. No.: WO2012/012851
PCT Pub. Date: Feb. 2, 2012

(65) Prior Publication Data
US 2013/0196901 A1 Aug. 1, 2013

(30) Foreign Application Priority Data
Jul. 30, 2010 (AU) ................................ 2010903418

(51) Int. Cl.
*C07K 14/22* (2006.01)
*A61K 38/16* (2006.01)
*A61P 31/04* (2006.01)
*C07K 16/12* (2006.01)
*A61K 39/095* (2006.01)

(52) U.S. Cl.
CPC .............. *C07K 14/22* (2013.01); *C07K 16/1217* (2013.01); *A61K 39/095* (2013.01); *C07K 2317/33* (2013.01)
USPC ........................................... 530/350; 514/2.8

(58) Field of Classification Search
CPC ............... C07K 14/22; C07K 2317/33; C07K 16/1217; A61K 39/095
See application file for complete search history.

(56) References Cited

U.S. PATENT DOCUMENTS 7,118,757 B1    10/2006  Seid, Jr. et al.
2007/0231342 A1 10/2007  Giuliani et al.

FOREIGN PATENT DOCUMENTS

| WO | WO 2004/065603 A2 | 8/2004 |
| WO | WO 2005/117956 A2 | 12/2005 |
| WO | WO 2009/144462 A2 | 12/2009 |
| WO | WO 2011/125015 A2 | 10/2011 |

OTHER PUBLICATIONS

Van Der Voort et al, Specificity of Human Bactericidal Antibodies against PorA P1.7,16 Induced with a Hexavalent Meningococcal Outer Membrane Vesicle Vaccine, Infection and Immunity, 1996, 64, pp. 2745-2751.*
PorA sequence of H44/76 strain, from http://www.uniprot.org/uniprot/E6MXW0, pp. 1-5, accessed Mar. 3, 2014.*
Van Der Ley et al, Use of Transformation to Construct Antigenic Hybrids of the Class 1 Outer Membrane Protein in *Neisseria meningitidis*, Infection and Immunity, 1993, 61, pp. 4217-4224.*
PorA sequence of 2996 strain, from http://www.ncbi.nlm.nih.gov/protein/CAA42699.1, pp. 1-2, accessed Mar. 3, 2014.*
Vicente, D. et al "Prevalence of genosubtypes (PorA types) of serogroup B invasive meningococcus . . . " J. of Med. Microbiol. 54(4): 381-384 (Apr. 2005).
Van Der Ley, P. et al "Construction of porA Mutants." Methods in Molecular Medicine, Meningococcal Vaccines. 66:145-154 (2001).
Suker et al., "The porA gene in serogroup A meningococci: evolutionary stability and mechanism of genetic variation" Mol. Microbiol. 12(2):253-65 (1994).
Suker et al., "The porA gene in serogroup A meningococci: evolutionary stability and mechanism of genetic variation" UNIPROT Database Accession No. Q51249 (1994).
Sorhouet Pereira et al., PorA types in *Neisseria meningitidis* serogroup B isolated in Argentina from 2001 to 2003: . . . , J. Med. Microbiol. 57(Pt3):338-42 (2008).

* cited by examiner

*Primary Examiner* — Julie Ha
*Assistant Examiner* — Li Ni Komatsu
(74) *Attorney, Agent, or Firm* — Womble Carlyle Sandridge & Rice, LLP

(57) ABSTRACT

*Neisseria meningitidis* PorA constructs are provided which have one or more disrupted variable regions created by insertion of entire conserved regions or conserved region amino acids. The highly immunogenic variable regions of PorA are responsible for eliciting strain-specific immune responses that are not broadly protective, so disruption of the variable regions directs the immune response against conserved region epitopes to effectively immunize against a broader spectrum of *N. meningitidis* strains. Also provided are encoding nucleic acids, genetic constructs, host cells expressing the PorA constructs and compositions, kits and methods for detection and treatment of *Neisseria meningitidis* infections.

17 Claims, 22 Drawing Sheets

Figure 4:
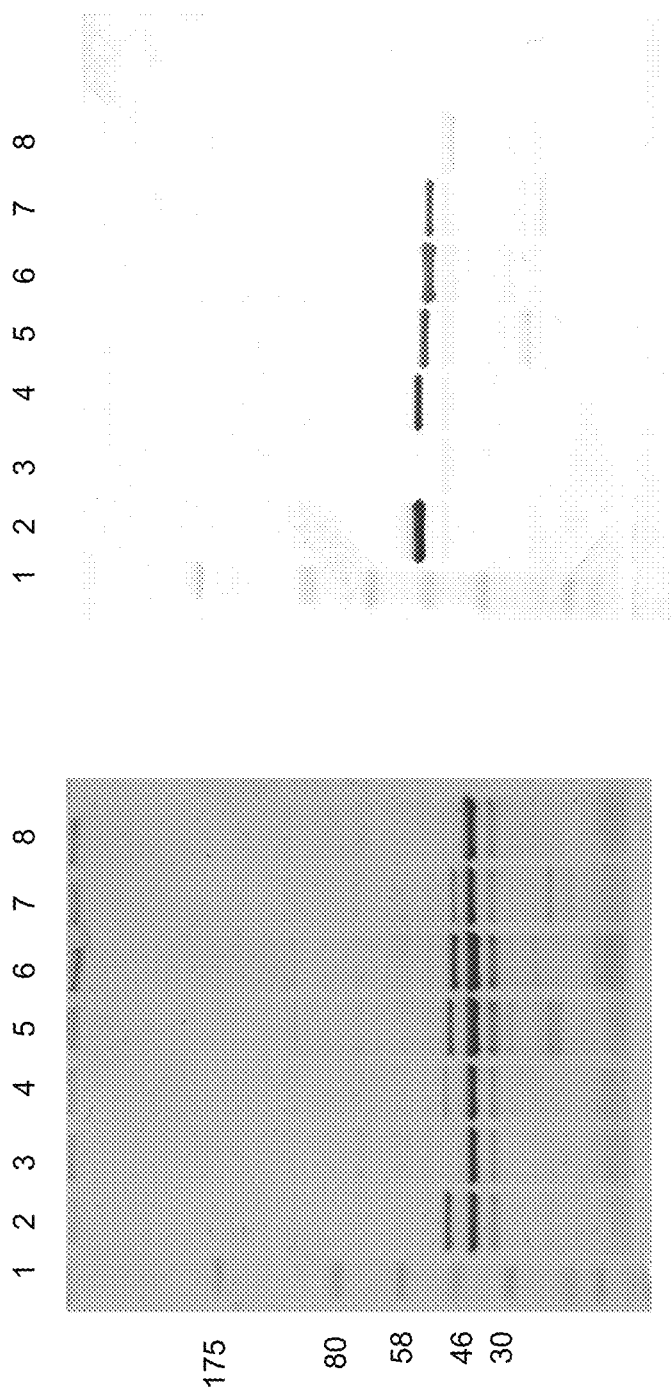

```
PorA MC58        1 MRKKLTALVLSALPLAAVADVSLYGEIKAGVEGRNYQLQLTEAQAANGG-  49
pPORDEL1         1 MRKKLTALVLSALPLAAVADVSLYGEIKAGVEGRNYQ-------------  37
pPorDEL4         1 MRKKLTALVLSALPLAAVADVSLYGEIKAGVEGRNYQLQLTEAQAANGG-  49
pPorDEL1-4       1 MRKKLTALVLSALPLAAVADVSLYGEIKAGVEGRNYQ-------------  37
pPorDEL1-4-5     1 MRKKLTALVLSALPLAAVADVSLYGEIKAGVEGRNYQ-------------  37
pDELVR1          1 MRKKLTALVLSALPLAAVADVSLYGEIKAGVEGRNYQLQLTE--------  42
pDELVR2          1 MRKKLTALVLSALPLAAVADVSLYGEIKAGVEGRNYQLQLTEAQAANGG-  49
pDELVR1-2        1 MRKKLTALVLSALPLAAVADVSLYGEIKAGVEGRNYQLQLTE--------  42
pDELVR1-2-5      1 MRKKLTALVLSALPLAAVADVSLYGEIKAGVEGRNYQLQLTE--------  42
pDELVR1-2-5-6    1 MRKKLTALVLSALPLAAVADVSLYGEIKAGVEGRNYQLQLTE--------  42
pVR2-7           1 MRKKLTALVLSALPLAAVADVSLYGEIKAGVEGRNYQLQLTEAQAANGG-  49
pVR2-8           1 MRKKLTALVLSALPLAAVADVSLYGEIKAGVEGRNYQLQLTEAQAANGG-  49
pDELVR1VR2-7     1 MRKKLTALVLSALPLAAVADVSLYGEIKAGVEGRNYQLQLTE--------  42
pDELVR1VR2-8     1 MRKKLTALVLSALPLAAVADVSLYGEIKAGVEGRNYQLQLTE--------  42
pVR1-7VR2-8      1 MRKKLTALVLSALPLAAVADVSLYGEIKAGVEGRNYQLQLTE--------  42
pVR1-7VR2-8DEL5  1 MRKKLTALVLSALPLAAVADVSLYGEIKAGVEGRNYQLQLTE--------  42
pPor7in1         1 MRKKLTALVLSALPLAAVADVSLYGEIKAGVEGRNYQLQLTEAQAANGGA  50
pPor8in4         1 MRKKLTALVLSALPLAAVADVSLYGEIKAGVEGRNYQLQLTEAQAANGG-  49
pPor7in1-8in4    1 MRKKLTALVLSALPLAAVADVSLYGEIKAGVEGRNYQLQLTEAQAANGGA  50

PorA MC58       50 --------------ASGQVKVTKVTKAKSRIRTKISDFGSFIGFKGSEDLG   86
pPORDEL1        38 ------------------------SRIRTKISDFGSFIGFKGSEDLG     60
pPorDEL4        50 ------------ASGQVKVTKVTKAKSRIRTKISDFGSFIGFKGSEDLG   86
pPorDEL1-4      38 ------------------------SRIRTKISDFGSFIGFKGSEDLG     60
pPorDEL1-4-5    38 ------------------------SRIRTKISDFGSFIGFKGSEDLG     60
pDELVR1         43 ------------------------SRIRTKISDFGSFIGFKGSEDLG     65
pDELVR2         50 ------------ASGQVKVTKVTKAKSRIRTKISDFGSFIGFKGSEDLG   86
pDELVR1-2       43 ------------------------SRIRTKISDFGSFIGFKGSEDLG     65
pDELVR1-2-5     43 ------------------------SRIRTKISDFGSFIGFKGSEDLG     65
pDELVR1-2-5-6   43 ------------------------SRIRTKISDFGSFIGFKGSEDLG     65
pVR2-7          50 ------------ASGQVKVTKVTKAKSRIRTKISDFGSFIGFKGSEDLG   86
pVR2-8          50 ------------ASGQVKVTKVTKAKSRIRTKISDFGSFIGFKGSEDLG   86
pDELVR1VR2-7    43 ------------------------SRIRTKISDFGSFIGFKGSEDLG     65
pDELVR1VR2-8    43 ------------------------SRIRTKISDFGSFIGFKGSEDLG     65
pVR1-7VR2-8     43 FDFIERGKKGENTS--------------SRIRTKISDFGSFIGFKGSEDLG 79
pVR1-7VR2-8DEL5 43 FDFIERGKKGENTS--------------SRIRTKISDFGSFIGFKGSEDLG 79
pPor7in1        51 FDFIERGKKGENTSSGQVKVTKVTKAKSRIRTKISDFGSFIGFKGSEDLG 100
pPor8in4        50 ------------ASGQVKVTKVTKAKSRIRTKISDFGSFIGFKGSEDLG   86
pPor7in1-8in4   51 FDFIERGKKGENTSSGQVKVTKVTKAKSRIRTKISDFGSFIGFKGSEDLG 100
```

FIGURE 1

```
PorA MC58         87  DGLKAVWQLEQDVSVAGGGATQWGNRESFIGLAGEFGTLRAGRVANQFDD 136
pPORDEL1          61  DGLKAVWQLEQDVSVAGGGATQWGNRESFIGLAGEFGTLRAGRVANQFDD 110
pPorDEL4          87  DGLKAVWQLEQDVSVAGGGATQWGNRESFIGLAGEFGTLRAGRVANQFDD 136
pPorDEL1-4        61  DGLKAVWQLEQDVSVAGGGATQWGNRESFIGLAGEFGTLRAGRVANQFDD 110
pPorDEL1-4-5      61  DGLKAVWQLEQDVSVAGGGATQWGNRESFIGLAGEFGTLRAGRVANQFDD 110
pDELVR1           66  DGLKAVWQLEQDVSVAGGGATQWGNRESFIGLAGEFGTLRAGRVANQFDD 115
pDELVR2           87  DGLKAVWQLEQDVSVAGGGATQWGNRESFIGLAGEFGTLRAGRVANQFDD 136
pDELVR1-2         66  DGLKAVWQLEQDVSVAGGGATQWGNRESFIGLAGEFGTLRAGRVANQFDD 115
pDELVR1-2-5       66  DGLKAVWQLEQDVSVAGGGATQWGNRESFIGLAGEFGTLRAGRVANQFDD 115
pDELVR1-2-5-6     66  DGLKAVWQLEQDVSVAGGGATQWGNRESFIGLAGEFGTLRAGRVANQFDD 115
pVR2-7            87  DGLKAVWQLEQDVSVAGGGATQWGNRESFIGLAGEFGTLRAGRVANQFDD 136
pVR2-8            87  DGLKAVWQLEQDVSVAGGGATQWGNRESFIGLAGEFGTLRAGRVANQFDD 136
pDELVR1VR2-7      66  DGLKAVWQLEQDVSVAGGGATQWGNRESFIGLAGEFGTLRAGRVANQFDD 115
pDELVR1VR2-8      66  DGLKAVWQLEQDVSVAGGGATQWGNRESFIGLAGEFGTLRAGRVANQFDD 115
pVR1-7VR2-8       80  DGLKAVWQLEQDVSVAGGGATQWGNRESFIGLAGEFGTLRAGRVANQFDD 129
pVR1-7VR2-8DEL5   80  DGLKAVWQLEQDVSVAGGGATQWGNRESFIGLAGEFGTLRAGRVANQFDD 129
pPor7in1          101 DGLKAVWQLEQDVSVAGGGATQWGNRESFIGLAGEFGTLRAGRVANQFDD 150
pPor8in4          87  DGLKAVWQLEQDVSVAGGGATQWGNRESFIGLAGEFGTLRAGRVANQFDD 136
pPor7in1-8in4     101 DGLKAVWQLEQDVSVAGGGATQWGNRESFIGLAGEFGTLRAGRVANQFDD 150

PorA MC58         137 ASQAIDPWDSNNDVASQLGIFKRHDDMPVSVRYDSPEFSGFSGSVQFVPI 186
pPORDEL1          111 ASQAIDPWDSNNDVASQLGIFKRHDDMPVSVRYDSPEFSGFSGSVQFVPI 160
pPorDEL4          137 ASQAIDPWDSNNDVASQLGIFKRHDDMPVSVRYDSPEFSGFSGSVQFVPI 186
pPorDEL1-4        111 ASQAIDPWDSNNDVASQLGIFKRHDDMPVSVRYDSPEFSGFSGSVQFVPI 160
pPorDEL1-4-5      111 ASQAIDPWDSNNDVASQLGIFKRHDDMPVSVRYDSPEFSGFSGSVQFVPI 160
pDELVR1           116 ASQAIDPWDSNNDVASQLGIFKRHDDMPVSVRYDSPEFSGFSGSVQFVPI 165
pDELVR2           137 ASQAIDPWDSNNDVASQLGIFKRHDDMPVSVRYDSPEFSGFSGSVQFVPI 186
pDELVR1-2         116 ASQAIDPWDSNNDVASQLGIFKRHDDMPVSVRYDSPEFSGFSGSVQFVPI 165
pDELVR1-2-5       116 ASQAIDPWDSNNDVASQLGIFKRHDDMPVSVRYDSPEFSGFSGSVQFVPI 165
pDELVR1-2-5-6     116 ASQAIDPWDSNNDVASQLGIFKRHDDMPVSVRYDSPEFSGFSGSVQFVPI 165
pVR2-7            137 ASQAIDPWDSNNDVASQLGIFKRHDDMPVSVRYDSPEFSGFSGSVQFVPI 186
pVR2-8            137 ASQAIDPWDSNNDVASQLGIFKRHDDMPVSVRYDSPEFSGFSGSVQFVPI 186
pDELVR1VR2-7      116 ASQAIDPWDSNNDVASQLGIFKRHDDMPVSVRYDSPEFSGFSGSVQFVPI 165
pDELVR1VR2-8      116 ASQAIDPWDSNNDVASQLGIFKRHDDMPVSVRYDSPEFSGFSGSVQFVPI 165
pVR1-7VR2-8       130 ASQAIDPWDSNNDVASQLGIFKRHDDMPVSVRYDSPEFSGFSGSVQFVPI 179
pVR1-7VR2-8DEL5   130 ASQAIDPWDSNNDVASQLGIFKRHDDMPVSVRYDSPEFSGFSGSVQFVPI 179
pPor7in1          151 ASQAIDPWDSNNDVASQLGIFKRHDDMPVSVRYDSPEFSGFSGSVQFVPI 200
pPor8in4          137 ASQAIDPWDSNNDVASQLGIFKRHDDMPVSVRYDSPEFSGFSGSVQFVPI 186
pPor7in1-8in4     151 ASQAIDPWDSNNDVASQLGIFKRHDDMPVSVRYDSPEFSGFSGSVQFVPI 200
```

FIGURE 1 cont'd

```
PorA MC58        187 QNSKSAYTPAYYTKNTN------------NNLTLVPAVVGKPGSDVYYA 223
pPORDEL1         161 QNSKSAYTPAYYTKNTN------------NNLTLVPAVVGKPGSDVYYA 197
pPorDEL4         187 ---------------------------------------VVGKPGSDVYYA 198
pPorDEL1-4       161 ---------------------------------------VVGKPGSDVYYA 172
pPorDEL1-4-5     161 ---------------------------------------VVGKPGSDVYYA 172
pDELVR1          166 QNSKSAYTPAYYTKNTN------------NNLTLVPAVVGKPGSDVYYA 202
pDELVR2          187 QNSKSAYTP-------------------------APAVVGKPGSDVYYA 210
pDELVR1-2        166 QNSKSAYTP-------------------------APAVVGKPGSDVYYA 189
pDELVR1-2-5      166 QNSKSAYTP-------------------------APAVVGKPGSDVYYA 189
pDELVR1-2-5-6    166 QNSKSAYTPA------------------------PAVVGKPGSDVYYA 189
pVR2-7           187 QNSKSAYTPAFDFIERGKKGENT------------SPAVVGKPGSDVYYA 224
pVR2-8           187 QNSKSAYTPAKRNTGIGNYTQIN------------PAVVGKPGSDVYYA 223
pDELVR1VR2-7     166 QNSKSAYTPAFDFIERGKKGENT------------SPAVVGKPGSDVYYA 203
pDELVR1VR2-8     166 QNSKSAYTPA-------KRNTGIGNYTQIN------PAVVGKPGSDVYYA 202
pVR1-7VR2-8      180 QNSKSAYTPA-------KRNTGIGNYTQIN------PAVVGKPGSDVYYA 216
pVR1-7VR2-8DEL5  180 QNSKSAYTPA-------KRNTGIGNYTQIN------PAVVGKPGSDVYYA 216
pPor7in1         201 QNSKSAYTPAYYTKNTN------------NNLTLVPAVVGKPGSDVYYA 237
pPor8in4         187 QNSKSAYTPAYYTKNTNKRNTGIGNYTQINNNLTLVPAVVGKPGSDVYYA 236
pPor7in1-8in4    201 QNSKSAYTPAYYTKNTNKRNTGIGNYTQINNNLTLVPAVVGKPGSDVYYA 250

PorA MC58        224 GLNYKNGGFAGNYAFKYARHANVGRNAFELFLIGSGSDQAKGTDPLKNHQ 273
pPORDEL1         198 GLNYKNGGFAGNYAFKYARHANVGRNAFELFLIGSGSDQAKGTDPLKNHQ 247
pPorDEL4         199 GLNYKNGGFAGNYAFKYARHANVGRNAFELFLIGSGSDQAKGTDPLKNHQ 248
pPorDEL1-4       173 GLNYKNGGFAGNYAFKYARHANVGRNAFELFLIGSGSDQAKGTDPLKNHQ 222
pPorDEL1-4-5     173 GLNYKNGGFAGNYAFKYARHANVG--------------------LKNHQ 201
pDELVR1          203 GLNYKNGGFAGNYAFKYARHANVGRNAFELFLIGSGSDQAKGTDPLKNHQ 252
pDELVR2          211 GLNYKNGGFAGNYAFKYARHANVGRNAFELFLIGSGSDQAKGTDPLKNHQ 260
pDELVR1-2        190 GLNYKNGGFAGNYAFKYARHANVGRNAFELFLIGSGSDQAKGTDPLKNHQ 239
pDELVR1-2-5      190 GLNYKNGGFAGNYAFKYARHANVG--------------------LKNHQ 218
pDELVR1-2-5-6    190 GLNYKNGGFAGNYAFKYARHANVG--------------------LKNHQ 218
pVR2-7           225 GLNYKNGGFAGNYAFKYARHANVGRNAFELFLIGSGSDQAKGTDPLKNHQ 274
pVR2-8           224 GLNYKNGGFAGNYAFKYARHANVGRNAFELFLIGSGSDQAKGTDPLKNHQ 273
pDELVR1VR2-7     204 GLNYKNGGFAGNYAFKYARHANVGRNASELFLIGSGSDQAKGTDPLKNHQ 253
pDELVR1VR2-8     203 GLNYKNGGFAGNYAFKYARHANVGRNAFELFLIGSGSDQAKGTDPLKNHQ 252
pVR1-7VR2-8      217 GLNYKNGGFAGNYAFKYARHANVGRNAFELFLIGSGSDQAKGTDPLKNHQ 266
pVR1-7VR2-8DEL5  217 GLNYKNGGFAGNYAFKYARHANVG--------------------LKNHQ 245
pPor7in1         238 GLNYKNGGFAGNYAFKYARHANVGRNAFELFLIGSGSDQAKGTDPLKNHQ 287
pPor8in4         237 GLNYKNGGFAGNYAFKYARHANVGRNAFELFLIGSGSDQAKGTDPLKNHQ 286
pPor7in1-8in4    251 GLNYKNGGFAGNYAFKYARHANVGRNAFELFLIGSGSDQAKGTDPLKNHQ 300
```

FIGURE 1 cont'd

```
PorA MC58        274 VHRLTGGYEEGGLNLALAAQLDLSENGDKTKNSTTEIAATASYRFGNAVP 323
pPORDEL1         248 VHRLTGGYEEGGLNLALAAQLDLSENGDKTKNSTTEIAATASYRFGNAVP 297
pPorDEL4         249 VHRLTGGYEEGGLNLALAAQLDLSENGDKTKNSTTEIAATASYRFGNAVP 298
pPorDEL1-4       223 VHRLTGGYEEGGLNLALAAQLDLSENGDKTKNSTTEIAATASYRFGNAVP 272
pPorDEL1-4-5     202 VHRLTGGYEEGGLNLALAAQLDLSENGDKTKNSTTEIAATASYRFGNAVP 251
pDELVR1          253 VHRLTGGYEEGGLNLALAAQLDLSENGDKTKNSTTEIAATASYRFGNAVP 302
pDELVR2          261 VHRLTGGYEEGGLNLALAAQLDLSENGDKTKNSTTEIAATASYRFGNAVP 310
pDELVR1-2        240 VHRLTGGYEEGGLNLALAAQLDLSENGDKTKNSTTEIAATASYRFGNAVP 289
pDELVR1-2-5      219 VHRLTGGYEEGGLNLALAAQLDLSENGDKTKNSTTEIAATASYRFGNAVP 268
pDELVR1-2-5-6    219 VHRLTGGYEEGGLNLALAAQLDLS--------STTEIAATASYRFGNAVP 260
pVR2-7           275 VHRLTGGYEEGGLNLALAAQLDLSENGDKTKNSTTEIAATASYRFGNAVP 324
pVR2-8           274 VHRLTGGYEEGGLNLALAAQLDLSENGDKTKNSTTEIAATASYRFGNAVP 323
pDELVR1VR2-7     254 VHRLTGGYEEGGLNLALAAQLDLSENGDKTKNSTTEIAATASYRFGNAVP 303
pDELVR1VR2-8     253 VHRLTGGYEEGGLNLALAAQLDLSENGDKTKNSTTEIAATASYRFGNAVP 302
pVR1-7VR2-8      267 VHRLTGGYEEGGLNLALAAQLDLSENGDKTKNSTTEIAATASYRFGNAVP 316
pVR1-7VR2-8DEL5  246 VHRLTGGYEEGGLNLALAAQLDLSENGDKTKNSTTEIAATASYRFGNAVP 295
pPor7in1         288 VHRLTGGYEEGGLNLALAAQLDLSENGDKTKNSTTEIAATASYRFGNAVP 337
pPor8in4         287 VHRLTGGYEEGGLNLALAAQLDLSENGDKTKNSTTEIAATASYRFGNAVP 336
pPor7in1-8in4    301 VHRLTGGYEEGGLNLALAAQLDLSENGDKTKNSTTEIAATASYRFGNAVP 350

PorA MC58        324 RISYAHGFDFIERGKKGENTSYDQIIAGVDYDFSKRTSAIVSGAWLKRNT 373
pPORDEL1         298 RISYAHGFDFIERGKKGENTSYDQIIAGVDYDFSKRTSAIVSGAWLKRNT 347
pPorDEL4         299 RISYAHGFDFIERGKKGENTSYDQIIAGVDYDFSKRTSAIVSGAWLKRNT 348
pPorDEL1-4       273 RISYAHGFDFIERGKKGENTSYDQIIAGVDYDFSKRTSAIVSGAWLKRNT 322
pPorDEL1-4-5     252 RISYAHGFDFIERGKKGENTSYDQIIAGVDYDFSKRTSAIVSGAWLKRNT 301
pDELVR1          303 RISYAHGFDFIERGKKGENTSYDQIIAGVDYDFSKRTSAIVSGAWLKRNT 352
pDELVR2          311 RISYAHGFDFIERGKKGENTSYDQIIAGVDYDFSKRTSAIVSGAWLKRNT 360
pDELVR1-2        290 RISYAHGFDFIERGKKGENTSYDQIIAGVDYDFSKRTSAIVSGAWLKRNT 339
pDELVR1-2-5      269 RISYAHGFDFIERGKKGENTSYDQIIAGVDYDFSKRTSAIVSGAWLKRNT 318
pDELVR1-2-5-6    261 RISYAHGFDFIERGKKGENTSYDQIIAGVDYDFSKRTSAIVSGAWLKRNT 310
pVR2-7           325 RISYAHGFDFIERGKKGENTSYDQIIAGVDYDFSKRTSAIVSGAWLKRNT 374
pVR2-8           324 RISYAHGFDFIERGKKGENTSYDQIIAGVDYDFSKRTSAIVSGAWLKRNT 373
pDELVR1VR2-7     304 RISYAHGFDFIERGKKGENTSYDQIIAGVDYDFSKRTSAIVSGAWLKRNT 353
pDELVR1VR2-8     303 RISYAHGFDFIERGKKGENTSYDQIIAGVDYDFSKRTSAIVSGAWLKRNT 352
pVR1-7VR2-8      317 RISYAHGFDFIERGKKGENTSYDQIIAGVDYDFSKRTSAIVSGAWLKRNT 366
pVR1-7VR2-8DEL5  296 RISYAHGFDFIERGKKGENTSYDQIIAGVDYDFSKRTSAIVSGAWLKRNT 345
pPor7in1         338 RISYAHGFDFIERGKKGENTSYDQIIAGVDYDFSKRTSAIVSGAWLKRNT 387
pPor8in4         337 RISYAHGFDFIERGKKGENTSYDQIIAGVDYDFSKRTSAIVSGAWLKRNT 386
pPor7in1-8in4    351 RISYAHGFDFIERGKKGENTSYDQIIAGVDYDFSKRTSAIVSGAWLKRNT 400
```

FIGURE 1 cont'd

```
PorA MC58          374 GIGNYTQINAASVGLRHKF 392
pPORDEL1           348 GIGNYTQINAASVGLRHKF 366
pPorDEL4           349 GIGNYTQINAASVGLRHKF 367
pPorDEL1-4         323 GIGNYTQINAASVGLRHKF 341
pPorDEL1-4-5       302 GIGNYTQINAASVGLRHKF 320
pDELVR1            353 GIGNYTQINAASVGLRHKF 371
pDELVR2            361 GIGNYTQINAASVGLRHKF 379
pDELVR1-2          340 GIGNYTQINAASVGLRHKF 358
pDELVR1-2-5        319 GIGNYTQINAASVGLRHKF 337
pDELVR1-2-5-6      311 GIGNYTQINAASVGLRHKF 329
pVR2-7             375 GIGNYTQINAASVGLRHKF 393
pVR2-8             374 GIGNYTQINAASVGLRHKF 392
pDELVR1VR2-7       354 GIGNYTQINAASVGLRHKF 372
pDELVR1VR2-8       353 GIGNYTQINAASVGLRHKF 371
pVR1-7VR2-8        367 GIGNYTQINAASVGLRHKF 385
pVR1-7VR2-8DEL5    346 GIGNYTQINAASVGLRHKF 364
pPor7in1           388 GIGNYTQINAASVGLRHKF 406
pPor8in4           387 GIGNYTQINAASVGLRHKF 405
pPor7in1-8in4      401 GIGNYTQINAASVGLRHKF 419
```

FIGURE 1 cont'd

DNA seq pPorΔL1
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGAGCCGCATCAGGACGAAAATCAGTGATTTCGGCTCGTTTATCG
GCTTTAAGGGGAGTGAGGATTTGGGCGACGGGCTGAAGGCTGTTTGGCAGCTTGAGCAAGACGTATCCGTTGCCGGC
GGCGGCGCGACCCAGTGGGGCAACAGGGAATCCTTTATCGGCTTGGCAGGCGAATTCGGTACGCTGCGCGCCGGTCG
CGTTGCGAATCAGTTTGACGATGCCAGCCAAGCCATTGATCCTTGGGACAGCAATAATGATGTGGCTTCGCAATTGG
GTATTTTCAAACGCCACGACGACATGCCGGTTTCCGTACGCTACGATTCCCCCGAATTTTCCGGTTTCAGCGGCAGC
GTTCAATTCGTTCCGATCCAAAACAGCAAGTCCGCCTATACGCCGGCTTATTATACTAAGAATACAAACAATAATCT
TACTCTCGTTCCGGCTGTTGTCGGCAAGCCCGGATCGGATGTGTATTATGCCGGTCTGAATTACAAAAATGGCGGTT
TTGCCGGGAACTATGCCTTTAAATATGCGAGACACGCCAATGTCGGACGTAATGCTTTTGAGTTGTTCTTGATCGGC
AGCGGGAGTGATCAAGCCAAAGGTACCGATCCCTTGAAAAACCATCAGGTACACCGTCTGACGGGCGGCTATGAGGA
AGGCGGCTTGAATCTCGCCTTGGCGGCTCAGTTGGATTTGTCTGAAAATGGCGACAAAACCAAAAACAGTACGACCG
AAATTGCCGCCACTGCTTCCTACCGCTTCGGTAATGCAGTTCCACGCATCAGCTATGCCCATGGTTTCGACTTTATC
GAACGCGGTAAAAAGGCGAAAATACCAGCTACGATCAAATCATCGCCGGCGTTGATTATGATTTTTCCAAACGCAC
TTCCGCCATCGTGTCTGGCGCTTGGCTGAAACGCAATACCGGCATCGGCAACTACACTCAAATTAATGCCGCCTCCG
TCGGTTTGCGCCACAAATTCTAA

AA seq pPorΔL1
MRKKLTALVLSALPLAAVADVSLYGEIKAGVEGRNYQSRIRTKISDFGSFIGFKGSEDLGDGLKAVWQLEQDVSVAG
GGATQWGNRESFIGLAGEFGTLRAGRVANQFDDASQAIDPWDSNNDVASQLGIFKRHDDMPVSVRYDSPEFSGFSGS
VQFVPIQNSKSAYTPAYYTKNTNNNLTLVPAVVGKPGSDVYYAGLNYKNGGFAGNYAFKYARHANVGRNAFELFLIG
SGSDQAKGTDPLKNHQVHRLTGGYEEGGLNLALAAQLDLSENGDKTKNSTTEIAATASYRFGNAVPRISYAHGFDFI
ERGKKGENTSYDQIIAGVDYDFSKRTSAIVSGAWLKRNTGIGNYTQINAASVGLRHKF*

DNA seq pPorΔL4
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGAGCG
GTCAGGTAAAAGTTACTAAAGTTACTAAGGCCAAAAGCCGCATCAGGACGAAAATCAGTGATTTCGGCTCGTTTATC
GGCTTTAAGGGGAGTGAGGATTTGGGCGACGGGCTGAAGGCTGTTTGGCAGCTTGAGCAAGACGTATCCGTTGCCGG
CGGCGGCGCGACCCAGTGGGGCAACAGGGAATCCTTTATCGGCTTGGCAGGCGAATTCGGTACGCTGCGCGCCGGTC
GCGTTGCGAATCAGTTTGACGATGCCAGCCAAGCCATTGATCCTTGGGACAGCAATAATGATGTGGCTTCGCAATTG
GGTATTTTCAAACGCCACGACGACATGCCGGTTTCCGTACGCTACGATTCCCCCGAATTTTCCGGTTTCAGCGGCAG
CGTTCAATTCGTTCCGATCGTTGTCGGCAAGCCCGGATCGGATGTGTATTATGCCGGTCTGAATTACAAAAATGGCG
GTTTTGCCGGGAACTATGCCTTTAAATATGCGAGACACGCCAATGTCGGACGTAATGCTTTTGAGTTGTTCTTGATC
GGCAGCGGGAGTGATCAAGCCAAAGGTACCGATCCCTTGAAAAACCATCAGGTACACCGTCTGACGGGCGGCTATGA
GGAAGGCGGCTTGAATCTCGCCTTGGCGGCTCAGTTGGATTTGTCTGAAAATGGCGACAAAACCAAAAACAGTACGA
CCGAAATTGCCGCCACTGCTTCCTACCGCTTCGGTAATGCAGTTCCACGCATCAGCTATGCCCATGGTTTCGACTTT
ATCGAACGCGGTAAAAAGGCGAAAATACCAGCTACGATCAAATCATCGCCGGCGTTGATTATGATTTTTCCAAACG
CACTTCCGCCATCGTGTCTGGCGCTTGGCTGAAACGCAATACCGGCATCGGCAACTACACTCAAATTAATGCCGCCT
CCGTCGGTTTGCGCCACAAATTCTAA

AA seq pPorΔL4
MRKKLTALVLSALPLAAVADVSLYGEIKAGVEGRNYQLQLTEAQAANGGASGQVKVTKVTKAKSRIRTKISDFGSFI
GFKGSEDLGDGLKAVWQLEQDVSVAGGGATQWGNRESFIGLAGEFGTLRAGRVANQFDDASQAIDPWDSNNDVASQL
GIFKRHDDMPVSVRYDSPEFSGFSGSVQFVPIVVGKPGSDVYYAGLNYKNGGFAGNYAFKYARHANVGRNAFELFLI
GSGSDQAKGTDPLKNHQVHRLTGGYEEGGLNLALAAQLDLSENGDKTKNSTTEIAATASYRFGNAVPRISYAHGFDF
IERGKKGENTSYDQIIAGVDYDFSKRTSAIVSGAWLKRNTGIGNYTQINAASVGLRHKF*

FIGURE 2A cont'd

DNA seq pPorΔL1-4
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGAGCCGCATCAGGACGAAAATCAGTGATTTCGGCTCGTTTATCG
GCTTTAAGGGGAGTGAGGATTTGGGCGACGGGCTGAAGGCTGTTTGGCAGCTTGAGCAAGACGTATCCGTTGCCGGC
GGCGGCGCGACCCAGTGGGGCAACAGGGAATCCTTTATCGGCTTGGCAGGCGAATTCGGTACGCTGCGCGCCGGTCG
CGTTGCGAATCAGTTTGACGATGCCAGCCAAGCCATTGATCCTTGGGACAGCAATAATGATGTGGCTTCGCAATTGG
GTATTTTCAAACGCCACGACGACATGCCGGTTTCCGTACGCTACGATTCCCCCGAATTTTCCGGTTTCAGCGGCAGC
GTTCAATTCGTTCCGATCGTTGTCGGCAAGCCCGGATCGGATGTGTATTATGCCGGTCTGAATTACAAAAATGGCGG
TTTTGCCGGGAACTATGCCTTTAAATATGCGAGACACGCCAATGTCGGACGTAATGCTTTTGAGTTGTTCTTGATCG
GCAGCGGGAGTGATCAAGCCAAAGGTACCGATCCCTTGAAAAACCATCAGGTACACCGTCTGACGGGCGGCTATGAG
GAAGGCGGCTTGAATCTCGCCTTGGCGGCTCAGTTGGATTTGTCTGAAAATGGCGACAAAACCAAAAACAGTACGAC
CGAAATTGCCGCCACTGCTTCCTACCGCTTCGGTAATGCAGTTCCACGCATCAGCTATGCCCATGGTTTCGACTTTA
TCGAACGCGGTAAAAAGGCGAAAATACCAGCTACGATCAAATCATCGCCGGCGTTGATTATGATTTTTCCAAACGC
ACTTCCGCCATCGTGTCTGGCGCTTGGCTGAAACGCAATACCGGCATCGGCAACTACACTCAAATTAATGCCGCCTC
CGTCGGTTTGCGCCACAAATTCTAA

AA seq pPorΔL1-4
MRKKLTALVLSALPLAAVADVSLYGEIKAGVEGRNYQSRIRTKISDFGSFIGFKGSEDLGDGLKAVWQLEQDVSVAG
GGATQWGNRESFIGLAGEFGTLRAGRVANQFDDASQAIDPWDSNNDVASQLGIFKRHDDMPVSVRYDSPEFSGFSGS
VQFVPIVVGKPGSDVYYAGLNYKNGGFAGNYAFKYARHANVGRNAFELFLIGSGSDQAKGTDPLKNHQVHRLTGGYE
EGGLNLALAAQLDLSENGDKTKNSTTEIAATASYRFGNAVPRISYAHGFDFIERGKKGENTSYDQIIAGVDYDFSKR
TSAIVSGAWLKRNTGIGNYTQINAASVGLRHKF*

DNA seq pPorDEL1-4-5
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGAGCCGCATCAGGACGAAAATCAGTGATTTCGGCTCGTTTATCG
GCTTTAAGGGGAGTGAGGATTTGGGCGACGGGCTGAAGGCTGTTTGGCAGCTTGAGCAAGACGTATCCGTTGCCGGC
GGCGGCGCGACCCAGTGGGGCAACAGGGAATCCTTTATCGGCTTGGCAGGCGAATTCGGTACGCTGCGCGCCGGTCG
CGTTGCGAATCAGTTTGACGATGCCAGCCAAGCCATTGATCCTTGGGACAGCAATAATGATGTGGCTTCGCAATTGG
GTATTTTCAAACGCCACGACGACATGCCGGTTTCCGTACGCTACGATTCCCCCGAATTTTCCGGTTTCAGCGGCAGC
GTTCAATTCGTTCCGATCGTTGTCGGCAAGCCCGGATCGGATGTGTATTATGCCGGTCTGAATTACAAAAATGGCGG
TTTTGCCGGGAACTATGCCTTTAAATATGCGAGACACGCCAATGTCGGATTGAAAAACCATCAGGTACACCGTCTGA
CGGGCGGCTATGAGGAAGGCGGCTTGAATCTCGCCTTGGCGGCTCAGTTGGATTTGTCTGAAAATGGCGACAAAACC
AAAAACAGTACGACCGAAATTGCCGCCACTGCTTCCTACCGCTTCGGTAATGCAGTTCCACGCATCAGCTATGCCCA
TGGTTTCGACTTTATCGAACGCGGTAAAAAGGCGAAAATACCAGCTACGATCAAATCATCGCCGGCGTTGATTATG
ATTTTTCCAAACGCACTTCCGCCATCGTGTCTGGCGCTTGGCTGAAACGCAATACCGGCATCGGCAACTACACTCAA
ATTAATGCCGCCTCCGTCGGTTTGCGCCACAAATTCTAA

AA seq pPorDEL1-4-5
MRKKLTALVLSALPLAAVADVSLYGEIKAGVEGRNYQSRIRTKISDFGSFIGFKGSEDLGDGLKAVWQLEQDVSVAG
GGATQWGNRESFIGLAGEFGTLRAGRVANQFDDASQAIDPWDSNNDVASQLGIFKRHDDMPVSVRYDSPEFSGFSGS
VQFVPIVVGKPGSDVYYAGLNYKNGGFAGNYAFKYARHANVGLKNHQVHRLTGGYEEGGLNLALAAQLDLSENGDKT
KNSTTEIAATASYRFGNAVPRISYAHGFDFIERGKKGENTSYDQIIAGVDYDFSKRTSAIVSGAWLKRNTGIGNYTQ
INAASVGLRHKF*

FIGURE 2A cont'd

DNA seq pDELVR1
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTTATTATACTAAGAA
TACAAACAATAATCTTACTCTCGTTCCGGCTGTTGTCGGCAAGCCCGGATCGGATGTGTATTATGCCGGTCTGAATT
ACAAAAATGGCGGTTTTGCCGGGAACTATGCCTTTAAATATGCGAGACACGCCAATGTCGGACGTAATGCTTTTGAG
TTGTTCTTGATCGGCAGCGGGAGTGATCAAGCCAAAGGTACCGATCCCTTGAAAAACCATCAGGTACACCGTCTGAC
GGGCGGCTATGAGGAAGGCGGCTTGAATCTCGCCTTGGCGGCTCAGTTGGATTTGTCTGAAAATGGCGACAAAACCA
AAAACAGTACGACCGAAATTGCCGCCACTGCTTCCTACCGCTTCGGTAATGCAGTTCCACGCATCAGCTATGCCCAT
GGTTTCGACTTTATCGAACGCGGTAAAAAAGGCGAAAATACCAGCTACGATCAAATCATCGCCGGCGTTGATTATGA
TTTTTCCAAACGCACTTCCGCCATCGTGTCTGGCGCTTGGCTGAAACGCAATACCGGCATCGGCAACTACACTCAAA
TTAATGCCGCCTCCGTCGGTTTGCGCCACAAATTCTAA

AA seq pDELVR1
MRKKLTALVLSALPLAAVADVSLYGEIKAGVEGRNYQLQLTESRIRTKISDFGSFIGFKGSEDLGDGLKAVWQLEQD
VSVAGGGATQWGNRESFIGLAGEFGTLRAGRVANQFDDASQAIDPWDSNNDVASQLGIFKRHDDMPVSVRYDSPEFS
GFSGSVQFVPIQNSKSAYTPAYYTKNTNNNLTLVPAVVGKPGSDVYYAGLNYKNGGFAGNYAFKYARHANVGRNAFE
LFLIGSGSDQAKGTDPLKNHQVHRLTGGYEEGGLNLALAAQLDLSENGDKTKNSTTEIAATASYRFGNAVPRISYAH
GFDFIERGKKGENTSYDQIIAGVDYDFSKRTSAIVSGAWLKRNTGIGNYTQINAASVGLRHKF*

DNA seq pDELVR2
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGAGCG
GTCAGGTAAAAGTTACTAAAGTTACTAAGGCCAAAAGCCGCATCAGGACGGAAAATCAGTGATTTCGGCTCGTTTATC
GGCTTTAAGGGGAGTGAGGATTTGGGCGACGGGCTGAAGGCTGTTTGGCAGCTTGAGCAAGACGTATCCGTTGCCGG
CGGCGGCGCGACCCAGTGGGGCAACAGGGAATCCTTTATCGGCTTGGCAGGCGAATTCGGTACGCTGCGCGCCGGTC
GCGTTGCGAATCAGTTTGACGATGCCAGCCAAGCCATTGATCCTTGGGACAGCAATAATGATGTGGCTTCGCAATTG
GGTATTTTCAAACGCCACGACGACATGCCGGTTTCCGTACGCTACGATTCCCCCGAATTTTCCGGTTTCAGCGGCAG
CGTTCAATTCGTTCCGATCCAAAACAGCAAGTCCGCCTATACGCCGGCTCCGGCTGTTGTCGGCAAGCCCGGATCGG
ATGTGTATTATGCCGGTCTGAATTACAAAAATGGCGGTTTTGCCGGGAACTATGCCTTTAAATATGCGAGACACGCC
AATGTCGGACGTAATGCTTTTGAGTTGTTCTTGATCGGCAGCGGGAGTGATCAAGCCAAAGGTACCGATCCCTTGAA
AAACCATCAGGTACACCGTCTGACGGGCGGCTATGAGGAAGGCGGCTTGAATCTCGCCTTGGCGGCTCAGTTGGATT
TGTCTGAAAATGGCGACAAAACCAAAAACAGTACGACCGAAATTGCCGCCACTGCTTCCTACCGCTTCGGTAATGCA
GTTCCACGCATCAGCTATGCCCATGGTTTCGACTTTATCGAACGCGGTAAAAAAGGCGAAAATACCAGCTACGATCA
AATCATCGCCGGCGTTGATTATGATTTTTCCAAACGCACTTCCGCCATCGTGTCTGGCGCTTGGCTGAAACGCAATA
CCGGCATCGGCAACTACACTCAAATTAATGCCGCCTCCGTCGGTTTGCGCCACAAATTCTAA

AA seq pDELVR2
MRKKLTALVLSALPLAAVADVSLYGEIKAGVEGRNYQLQLTEAQAANGGASGQVKVTKVTKAKSRIRTKISDFGSFI
GFKGSEDLGDGLKAVWQLEQDVSVAGGGATQWGNRESFIGLAGEFGTLRAGRVANQFDDASQAIDPWDSNNDVASQL
GIFKRHDDMPVSVRYDSPEFSGFSGSVQFVPIQNSKSAYTPAPAVVGKPGSDVYYAGLNYKNGGFAGNYAFKYARHA
NVGRNAFELFLIGSGSDQAKGTDPLKNHQVHRLTGGYEEGGLNLALAAQLDLSENGDKTKNSTTEIAATASYRFGNA
VPRISYAHGFDFIERGKKGENTSYDQIIAGVDYDFSKRTSAIVSGAWLKRNTGIGNYTQINAASVGLRHKF*

FIGURE 2A cont'd

DNA seq pDELVR1-2
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTCCGGCTGTTGTCGG
CAAGCCCGGATCGGATGTGTATTATGCCGGTCTGAATTACAAAAATGGCGGTTTTGCCGGGAACTATGCCTTTAAAT
ATGCGAGACACGCCAATGTCGGACGTAATGCTTTTGAGTTGTTCTTGATCGGCAGCGGGAGTGATCAAGCCAAAGCT
ACCGATCCCTTGAAAAACCATCAGGTACACCGTCTGACGGGCGGCTATGAGGAAGGCGGCTTGAATCTCGCCTTGGC
GGCTCAGTTGGATTTGTCTGAAAATGGCGACAAAACCAAAAACAGTACGACCGAAATTGCCGCCACTGCTTCCTACC
GCTTCGGTAATGCAGTTCCACGCATCAGCTATGCCCATGGTTTCGACTTTATCGAACGCGGTAAAAAAGGCGAAAAT
ACCAGCTACGATCAAATCATCGCCGGCGTTGATTATGATTTTTCCAAACGCACTTCCGCCATCGTGTCTGGCGCTTG
GCTGAAACGCAATACCGGCATCGGCAACTACACTCAAATTAATGCCGCCTCCGTCGGTTTGCGCCACAAATTCTAA

AA seq pDELVR1-2
MRKKLTALVLSALPLAAVADVSLYGEIKAGVEGRNYQLQLTESRIRTKISDFGSFIGFKGSEDLGDGLKAVWQLEQD
VSVAGGGATQWGNRESFIGLAGEFGTLRAGRVANQFDDASQAIDPWDSNNDVASQLGIFKRHDDMPVSVRYDSPEFS
GFSGSVQFVPIQNSKSAYTPAPAVVGKPGSDVYYAGLNYKNGGFAGNYAFKYARHANVGRNAFELFLIGSGSDQAKG
TDPLKNHQVHRLTGGYEEGGLNLALAAQLDLSENGDKTKNSTTEIAATASYRFGNAVPRISYAHGFDFIERGKKGEN
TSYDQIIAGVDYDFSKRTSAIVSGAWLKRNTGIGNYTQINAASVGLRHKF*

DNA seq pDELVR1-2-5
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTCCGGCTGTTGTCGG
CAAGCCCGGATCGGATGTGTATTATGCCGGTCTGAATTACAAAAATGGCGGTTTTGCCGGGAACTATGCCTTTAAAT
ATGCGAGACACGCCAATGTCGGATTGAAAAACCATCAGGTACACCGTCTGACGGGCGGCTATGAGGAAGGCGGCTTG
AATCTCGCCTTGGCGGCTCAGTTGGATTTGTCTGAAAATGGCGACAAAACCAGTACGACCGAAATTGCCGC
CACTGCTTCCTACCGCTTCGGTAATGCAGTTCCACGCATCAGCTATGCCCATGGTTTCGACTTTATCGAACGCGGTA
AAAAAGGCGAAAATACCAGCTACGATCAAATCATCGCCGGCGTTGATTATGATTTTTCCAAACGCACTTCCGCCATC
GTGTCTGGCGCTTGGCTGAAACGCAATACCGGCATCGGCAACTACACTCAAATTAATGCCGCCTCCGTCGGTTTGCG
CCACAAATTCTAA

AA seq pDELVR1-2-5
MRKKLTALVLSALPLAAVADVSLYGEIKAGVEGRNYQSRIRTKISDFGSFIGFKGSEDLGDGLKAVWQLEQDVSVAG
GGATQWGNRESFIGLAGEFGTLRAGRVANQFDDASQAIDPWDSNNDVASQLGIFKRHDDMPVSVRYDSPEFSGFSGS
VQFVPIVVGKPGSDVYYAGLNYKNGGFAGNYAFKYARHANVGLKNHQVHRLTGGYEEGGLNLALAAQLDLSENGDKT
KNSTTEIAATASYRFGNAVPRISYAHGFDFIERGKKGENTSYDQIIAGVDYDFSKRTSAIVSGAWLKRNTGIGNYTQ
INAASVGLRHKF*

FIGURE 2A cont'd

DNA seq pVR2-7
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGAGCG
GTCAGGTAAAAGTTACTAAAGTTACTAAGGCCAAAAGCCGCATCAGGACGAAAATCAGTGATTTCGGCTCGTTTATC
GGCTTTAAGGGGAGTGAGGATTTGGGCGACGGGCTGAAGGCTGTTTGGCAGCTTGAGCAAGACGTATCCGTTGCCGG
CGGCGGCGCGACCCAGTGGGCAACAGGGAATCCTTTATCGGCTTGGCAGGCGAATTCGGTACGCTGCGCGCCGGTC
GCGTTGCGAATCAGTTTGACGATGCCAGCCAAGCCATTGATCCTTGGGACAGCAATAATGATGTGGCTTCGCAATTG
GGTATTTTCAAACGCCACGACGACATGCCGGTTTCCGTACGCTACGATTCCCCCGAATTTTCCGGTTTCAGCGGCAG
CGTTCAATTCGTTCCGATCCAAAACAGCAAGTCCGCCTATACGCCGGCTTTCGACTTTATCGAACGCGGTAAAAAAG
GCGAAAATACCAGCCCGGCTGTTGTCGGCAAGCCCGGATCGGATGTGTATTATGCCGGTCTGAATTACAAAAATGGC
GGTTTTGCCGGGAACTATGCCTTTAAATATGCGAGACACGCCAATGTCGGACGTAATGCTTTTGAGTTGTTCTTGAT
CGGCAGCGGGAGTGATCAAGCCAAAGGTACCGATCCCTTGAAAAACCATCAGGTACACCGTCTGACGGGCGGCTATG
AGGAAGGCGGCTTGAATCTCGCCTTGGCGGCTCAGTTGGATTTGTCTGAAAATGGCGACAAAACCAAAAACAGTACG
ACCGAAATTGCCGCCACTGCTTCCTACCGCTTCGGTAATGCAGTTCCACGCATCAGCTATGCCCATGGTTTCGACTT
TATCGAACGCGGTAAAAAAGGCGAAAATACCAGCTACGATCAAATCATCGCCGGCGTTGATTATGATTTTCCAAAC
GCACTTCCGCCATCGTGTCTGGCGCTTGGCTGAAACGCAATACCGGCATCGGCAACTACACTCAAATTAATGCCGCC
TCCGTCGGTTTGCGCCACAAATTCTAA

AA seq pVR2-7
MRKKLTALVLSALPLAAVADVSLYGEIKAGVEGRNYQLQLTEAQAANGGASGQVKVTKVTKAKSRIRTKISDFGSFI
GFKGSEDLGDGLKAVWQLEQDVSVAGGGATQWGNRESFIGLAGEFGTLRAGRVANQFDDASQAIDPWDSNNDVASQL
GIFKRHDDMPVSVRYDSPEFSGFSGSVQFVPIQNSKSAYTPAFDFIERGKKGENTSPAVVGKPGSDVYYAGLNYKNG
GFAGNYAFKYARHANVGRNAFELFLIGSGSDQAKGTDPLKNHQVHRLTGGYEEGGLNLALAAQLDLSENGDKTKNST
TEIAATASYRFGNAVPRISYAHGFDFIERGKKGENTSYDQIIAGVDYDFSKRTSAIVSGAWLKRNTGIGNYTQINAA
SVGLRHKF*

DNA seq pVR2-8
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGAGCG
GTCAGGTAAAAGTTACTAAAGTTACTAAGGCCAAAAGCCGCATCAGGACGAAAATCAGTGATTTCGGCTCGTTTATC
GGCTTTAAGGGGAGTGAGGATTTGGGCGACGGGCTGAAGGCTGTTTGGCAGCTTGAGCAAGACGTATCCGTTGCCGG
CGGCGGCGCGACCCAGTGGGCAACAGGGAATCCTTTATCGGCTTGGCAGGCGAATTCGGTACGCTGCGCGCCGGTC
GCGTTGCGAATCAGTTTGACGATGCCAGCCAAGCCATTGATCCTTGGGACAGCAATAATGATGTGGCTTCGCAATTG
GGTATTTTCAAACGCCACGACGACATGCCGGTTTCCGTACGCTACGATTCCCCCGAATTTTCCGGTTTCAGCGGCAG
CGTTCAATTCGTTCCGATCCAAAACAGCAAGTCCGCCTATACGCCGGCTAAACGCAATACCGGCATCGGCAACTACA
CTCAAATTAATCCGGCTGTTGTCGGCAAGCCCGGATCGGATGTGTATTATGCCGGTCTGAATTACAAAAATGGCGGT
TTTGCCGGGAACTATGCCTTTAAATATGCGAGACACGCCAATGTCGGACGTAATGCTTTTGAGTTGTTCTTGATCGG
CAGCGGGAGTGATCAAGCCAAAGGTACCGATCCCTTGAAAAACCATCAGGTACACCGTCTGACGGGCGGCTATGAGG
AAGGCGGCTTGAATCTCGCCTTGGCGGCTCAGTTGGATTTGTCTGAAAATGGCGACAAAACCAAAAACAGTACGACC
GAAATTGCCGCCACTGCTTCCTACCGCTTCGGTAATGCAGTTCCACGCATCAGCTATGCCCATGGTTTCGACTTTAT
CGAACGCGGTAAAAAAGGCGAAAATACCAGCTACGATCAAATCATCGCCGGCGTTGATTATGATTTTCCAAACGCA
CTTCCGCCATCGTGTCTGGCGCTTGGCTGAAACGCAATACCGGCATCGGCAACTACACTCAAATTAATGCCGCCTCC
GTCGGTTTGCGCCACAAATTCTAA

AA seq pVR2-8
MRKKLTALVLSALPLAAVADVSLYGEIKAGVEGRNYQLQLTEAQAANGGASGQVKVTKVTKAKSRIRTKISDFGSFI
GFKGSEDLGDGLKAVWQLEQDVSVAGGGATQWGNRESFIGLAGEFGTLRAGRVANQFDDASQAIDPWDSNNDVASQL
GIFKRHDDMPVSVRYDSPEFSGFSGSVQFVPIQNSKSAYTPAKRNTGIGNYTQINPAVVGKPGSDVYYAGLNYKNGG
FAGNYAFKYARHANVGRNAFELFLIGSGSDQAKGTDPLKNHQVHRLTGGYEEGGLNLALAAQLDLSENGDKTKNSTT
EIAATASYRFGNAVPRISYAHGFDFIERGKKGENTSYDQIIAGVDYDFSKRTSAIVSGAWLKRNTGIGNYTQINAAS
VGLRHKF*

FIGURE 2A cont'd

DNA seq pΔVR1VR2-7
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTTTCGACTTTATCGA
ACGCGGTAAAAAGGCGAAAATACCAGCCCGGCTGTTGTCGGCAAGCCCGGATCGGATGTGTATTATGCCGGTCTGA
ATTACAAAAATGGCGGTTTTGCCGGGAACTATGCCTTTAAATATGCGAGACACGCCAATGTCGGACGTAATGCTTCT
GAGTTGTTCTTGATCGGCAGCGGGAGTGATCAAGCCAAAGGTACCGATCCCTTGAAAAACCATCAGGTACACCGTCT
GACGGGCGGCTATGAGGAAGGCGGCTTGAATCTCGCCTTGGCGGCTCAGTTGGATTTGTCTGAAAACGGCGACAAAA
CCAAAAACAGTACGACCGAAATTGCCGCCACTGCTTCCTACCGCTTCGGTAATGCAGTTCCACGCATCAGCTATGCC
CATGGTTTCGACTTTATCGAACGCGGTAAAAAGGCGAAAATACCAGCTACGATCAAATCATCGCCGGCGTTGATTA
TGATTTTTCCAAACGCACTTCCGCCATCGTGTCTGGCGCTTGGCTGAAACGCAATACCGGCATCGGCAACTACACTC
AAATTAACGCCGCCTCCGTCGGTTTGCGCCACAAATTCTAA

AA seq pΔVR1VR2-7
MRKKLTALVLSALPLAAVADVSLYGEIKAGVEGRNYQLQLTESRIRTKISDFGSFIGFKGSEDLGDGLKAVWQLEQD
VSVAGGGATQWGNRESFIGLAGEFGTLRAGRVANQFDDASQAIDPWDSNNDVASQLGIFKRHDDMPVSVRYDSPEFS
GFSGSVQFVPIQNSKSAYTPAFDFIERGKKGENTSPAVVGKPGSDVYYAGLNYKNGGFAGNYAFKYARHANVGRNAS
ELFLIGSGSDQAKGTDPLKNHQVHRLTGGYEEGGLNLALAAQLDLSENGDKTKNSTTEIAATASYRFGNAVPRISYA
HGFDFIERGKKGENTSYDQIIAGVDYDFSKRTSAIVSGAWLKRNTGIGNYTQINAASVGLRHKF*

DNA seq pΔVR1VR2-8
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTAAACGCAATACCGG
CATCGGCAACTACACTCAAATTAATCCGGCTGTTGTCGGCAAGCCCGGATCGGATGTGTATTATGCCGGTCTGAATT
ACAAAAATGGCGGTTTTGCCGGGAACTATGCCTTTAAATATGCGAGACACGCCAATGTCGGACGTAATGCTTTTGAG
TTGTTCTTGATCGGCAGCGGGAGTGATCAAGCCAAAGGTACCGATCCCTTGAAAAACCATCAGGTACACCGTCTGAC
GGGCGGCTATGAGGAAGGCGGCTTGAATCTCGCCTTGGCGGCTCAGTTGGATTTGTCTGAAAATGGCGACAAAACCA
AAAACAGTACGACCGAAATTGCCGCCACTGCTTCCTACCGCTTCGGTAATGCAGTTCCACGCATCAGCTATGCCCAT
GGTTTCGACTTTATCGAACGCGGTAAAAAGGCGAAAATACCAGCTACGATCAAATCATCGCCGGCGTTGATTATGA
TTTTTCCAAACGCACTTCCGCCATCGTGTCTGGCGCTTGGCTGAAACGCAATACCGGCATCGGCAACTACACTCAAA
TTAATGCCGCCTCCGTCGGTTTGCGCCACAAATTCTAA

AA seq pΔVR1VR2-8
MRKKLTALVLSALPLAAVADVSLYGEIKAGVEGRNYQLQLTESRIRTKISDFGSFIGFKGSEDLGDGLKAVWQLEQD
VSVAGGGATQWGNRESFIGLAGEFGTLRAGRVANQFDDASQAIDPWDSNNDVASQLGIFKRHDDMPVSVRYDSPEFS
GFSGSVQFVPIQNSKSAYTPAKRNTGIGNYTQINPAVVGKPGSDVYYAGLNYKNGGFAGNYAFKYARHANVGRNAFE
LFLIGSGSDQAKGTDPLKNHQVHRLTGGYEEGGLNLALAAQLDLSENGDKTKNSTTEIAATASYRFGNAVPRISYAH
GFDFIERGKKGENTSYDQIIAGVDYDFSKRTSAIVSGAWLKRNTGIGNYTQINAASVGLRHKF*

FIGURE 2A cont'd

DNA seq pVR1-7VR2-8
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAATTCGACTTTATCGAACGCGGTAAAAAAG
GCGAAAATACCAGCAGCCGCATCAGGACGAAAATCAGTGATTTCGGCTCGTTTATCGGCTTTAAGGGAGTGAGGAT
TTGGGCGACGGGCTGAAGGCTGTTTGGCAGCTTGAGCAAGACGTATCCGTTGCCGGCGGCGGCGCGACCCAGTGGGG
CAACAGGGAATCCTTTATCGGCTTGGCAGGCGAATTCGGTACGCTGCGCGCCGGTCGCGTTGCGAATCAGTTTGACG
ATGCCAGCCAAGCCATTGATCCTTGGGACAGCAATAATGATGTGGCTTCGCAATTGGGTATTTTCAAACGCCACGAC
GACATGCCGGTTTCCGTACGCTACGATTCCCCCGAATTTTCCGGTTTCAGCGGCAGCGTTCAATTCGTTCCGATCCA
AAACAGCAAGTCCGCCTATACGCCGGCTAAACGCAATACCGGCATCGGCAACTACACTCAAATTAATCCGGCTGTTG
TCGGCAAGCCCGGATCGGATGTGTATTATGCCGGTCTGAATTACAAAAATGGCGGTTTTGCCGGGAACTATGCCTTT
AAATATGCGAGACACGCCAATGTCGGACGTAATGCTTTTGAGTTGTTCTTGATCGGCAGCGGGAGTGATCAAGCCAA
AGGTACCGATCCCTTGAAAAACCATCAGGTACACCGTCTGACGGGCGGCTATGAGGAAGGCGGCTTGAATCTCGCCT
TGGCGGCTCAGTTGGATTTGTCTGAAAATGGCGACAAAACCAAAAACAGTACGACCGAAATTGCCGCCACTGCTTCC
TACCGCTTCGGTAATGCAGTTCCACGCATCAGCTATGCCCATGGTTTCGACTTTATCGAACGCGGTAAAAAAGGCGA
AAATACCAGCTACGATCAAATCATCGCCGGCGTTGATTATGATTTTTCCAAACGCACTTCCGCCATCGTGTCTGGCG
CTTGGCTGAAACGCAATACCGGCATCGGCAACTACACTCAAATTAATGCCGCCTCCGTCGGTTTGCGCCACAAATTC
TAA

AA seq pVR1-7VR2-8
MRKKLTALVLSALPLAAVADVSLYGEIKAGVEGRNYQLQLTEFDFIERGKKGENTSSRIRTKISDFGSFIGFKGSED
LGDGLKAVWQLEQDVSVAGGGATQWGNRESFIGLAGEFGTLRAGRVANQFDDASQAIDPWDSNNDVASQLGIFKRHD
DMPVSVRYDSPEFSGFSGSVQFVPIQNSKSAYTPAKRNTGIGNYTQINPAVVGKPGSDVYYAGLNYKNGGFAGNYAF
KYARHANVGRNAFELFLIGSGSDQAKGTDPLKNHQVHRLTGGYEEGGLNLALAAQLDLSENGDKTKNSTTEIAATAS
YRFGNAVPRISYAHGFDFIERGKKGENTSYDQIIAGVDYDFSKRTSAIVSGAWLKRNTGIGNYTQINAASVGLRHKF
*

DNA seq pVR1-7VR2-8Δ5
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAATTCGACTTTATCGAACGCGGTAAAAAAG
GCGAAAATACCAGCAGCCGCATCAGGACGAAAATCAGTGATTTCGGCTCGTTTATCGGCTTTAAGGGAGTGAGGAT
TTGGGCGACGGGCTGAAGGCTGTTTGGCAGCTTGAGCAAGACGTATCCGTTGCCGGCGGCGGCGCGACCCAGTGGGG
CAACAGGGAATCCTTTATCGGCTTGGCAGGCGAATTCGGTACGCTGCGCGCCGGTCGCGTTGCGAATCAGTTTGACG
ATGCCAGCCAAGCCATTGATCCTTGGGACAGCAATAATGATGTGGCTTCGCAATTGGGTATTTTCAAACGCCACGAC
GACATGCCGGTTTCCGTACGCTACGATTCCCCCGAATTTTCCGGTTTCAGCGGCAGCGTTCAATTCGTTCCGATCCA
AAACAGCAAGTCCGCCTATACGCCGGCTAAACGCAATACCGGCATCGGCAACTACACTCAAATTAATCCGGCTGTTG
TCGGCAAGCCCGGATCGGATGTGTATTATGCCGGTCTGAATTACAAAAATGGCGGTTTTGCCGGGAACTATGCCTTT
AAATATGCGAGACACGCCAATGTCGGATTGAAAAACCATCAGGTACACCGTCTGACGGGCGGCTATGAGGAAGGCGG
CTTGAATCTCGCCTTGGCGGCTCAGTTGGATTTGTCTGAAAATGGCGACAAAACCAAAAACAGTACGACCGAAATTG
CCGCCACTGCTTCCTACCGCTTCGGTAATGCAGTTCCACGCATCAGCTATGCCCATGGTTTCGACTTTATCGAACGC
GGTAAAAAAGGCGAAAATACCAGCTACGATCAAATCATCGCCGGCGTTGATTATGATTTTTCCAAACGCACTTCCGC
CATCGTGTCTGGCGCTTGGCTGAAACGCAATACCGGCATCGGCAACTACACTCAAATTAATGCCGCCTCCGTCGGTT
TGCGCCACAAATTCTAA

FIGURE 2A cont'd

AA seq pVR1-7VR2-8_5
MRKKLTALVLSALPLAAVADVSLYGEIKAGVEGRNYQLQLTEFDFIERGKKGENTSSRIRTKISDFGSFIGFKGSED
LGDGLKAVWQLEQDVSVAGGGATQWGNRESFIGLAGEFGTLRAGRVANQFDDASQAIDPWDSNNDVASQLGIFKRHD
DMPVSVRYDSPEFSGFSGSVQFVPIQNSKSAYTPAKRNTGIGNYTQINPAVVGKPGSDVYYAGLNYKNGGFAGNYAF
KYARHANVGLKNHQVHRLTGGYEEGCLNLALAAQLDLSENGDKTKNSTTEIAATASYRFGNAVPRISYAHGFDFIER
GKKGENTSYDQIIAGVDYDFSKRTSAIVSGAWLKRNTGIGNYTQINAASVGLRHKF*

DNA seq pDELVR1-2-5-6
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAGCCGCATCAGGACGAAAATCAGTGATT
TCGGCTCGTTTATCGGCTTTAAGGGGAGTGAGGATTTGGGCGACGGGCTGAAGGCTGTTTGGCAGCTTGAGCAAGAC
GTATCCGTTGCCGGCGGCGGCGCGACCCAGTGGGGCAACAGGGAATCCTTTATCGGCTTGGCAGGCGAATTCGGTAC
GCTGCGCGCCGGTCGCGTTGCGAATCAGTTTGACGATGCCAGCCAAGCCATTGATCCTTGGGACAGCAATAATGATG
TGGCTTCGCAATTGGGTATTTTCAAACGCCACGACGACATGCCGGTTTCCGTACGCTACGATTCCCCCGAATTTTCC
GGTTTCAGCGGCAGCGTTCAATTCGTTCCGATCCAAAACAGCAAGTCCGCCTATACGCCGGCTCCGGCTGTTGTCGG
CAAGCCCGGATCGGATGTGTATTATGCCGGTCTGAATTACAAAAATGGCGGTTTTGCCGGGAACTATGCCTTTAAAT
ATGCGAGACACGCCAATGTCGGATTGAAAAACCATCAGGTACACCGTCTGACGGGCGGCTATGAGGAAGGCGGCTTG
AATCTCGCCTTGGCGGCTCAGTTGGATTTGTCTAGTACGACCGAAATTGCCGCCACTGCTTCCTACCGCTTCGGTAA
TGCAGTTCCACGCATCAGCTATGCCCATGGTTTCGACTTTATCGAACGCGGTAAAAAAGGCGAAAATACCAGCTACG
ATCAAATCATCGCCGGCGTTGATTATGATTTTTCCAAACGCACTTCCGCCATCGTGTCTGGCGCTTGGCTGAAACGC
AATACCGGCATCGGCAACTACACTCAAATTAATGCCGCCTCCGTCGGTTTGCGCCACAAATTCTAA

AA seq pDELVR1-2-5-6
MRKKLTALVLSALPLAAVADVSLYGEIKAGVEGRNYQLQLTESRIRTKISDFGSFIGFKGSEDLGDGLKAVWQLEQD
VSVAGGGATQWGNRESFIGLAGEFGTLRAGRVANQFDDASQAIDPWDSNNDVASQLGIFKRHDDMPVSVRYDSPEFS
GFSGSVQFVPIQNSKSAYTPAPAVVGKPGSDVYYAGLNYKNGGFAGNYAFKYARHANVGLKNHQVHRLTGGYEEGGL
NLALAAQLDLSSTTEIAATASYRFGNAVPRISYAHGFDFIERGKKGENTSYDQIIAGVDYDFSKRTSAIVSGAWLKR
NTGIGNYTQINAASVGLRHKF*

DNA seq pPOR7in1
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGTTCG
ACTTTATCGAACGCGGTAAAAAAGGCGAAAATACCAGCAGCGGTCAGGTAAAAGTTACTAAAGTTACTAAGGCCAAA
AGCCGCATCAGGACGAAAATCAGTGATTTCGGCTCGTTTATCGGCTTTAAGGGGAGTGAGGATTTGGGCGACGGGCT
GAAGGCTGTTTGGCAGCTTGAGCAAGACGTATCCGTTGCCGGCGGCGGCGCCGACCCAGTGGGGCAACAGGGAATCCT
TTATCGGCTTGGCAGGCGAATTCGGTACGCTGCGCGCCGGTCGCGTTGCGAATCAGTTTGACGATGCCAGCCAAGCC
ATTGATCCTTGGGACAGCAATAATGATGTGGCTTCGCAATTGGGTATTTTCAAACGCCACGACGACATGCCGGTTTC
CGTACGCTACGATTCCCCCGAATTTTCCGGTTTCAGCGGCAGCGTTCAATTCGTTCCGATCCAAAACAGCAAGTCCG
CCTATACGCCGCTTATTATACTAAGAATACAAACAATAATCTTACTCTCGTTCCGTGTTGTCGGCAAGCCCGGA
TCGGATGTGTATTATGCCGGTCTGAATTACAAAAATGGCGGTTTTGCCGGGAACTATGCCTTTAAATATGCGAGACA
CGCCAATGTCGGACGTAATGCTTTTGAGTTGTTCTTGATCGGCAGCGGGAGTGATCAAGCCAAAGGTACCGATCCCT
TGAAAAACCATCAGGTACACCGTCTGACGGGCGGCTATGAGGAAGGCGGCTTGAATCTCGCCTTGGCGGCTCAGTTG
GATTTGTCTGAAAATGGCGACAAAACCAAAAACAGTACGACCGAAATTGCCGCCACTGCTTCCTACCGCTTCGGTAA
TGCAGTTCCACGCATCAGCTATGCCCATGGTTTCGACTTTATCGAACGCGGTAAAAAAGGCGAAAATACCAGCTACG
ATCAAATCATCGCCGGCGTTGATTATGATTTTTCCAAACGCACTTCCGCCATCGTGTCTGGCGCTTGGCTGAAACGC
AATACCGGCATCGGCAACTACACTCAAATTAATGCCGCCTCCGTCGGTTTGCGCCACAAATTCTAA

FIGURE 2A cont'd

AA seq pPOR7in1
MRKKLTALVLSALPLAAVADVSLYGEIKAGVEGRNYQLQLTEAQAANGGAFDFIERGKKGENTSSGQVKVTKVTKAK
SRIRTKISDFGSFIGFKGSEDLGDGLKAVWQLEQDVSVAGGGATQWGNRESFIGLAGEFGTLRAGRVANQFDDASQA
IDPWDSNNDVASQLGIFKRHDDMPVSVRYDSPEFSGFSGSVQFVPIQNSKSAYTPAYYTKNTNNNLTLVPAVVGKPG
SDVYYAGLNYKNGGFAGNYAFKYARHANVGRNAFELFLIGSGSDQAKGTDPLKNHQVHRLTGGYEEGGLNLALAAQL
DLSENGDKTKNSTTEIAATASYRFGNAVPRISYAHGFDFIERGKKGENTSYDQIIAGVDYDFSKRTSAIVSGAWLKR
NTGIGNYTQINAASVGLRHKF*

DNA seq pPOR8in4
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGAGCG
GTCAGGTAAAAGTTACTAAAGTTACTAAGGCCAAAAGCCGCATCAGGACGAAAATCAGTGATTTCGGCTCGTTTATC
GGCTTTAAGGGGAGTGAGGATTTGGGCGACGGGCTGAAGGCTGTTTGGCAGCTTGAGCAAGACGTATCCGTTGCCGG
CGGCGGCGCGACCCAGTGGGGCAACAGGGAATCCTTTATCGGCTTGGCAGGCGAATTCGGTACGCTGCGCGCCGGTC
GCGTTGCGAATCAGTTTGACGATGCCAGCCAAGCCATTGATCCTTGGGACAGCAATAATGATGTGGCTTCGCAATTG
GGTATTTTCAAACGCCACGACGACATGCCGGTTTCCGTACGCTACGATTCCCCGAATTTTCCGGTTTCAGCGGCAG
CGTTCAATTCGTTCCGATCCAAAACAGCAAGTCCGCCTATACGCCGGCTTATTATACTAAGAATACAAACAAACGCA
ATACCGGCATCGGCAACTACACTCAAATTAATAATAATCTTACTCTCGTTCCGGCTGTTGTCGGCAAGCCCGGATCG
GATGTGTATTATGCCGGTCTGAATTACAAAAATGGCGGTTTTGCCGGGAACTATGCCTTTAAATATGCGAGACACGC
CAATGTCGGACGTAATGCTTTTGAGTTGTTCTTGATCGGCAGCGGGAGTGATCAAGCCAAAGGTACCGATCCCTTGA
AAAACCATCAGGTACACCGTCTGACGGGCGGCTATGAGGAAGGCGGCTTGAATCTCGCCTTGGCGGCTCAGTTGGAT
TTGTCTGAAAATGGCGACAAAACCAAAAACAGTACGACCGAAATTGCCGCCACTGCTTCCTACCGCTTCGGTAATGC
AGTTCCACGCATCAGCTATGCCCATGGTTTCGACTTTATCGAACGCGGTAAAAAAGGCGAAAATACCAGCTACGATC
AAATCATCGCCGGCGTTGATTATGATTTTTCCAAACGCACTTCCGCCATCGTGTCTGGCGCTTGGCTGAAACGCAAT
ACCGGCATCGGCAACTACACTCAAATTAATGCCGCCTCCGTCGGTTTGCGCCACAAATTCTAA

AA seq pPor8in4
MRKKLTALVLSALPLAAVADVSLYGEIKAGVEGRNYQLQLTEAQAANGGASGQVKVTKVTKAKSRIRTKISDFGSFI
GFKGSEDLGDGLKAVWQLEQDVSVAGGGATQWGNRESFIGLAGEFGTLRAGRVANQFDDASQAIDPWDSNNDVASQL
GIFKRHDDMPVSVRYDSPEFSGFSGSVQFVPIQNSKSAYTPAYYTKNTNKRNTGIGNYTQINNNLTLVPAVVGKPGS
DVYYAGLNYKNGGFAGNYAFKYARHANVGRNAFELFLIGSGSDQAKGTDPLKNHQVHRLTGGYEEGGLNLALAAQLD
LSENGDKTKNSTTEIAATASYRFGNAVPRISYAHGFDFIERGKKGENTSYDQIIAGVDYDFSKRTSAIVSGAWLKRN
TGIGNYTQINAASVGLRHKF*

FIGURE 2A cont'd

DNA seq pPor7in1-8in4
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAGCACAAGCCGCTAACGGTGGAGCGTTCG
ACTTTATCGAACGCGGTAAAAAAGGCGAAAATACCAGCAGCGGTCAGGTAAAAGTTACTAAAGTTACTAAGGCCAAA
AGCCGCATCAGGACGAAAATCAGTGATTTCGGCTCGTTTATCGGCTTTAAGGGGAGTGAGGATTTGGGCGACGGGCT
GAAGGCTGTTTGGCAGCTTGAGCAAGACGTATCCGTTGCCGGCGGCGGCGCGACCCAGTGGGGCAACAGGGAATCCT
TTATCGGCTTGGCAGGCGAATTCGGTACGCTGCGCGCCGGTCGCGTTGCGAATCAGTTTGACGATGCCAGCCAAGCC
ATTGATCCTTGGGACAGCAATAATGATGTGGCTTCGCAATTGGGTATTTTCAAACGCCACGACGACATGCCGGTTTC
CGTACGCTACGATTCCCCCGAATTTTCCGGTTTCAGCGGCAGCGTTCAATTCGTTCCGATCCAAAACAGCAAGTCCG
CCTATACGCCGGCTTATTATACTAAGAATACAAACAAACGCAATACCGGCATCGGCAACTACACTCAAATTAATAAT
AATCTTACTCTCGTTCCGGCTGTTGTCGGCAAGCCCGGATCGGATGTGTATTATGCCGGTCTGAATTACAAAAATGG
CGGTTTTGCCGGGAACTATGCCTTTAAATATGCGAGACACGCCAATGTCGGACGTAATGCTTTTGAGTTGTTCTTGA
TCGGCAGCGGGAGTGATCAAGCCAAAGGTACCGATCCCTTGAAAAACCATCAGGTACACCGTCTGACGGGCGGCTAT
GAGGAAGGCGGCTTGAATCTCGCCTTGGCGGCTCAGTTGGATTTGTCTGAAAATGGCGACAAAACCAAAAACAGTAC
GACCGAAATTGCCGCCACTGCTTCCTACCGCTTCGGTAATGCAGTTCCACGCATCAGCTATGCCCATGGTTTCGACT
TTATCGAACGCGGTAAAAAAGGCGAAAATACCAGCTACGATCAAATCATCGCCGGCGTTGATTATGATTTTTCCAAA
CGCACTTCCGCCATCGTGTCTGGCGCTTGGCTGAAACGCAATACCGGCATCGGCAACTACACTCAAATTAATGCCGC
CTCCGTCGGTTTGCGCCACAAATTCTAA

AA seq pPor71in-8in4
MRKKLTALVLSALPLAAVADVSLYGEIKAGVEGRNYQLQLTEAQAANGGAFDFIERGKKGENTSSGQVKVTKVTKAK
SRIRTKISDFGSFIGFKGSEDLGDGLKAVWQLEQDVSVAGGGATQWGNRESFIGLAGEFGTLRAGRVANQFDDASQA
IDPWDSNNDVASQLGIFKRHDDMPVSVRYDSPEFSGFSGSVQFVPIQNSKSAYTPAYYTKNTNKRNTGIGNYTQINN
NLTLVPAVVGKPGSDVYYAGLNYKNGGFAGNYAFKYARHANVGRNAFELFLIGSGSDQAKGTDPLKNHQVHRLTGGY
EEGGLNLALAAQLDLSENGDKTKNSTTEIAATASYRFGNAVPRISYAHGFDFIERGKKGENTSYDQIIAGVDYDFSK
RTSAIVSGAWLKRNTGIGNYTQINAASVGLRHKF*

FIGURE 2A cont'd

DNA seq pVR1-7VR2-7
ATATGCGAAAAAAACTTACCGCCCTCGTATTGTCCGCACTGCCGCTTGCGGCCGTTGCCGATGTCAGCCTATACGGC
GAAATCAAAGCCGGCGTGGAAGGCAGGAACTACCAGCTGCAATTGACTGAATTCGACTTTATCGAACGCGGTAAAAA
AGGCGAAAATACCAGCAGCCGCATCAGGACGAAAATCAGTGATTTCGGCTCGTTTATCGGCTTTAAGGGGAGTGAGG
ATTTGGGCGACGGGCTGAAGGCTGTTTGGCAGCTTGAGCAAGACGTATCCGTTGCCGGCGGCGGCGCGACCCAGTGG
GGCAACAGGGAATCCTTTATCGGCTTGGCAGGCGAATTCGGTACGCTGCGCGCCGGTCGCGTTGCGAATCAGTTTGA
CGATGCCAGCCAAGCCATTGATCCTTGGGACAGCAATAATGATGTGGCTTCGCAATTGGGTATTTTCAAACGCCACG
ACGACATGCCGGTTTCCGTACGCTACGATTCCCCCGAATTTTCCGGTTTCAGCGGCAGCGTTCAATTCGTTCCGATC
CAAAACAGCAAGTCCGCCTATACGCCGGCTTTCGACTTTATCGAACGCGGTAAAAAAGGCGAAAATACCAGCCCGGC
TGTTGTCGGCAAGCCCGGATCGGATGTGTATTATGCCGGTCTGAATTACAAAAATGGCGGTTTTGCCGGGAACTATG
CCTTTAAATATGCGAGACACGCCAATGTCGGACGTAATGCTTTTGAGTTGTTCTTGATCGGCAGCGGGAGTGATCAA
GCCAAAGGTACCGATCCCTTGAAAAACCATCAGGTACACCGTCTGACGGGCGGCTATGAGGAAGGCGGCTTGAATCT
CGCCTTGGCGGCTCAGTTGGATTTGTCTGAAAATGGCGACAAAACCAAAAACAGTACGACCGAAATTGCCGCCACTG
CTTCCTACCGCTTCGGTAATGCAGTTCCACGCATCAGCTATGCCCATGGTTTCGACTTTATCGAACGCGGTAAAAAA
GGCGAAAATACCAGCTACGATCAAATCATCGCCGGCGTTGATTATGATTTTTCCAAACGCACTTCCGCCATCGTGTC
TGGCGCTTGGCTGAAACGCAATACCGGCATCGGCAACTACACTCAAATTAATGCCGCCTCCGTCGGTTTGCGCCACA
AATTCTAA

AA seq pVR1-7VR2-7
MRKKLTALVLSALPLAAVADVSLYGEIKAGVEGRNYQLQLTEFDFIERGKKGENTSSRIRTKISDFGSFIGFKGSED
LGDGLKAVWQLEQDVSVAGGGATQWGNRESFIGLAGEFGTLRAGRVANQFDDASQAIDPWDSNNDVASQLGIFKRHD
DMPVSVRYDSPEFSGFSGSVQFVPIQNSKSAYTPAFDFIERGKKGENTSPAVVGKPGSDVYYAGLNYKNGGFAGNYA
FKYARHANVGRNAFELFLIGSGSDQAKGTDPLKNHQVHRLTGYEEGGLNLALAAQLDLSENGDKTKNSTTEIAATA
SYRFGNAVPRISYAHGFDFIERGKKGENTSYDQIIAGVDYDFSKRTSAIVSGAWLKRNTGIGNYTQINAASVGLRHK
F*

DNA seq pVR1-8VR2-8
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAAACGCAATACCGGCATCGGCAACTACA
CTCAAATTAATAGCCGCATCAGGACGAAAATCAGTGATTTCGGCTCGTTTATCGGCTTTAAGGGGAGTGAGGATTTG
GGCGACGGGCTGAAGGCTGTTTGGCAGCTTGAGCAAGACGTATCCGTTGCCGGCGGCGGCGCGACCCAGTGGGGCAA
CAGGGAATCCTTTATCGGCTTGGCAGGCGAATTCGGTACGCTGCGCGCCGGTCGCGTTGCGAATCAGTTTGACGATG
CCAGCCAAGCCATTGATCCTTGGGACAGCAATAATGATGTGGCTTCGCAATTGGGTATTTTCAAACGCCACGACGAC
ATGCCGGTTTCCGTACGCTACGATTCCCCCGAATTTTCCGGTTTCAGCGGCAGCGTTCAATTCGTTCCGATCCAAAA
CAGCAAGTCCGCCTATACGCCGGCTAAACGCAATACCGGCATCGGCAACTACACTCAAATTAATCCGGCTGTTGTCG
GCAAGCCCGGATCGGATGTGTATTATGCCGGTCTGAATTACAAAAATGGCGGTTTTGCCGGGAACTATGCCTTTAAA
TATGCGAGACACGCCAATGTCGGACGTAATGCTTTTGAGTTGTTCTTGATCGGCAGCGGGAGTGATCAAGCCAAAGG
TACCGATCCCTTGAAAAACCATCAGGTACACCGTCTGACGGGCGGCTATGAGGAAGGCGGCTTGAATCTCGCCTTGG
CGGCTCAGTTGGATTTGTCTGAAAATGGCGACAAAACCAAAAACAGTACGACCGAAATTGCCGCCACTGCTTCCTAC
CGCTTCGGTAATGCAGTTCCACGCATCAGCTATGCCCATGGTTTCGACTTTATCGAACGCGGTAAAAAAGGCGAAAA
TACCAGCTACGATCAAATCATCGCCGGCGTTGATTATGATTTTTCCAAACGCACTTCCGCCATCGTGTCTGGCGCTT
GGCTGAAACGCAATACCGGCATCGGCAACTACACTCAAATTAATGCCGCCTCCGTCGGTTTGCGCCACAAATTCTAA VR18VR28
MRKKLTALVLSALPLAAVADVSLYGEIKAGVEGRNYQLQLTEKRNTGIGNYTQINSRIRTKISDFGSFIGFKGSEDL
GDGLKAVWQLEQDVSVAGGGATQWGNRESFIGLAGEFGTLRAGRVANQFDDASQAIDPWDSNNDVASQLGIFKRHDD
MPVSVRYDSPEFSGFSGSVQFVPIQNSKSAYTPAKRNTGIGNYTQINPAVVGKPGSDVYYAGLNYKNGGFAGNYAFK
YARHANVGRNAFELFLIGSGSDQAKGTDPLKNHQVHRLTGYEEGGLNLALAAQLDLSENGDKTKNSTTEIAATASY
RFGNAVPRISYAHGFDFIERGKKGENTSYDQIIAGVDYDFSKRTSAIVSGAWLKRNTGIGNYTQINAASVGLRHKF

FIGURE 2B

DNA seq pVR1-8VR2-7
ATGCGAAAAAAACTTACCGCCCTCGTATTGTCCGCACTGCCGCTTGCGGCCGTTGCCGATGTCAGCCTATACGGCGA
AATCAAAGCCGGCGTGGAAGGCAGGAACTACCAGCTGCAATTGACTGAAAAACGCAATACCGGCATCGGCAACTACA
CTCAAATTAATAGCCGCATCAGGACGAAAATCAGTGATTTCGGCTCGTTTATCGGCTTTAAGGGGAGTGAGGATTTG
GGCGACGGGCTGAAGGCTGTTTGGCAGCTTGAGCAAAACGTATCCGTTGCCGGCGGCGGCGCGACCCAGTGGGGCAA
CAGGGAATCCTTTATCGGCTTGGCAGGCGAATTCGGTACGCTGCGCGCCGGTCGCGTTGCGAATCAGTTTGACGATG
CCAGCCAAGCCATTGATCCTTGGGACAGCAATAATGATGTGGCTTCGCAATTGGGTATTTTCAAACGCCACGACGAC
ATGCCGGTTTCCGTACGCTACGATTCCCCCGAATTTTCCGGTTTCAGCGGCAGCGTTCAATTCGTTCCGATCCAAAA
CAGCAAGTCCGCCTATACGCCGGCTTTCGACTTTATCGAACGCGGTAAAAAAGGCGAAAATACCAGCCCGGCTGTTG
TCGGCAAGCCCGGATCGGATGTGTATTATGCCGGTCTGAATTACAAAAATGGCGGTTTTGCCGGGAACTATGCCTTT
AAATATGCGAGACACGCCAATGTCGGACGTAATGCTTTTGAGTTGTTCTTGATCGGCAGCGGGAGTGATCAAGCCAA
AGGTACCGATCCCTTGAAAAACCATCAGGTACACCGTCTGACGGGCGGCTATGAGGAAGGCGGCTTGAATCTCGCCT
TGGCGGCTCAGTTGGATTTGTCTGAAAATGGCGACAAAACCAAAAACAGTACGACCGAAATTGCCGCCACTGCTTCC
TACCGCTTCGGTAATGCAGTTCCACGCATCAGCTATGCCCATGGTTTCGACTTTATCGAACGCGGTAAAAAAGGCGA
AAATACCAGCTACGATCAAATCATCGCCGGCGTTGATTATGATTTTTCCAAACGCACTTCCGCCATCGTGTCTGGCG
CTTGGCTGAAACGCAATACCGGCATCGGCAACTACACTCAAATTAATGCCGCCTCCGTCGGTTTGCGCCACAAATTC
TAA

AA seq pVR1-8VR2-7
MRKKLTALVLSALPLAAVADVSLYGEIKAGVEGRNYQLQLTEKRNTGIGNYTQINSRIRTKISDFGSFIGFKGSEDL
GDGLKAVWQLEQNVSVAGGGATQWGNRESFIGLAGEFGTLRAGRVANQFDDASQAIDPWDSNNDVASQLGIFKRHDD
MPVSVRYDSPEFSGFSGSVQFVPIQNSKSAYTPAFDFIERGKKGENTSPAVVGKPGSDVYYAGLNYKNGGFAGNYAF
KYARHANVGRNAFELFLIGSGSDQAKGTDPLKNHQVHRLTGGYEEGGLNLALAAQLDLSENGDKTKNSTTEIAATAS
YRFGNAVPRISYAHGFDFIERGKKGENTSYDQIIAGVDYDFSKRTSAIVSGAWLKRNTGIGNYTQINAASVGLRHKF

FIGURE 2B cont'd

```
MC58 1_7 16-2      1 EGRNYQLQLTEAQAANGGASGQVKVTKVTKAKSRIRTKISDFGSFIGFKG  50
M990 1_18 25       1 EGNNIQLQLTEPPSKG------QTGNKVTKGKSRIRTKINDFGSFIGFKG  44
2996 1_5-1 2-2     1 EGRNIQLQLTEPLQN-------IQQPQVTKRKSRIRTKISDFGSFIGFKG  43
                     ** * ******            .*** ******** **********

MC58 1_7 16-2     51 SEDLGDGLKAVWQLEQDVSVAGGGATQWGNRESFIGLAGEFGTLRAGRVA 100
M990 1_18 25      45 SEDLGEGLKAVWQLEQDVSVAGGGATQWGNRESFIGLAGEFGTLRAGRVA  94
2996 1_5-1 2-2    44 SEDLGEGLKAVWQLEQDVSVAGGGATRWGNRESFVGLAGEFGTLRAGRVA  93
                     *****.******************** ******.*****************

MC58 1_7 16-2    101 NQFDDASQAIDPWDSNNDVASQLGIFKRHDDMPVSVRYDSPEFSGFSGSV 150
M990 1_18 25      95 NQFDDASQAIDPWDSNNDVASQLGIFKRHDDMPVSVRYDSPDFSGFSGSV 144
2996 1_5-1 2-2    94 NQFDDASKAIDPWDSNNVVASQLGIFKRHDDMPVSVRYDSPEFSGFSGSV 143
                     *******.********* **********************.********

MC58 1_7 16-2    151 QFVPIQNSKSAYTPAYYTKNTNNN-LTLVPAVVGKPGSDVYYAGLNYKNG 199
M990 1_18 25     145 QFVPAQNSKSAYTPATYTVDSSGV-VTPVPAVVGKPGSDVYYAGLNYKNG 193
2996 1_5-1 2-2   144 QFVPAQNSKSAYTPAHFVQQTPQSQPTLVPAVVGKPGSDVYYAGLNYKNG 193
                     **** **********  .   .   * *********************

MC58 1_7 16-2    200 GFAGNYAFKYARHANVGRNAFELFLIG--SGSDQAKGTDPLKNHQVHRLT 247
M990 1_18 25     194 GFAGNYAFKYAKHANVGRDAFNLFLLGRIGEGDEAKGTDPLKNHQVHRLT 243
2996 1_5-1 2-2   194 GFAGNYAFKYAKHANVGRDAFELFLLG--SGSDEAKGTDPLKNHQVHRLT 241
                     **********.****** ** *** *      .*****************

MC58 1_7 16-2    248 GGYEEGGLNLALAAQLDLSENGDKTKNSTTEIAATASYRFGNAVPRISYA 297
M990 1_18 25     244 GGYEEGGLNLALAAQLDLSENGDKTKNSTTEIAATASYRFGNAVPRISYA 293
2996 1_5-1 2-2   242 GGYEEGGLNLALAAQLDLSENADKTKNSTTEIAATASYRFGNAVPRISYA 291
                     ********************* ****************************

MC58 1_7 16-2    298 HGFDFIERGKKGENTSYDQIIAGVDYDFSKRTSAIVSGAWLKRNTGIGNY 347
M990 1_18 25     294 HCFDFIERGKKGEHTSYDQIIAGVDYDFSKRTSAIVSGAWLKRNTGIGNY 343
2996 1_5-1 2-2   292 HGFDFIERGKKGENTSYDQIIAGVDYDFSKRTSAIVSGAWLKRNTGIGNY 341
                     * ********** .***********************************

MC58 1_7 16-2    348 TQINAASVGLRHKF 361
M990 1_18 25     344 TQINAAS------- 35
2996 1_5-1 2-2   342 TQINAASVGLRHKF 355
                     *******
```

FIGURE 3A

FIGURE 3B

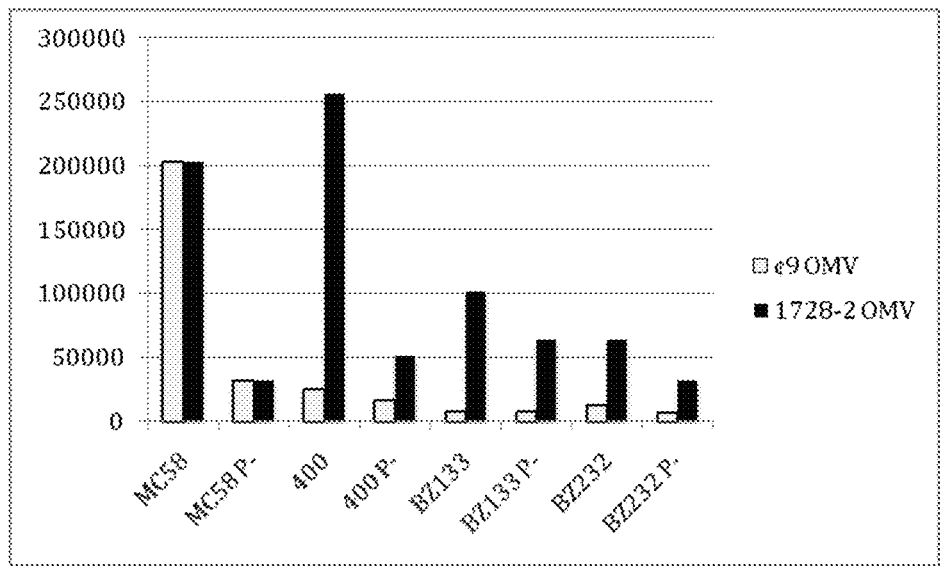
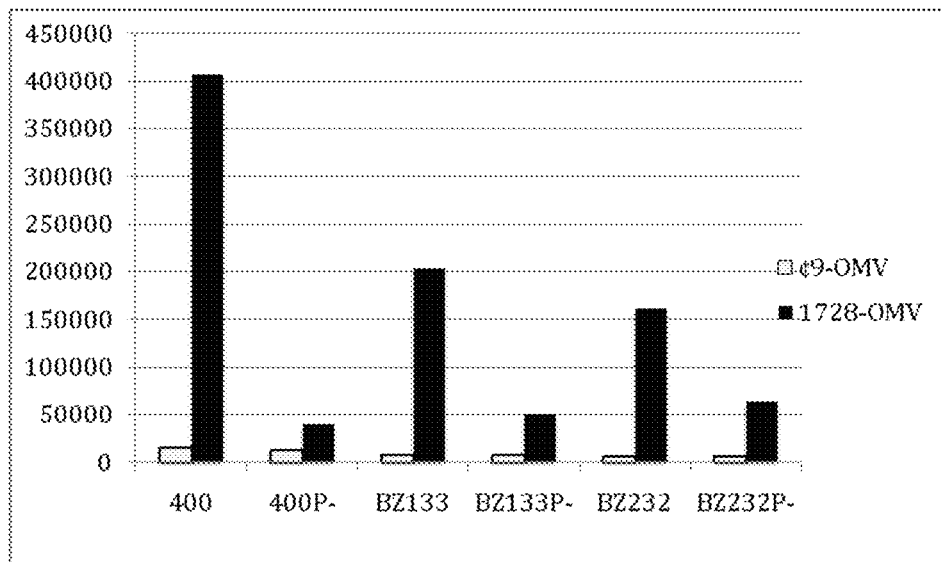
FIGURE 6 under 35 U.S.C. §371 of International Application Serial No. PCT/AU2011/000971, filed Aug. 1, 2011, which claims benefit of priority under 35 U.S.C. §119 to Australian Provisional Patent Application Serial No. AU 2010903418, filed on Jul. 30, 2010, the contents of each which are hereby incorporated by reference in their entirety.

SEQUENCE LISTING

<160> NUMBER OF SEQ ID NOS: 93

<210> SEQ ID NO 1
<211> LENGTH: 392
<212> TYPE: PRT
<213> ORGANISM: Neisseria meningitidis

<400> SEQUENCE: 1

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
    130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Tyr Tyr Thr Lys Asn Thr Asn Asn Leu Thr Leu
        195                 200                 205

Val Pro Ala Val Val Gly Lys Pro Gly Ser Asp Val Tyr Tyr Ala Gly
    210                 215                 220

Leu Asn Tyr Lys Asn Gly Phe Ala Gly Asn Tyr Ala Phe Lys Tyr
225                 230                 235                 240

Ala Arg His Ala Asn Val Gly Arg Asn Ala Phe Glu Leu Phe Leu Ile
                245                 250                 255

Gly Ser Gly Ser Asp Gln Ala Lys Gly Thr Asp Pro Leu Lys Asn His
            260                 265                 270

Gln Val His Arg Leu Thr Gly Gly Tyr Glu Glu Gly Leu Asn Leu
        275                 280                 285

Ala Leu Ala Ala Gln Leu Asp Leu Ser Glu Asn Gly Asp Lys Thr Lys
    290                 295                 300

Asn Ser Thr Thr Glu Ile Ala Ala Thr Ala Ser Tyr Arg Phe Gly Asn
305                 310                 315                 320

Ala Val Pro Arg Ile Ser Tyr Ala His Gly Phe Asp Phe Ile Glu Arg
                325                 330                 335

Gly Lys Lys Gly Glu Asn Thr Ser Tyr Asp Gln Ile Ile Ala Gly Val
            340                 345                 350

Asp Tyr Asp Phe Ser Lys Arg Thr Ser Ala Ile Val Ser Gly Ala Trp
        355                 360                 365
```

-continued

```
Leu Lys Arg Asn Thr Gly Ile Gly Asn Tyr Thr Gln Ile Asn Ala Ala
    370                 375                 380

Ser Val Gly Leu Arg His Lys Phe
385                 390

<210> SEQ ID NO 2
<211> LENGTH: 366
<212> TYPE: PRT
<213> ORGANISM: Artificial sequence
<220> FEATURE:
<223> OTHER INFORMATION: PorA mutant

<400> SEQUENCE: 2

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Ser Arg Ile Arg Thr Lys Ile Ser Asp Phe Gly
        35                  40                  45

Ser Phe Ile Gly Phe Lys Gly Ser Glu Asp Leu Gly Asp Gly Leu Lys
    50                  55                  60

Ala Val Trp Gln Leu Glu Gln Asp Val Ser Val Ala Gly Gly Gly Ala
65                  70                  75                  80

Thr Gln Trp Gly Asn Arg Glu Ser Phe Ile Gly Leu Ala Gly Glu Phe
                85                  90                  95

Gly Thr Leu Arg Ala Gly Arg Val Ala Asn Gln Phe Asp Asp Ala Ser
            100                 105                 110

Gln Ala Ile Asp Pro Trp Asp Ser Asn Asn Asp Val Ala Ser Gln Leu
        115                 120                 125

Gly Ile Phe Lys Arg His Asp Asp Met Pro Val Ser Val Arg Tyr Asp
    130                 135                 140

Ser Pro Glu Phe Ser Gly Phe Ser Gly Ser Val Gln Phe Val Pro Ile
145                 150                 155                 160

Gln Asn Ser Lys Ser Ala Tyr Thr Pro Ala Tyr Tyr Thr Lys Asn Thr
                165                 170                 175

Asn Asn Asn Leu Thr Leu Val Pro Ala Val Val Gly Lys Pro Gly Ser
            180                 185                 190

Asp Val Tyr Tyr Ala Gly Leu Asn Tyr Lys Asn Gly Gly Phe Ala Gly
        195                 200                 205

Asn Tyr Ala Phe Lys Tyr Ala Arg His Ala Asn Val Gly Arg Asn Ala
    210                 215                 220

Phe Glu Leu Phe Leu Ile Gly Ser Gly Ser Asp Gln Ala Lys Gly Thr
225                 230                 235                 240

Asp Pro Leu Lys Asn His Gln Val His Arg Leu Thr Gly Gly Tyr Glu
                245                 250                 255

Glu Gly Gly Leu Asn Leu Ala Leu Ala Ala Gln Leu Asp Leu Ser Glu
            260                 265                 270

Asn Gly Asp Lys Thr Lys Asn Ser Thr Thr Glu Ile Ala Ala Thr Ala
        275                 280                 285

Ser Tyr Arg Phe Gly Asn Ala Val Pro Arg Ile Ser Tyr Ala His Gly
    290                 295                 300

Phe Asp Phe Ile Glu Arg Gly Lys Lys Gly Glu Asn Thr Ser Tyr Asp
305                 310                 315                 320

Gln Ile Ile Ala Gly Val Asp Tyr Asp Phe Ser Lys Arg Thr Ser Ala
                325                 330                 335
```

```
Ile Val Ser Gly Ala Trp Leu Lys Arg Asn Thr Gly Ile Gly Asn Tyr
                340                 345                 350

Thr Gln Ile Asn Ala Ala Ser Val Gly Leu Arg His Lys Phe
        355                 360                 365

<210> SEQ ID NO 3
<211> LENGTH: 367
<212> TYPE: PRT
<213> ORGANISM: Artificial sequence
<220> FEATURE:
<223> OTHER INFORMATION: porA mutant

<400> SEQUENCE: 3

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Val Val Lys Pro Gly
            180                 185                 190

Ser Asp Val Tyr Tyr Ala Gly Leu Asn Tyr Lys Asn Gly Phe Ala
        195                 200                 205

Gly Asn Tyr Ala Phe Lys Tyr Ala Arg His Ala Asn Val Gly Arg Asn
    210                 215                 220

Ala Phe Glu Leu Phe Leu Ile Gly Ser Gly Ser Asp Gln Ala Lys Gly
225                 230                 235                 240

Thr Asp Pro Leu Lys Asn His Gln Val His Arg Leu Thr Gly Gly Tyr
                245                 250                 255

Glu Glu Gly Gly Leu Asn Leu Ala Leu Ala Ala Gln Leu Asp Leu Ser
            260                 265                 270

Glu Asn Gly Asp Lys Thr Lys Asn Ser Thr Thr Glu Ile Ala Ala Thr
        275                 280                 285

Ala Ser Tyr Arg Phe Gly Asn Ala Val Pro Arg Ile Ser Tyr Ala His
    290                 295                 300

Gly Phe Asp Phe Ile Glu Arg Gly Lys Lys Gly Glu Asn Thr Ser Tyr
305                 310                 315                 320

Asp Gln Ile Ile Ala Gly Val Asp Tyr Asp Phe Ser Lys Arg Thr Ser
                325                 330                 335
```

```
Ala Ile Val Ser Gly Ala Trp Leu Lys Arg Asn Thr Gly Ile Gly Asn
            340                 345                 350

Tyr Thr Gln Ile Asn Ala Ala Ser Val Gly Leu Arg His Lys Phe
        355                 360                 365
```

<210> SEQ ID NO 4
<211> LENGTH: 341
<212> TYPE: PRT
<213> ORGANISM: Artificial sequence
<220> FEATURE:
<223> OTHER INFORMATION: porA mutant

<400> SEQUENCE: 4

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Ser Arg Ile Arg Thr Lys Ile Ser Asp Phe Gly
        35                  40                  45

Ser Phe Ile Gly Phe Lys Gly Ser Glu Asp Leu Gly Asp Gly Leu Lys
    50                  55                  60

Ala Val Trp Gln Leu Glu Gln Asp Val Ser Val Ala Gly Gly Gly Ala
65                  70                  75                  80

Thr Gln Trp Gly Asn Arg Glu Ser Phe Ile Gly Leu Ala Gly Glu Phe
                85                  90                  95

Gly Thr Leu Arg Ala Gly Arg Val Ala Asn Gln Phe Asp Asp Ala Ser
            100                 105                 110

Gln Ala Ile Asp Pro Trp Asp Ser Asn Asn Asp Val Ala Ser Gln Leu
        115                 120                 125

Gly Ile Phe Lys Arg His Asp Asp Met Pro Val Ser Val Arg Tyr Asp
    130                 135                 140

Ser Pro Glu Phe Ser Gly Phe Ser Gly Ser Val Gln Phe Val Pro Ile
145                 150                 155                 160

Val Val Gly Lys Pro Gly Ser Asp Val Tyr Tyr Ala Gly Leu Asn Tyr
                165                 170                 175

Lys Asn Gly Gly Phe Ala Gly Asn Tyr Ala Phe Lys Tyr Ala Arg His
            180                 185                 190

Ala Asn Val Gly Arg Asn Ala Phe Glu Leu Phe Leu Ile Gly Ser Gly
        195                 200                 205

Ser Asp Gln Ala Lys Gly Thr Asp Pro Leu Lys Asn His Gln Val His
    210                 215                 220

Arg Leu Thr Gly Gly Tyr Glu Glu Gly Gly Leu Asn Leu Ala Leu Ala
225                 230                 235                 240

Ala Gln Leu Asp Leu Ser Glu Asn Gly Asp Lys Thr Lys Asn Ser Thr
                245                 250                 255

Thr Glu Ile Ala Ala Thr Ala Ser Tyr Arg Phe Gly Asn Ala Val Pro
            260                 265                 270

Arg Ile Ser Tyr Ala His Gly Phe Asp Phe Ile Glu Arg Gly Lys Lys
        275                 280                 285

Gly Glu Asn Thr Ser Tyr Asp Gln Ile Ile Ala Gly Val Asp Tyr Asp
    290                 295                 300

Phe Ser Lys Arg Thr Ser Ala Ile Val Ser Gly Ala Trp Leu Lys Arg
305                 310                 315                 320

Asn Thr Gly Ile Gly Asn Tyr Thr Gln Ile Asn Ala Ala Ser Val Gly
                325                 330                 335
```

-continued

Leu Arg His Lys Phe
            340

<210> SEQ ID NO 5
<211> LENGTH: 320
<212> TYPE: PRT
<213> ORGANISM: Artificial sequence
<220> FEATURE:
<223> OTHER INFORMATION: porA mutant

<400> SEQUENCE: 5

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Ser Arg Ile Arg Thr Lys Ile Ser Asp Phe Gly
        35                  40                  45

Ser Phe Ile Gly Phe Lys Gly Ser Glu Asp Leu Gly Asp Gly Leu Lys
50                  55                  60

Ala Val Trp Gln Leu Glu Gln Asp Val Ser Val Ala Gly Gly Gly Ala
65                  70                  75                  80

Thr Gln Trp Gly Asn Arg Glu Ser Phe Ile Gly Leu Ala Gly Glu Phe
                85                  90                  95

Gly Thr Leu Arg Ala Gly Arg Val Ala Asn Gln Phe Asp Asp Ala Ser
            100                 105                 110

Gln Ala Ile Asp Pro Trp Asp Ser Asn Asn Asp Val Ala Ser Gln Leu
        115                 120                 125

Gly Ile Phe Lys Arg His Asp Asp Met Pro Val Ser Val Arg Tyr Asp
130                 135                 140

Ser Pro Glu Phe Ser Gly Phe Ser Gly Ser Val Gln Phe Val Pro Ile
145                 150                 155                 160

Val Val Gly Lys Pro Gly Ser Asp Val Tyr Tyr Ala Gly Leu Asn Tyr
                165                 170                 175

Lys Asn Gly Gly Phe Ala Gly Asn Tyr Ala Phe Lys Tyr Ala Arg His
            180                 185                 190

Ala Asn Val Gly Leu Lys Asn His Gln Val His Arg Leu Thr Gly Gly
        195                 200                 205

Tyr Glu Glu Gly Gly Leu Asn Leu Ala Leu Ala Gln Leu Asp Leu
210                 215                 220

Ser Glu Asn Gly Asp Lys Thr Lys Asn Ser Thr Thr Glu Ile Ala Ala
225                 230                 235                 240

Thr Ala Ser Tyr Arg Phe Gly Asn Ala Val Pro Arg Ile Ser Tyr Ala
                245                 250                 255

His Gly Phe Asp Phe Ile Glu Arg Gly Lys Lys Gly Glu Asn Thr Ser
            260                 265                 270

Tyr Asp Gln Ile Ile Ala Gly Val Asp Tyr Asp Phe Ser Lys Arg Thr
        275                 280                 285

Ser Ala Ile Val Ser Gly Ala Trp Leu Lys Arg Asn Thr Gly Ile Gly
290                 295                 300

Asn Tyr Thr Gln Ile Asn Ala Ala Ser Val Gly Leu Arg His Lys Phe
305                 310                 315                 320

<210> SEQ ID NO 6
<211> LENGTH: 371
<212> TYPE: PRT
<213> ORGANISM: Artificial sequence
<220> FEATURE:

<223> OTHER INFORMATION: porA mutant

<400> SEQUENCE: 6

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ser Arg Ile Arg Thr Lys
        35                  40                  45

Ile Ser Asp Phe Gly Ser Phe Ile Gly Phe Lys Gly Ser Glu Asp Leu
    50                  55                  60

Gly Asp Gly Leu Lys Ala Val Trp Gln Leu Glu Gln Asp Val Ser Val
65                  70                  75                  80

Ala Gly Gly Gly Ala Thr Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asp Pro Trp Asp Ser Asn Asn Asp
        115                 120                 125

Val Ala Ser Gln Leu Gly Ile Phe Lys Arg His Asp Asp Met Pro Val
    130                 135                 140

Ser Val Arg Tyr Asp Ser Pro Glu Phe Ser Gly Phe Ser Gly Ser Val
145                 150                 155                 160

Gln Phe Val Pro Ile Gln Asn Ser Lys Ser Ala Tyr Thr Pro Ala Tyr
                165                 170                 175

Tyr Thr Lys Asn Thr Asn Asn Asn Leu Thr Leu Val Pro Ala Val Val
            180                 185                 190

Gly Lys Pro Gly Ser Asp Val Tyr Tyr Ala Gly Leu Asn Tyr Lys Asn
        195                 200                 205

Gly Gly Phe Ala Gly Asn Tyr Ala Phe Lys Tyr Ala Arg His Ala Asn
    210                 215                 220

Val Gly Arg Asn Ala Phe Glu Leu Phe Leu Ile Gly Ser Gly Ser Asp
225                 230                 235                 240

Gln Ala Lys Gly Thr Asp Pro Leu Lys Asn His Gln Val His Arg Leu
                245                 250                 255

Thr Gly Gly Tyr Glu Glu Gly Gly Leu Asn Leu Ala Leu Ala Ala Gln
            260                 265                 270

Leu Asp Leu Ser Glu Asn Gly Asp Lys Thr Lys Asn Ser Thr Thr Glu
        275                 280                 285

Ile Ala Ala Thr Ala Ser Tyr Arg Phe Gly Asn Ala Val Pro Arg Ile
    290                 295                 300

Ser Tyr Ala His Gly Phe Asp Phe Ile Glu Arg Gly Lys Lys Gly Glu
305                 310                 315                 320

Asn Thr Ser Tyr Asp Gln Ile Ile Ala Gly Val Asp Tyr Asp Phe Ser
                325                 330                 335

Lys Arg Thr Ser Ala Ile Val Ser Gly Ala Trp Leu Lys Arg Asn Thr
            340                 345                 350

Gly Ile Gly Asn Tyr Thr Gln Ile Asn Ala Ala Ser Val Gly Leu Arg
        355                 360                 365

His Lys Phe
    370
```

<210> SEQ ID NO 7
<211> LENGTH: 379

<212> TYPE: PRT
<213> ORGANISM: Artificial sequence
<220> FEATURE:
<223> OTHER INFORMATION: porA mutant

<400> SEQUENCE: 7

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Pro Ala Val Val Gly Lys Pro Gly Ser Asp Val Tyr
        195                 200                 205

Tyr Ala Gly Leu Asn Tyr Lys Asn Gly Gly Phe Ala Gly Asn Tyr Ala
    210                 215                 220

Phe Lys Tyr Ala Arg His Ala Asn Val Gly Arg Asn Ala Phe Glu Leu
225                 230                 235                 240

Phe Leu Ile Gly Ser Gly Ser Asp Gln Ala Lys Gly Thr Asp Pro Leu
                245                 250                 255

Lys Asn His Gln Val His Arg Leu Thr Gly Gly Tyr Glu Glu Gly Gly
            260                 265                 270

Leu Asn Leu Ala Leu Ala Ala Gln Leu Asp Leu Ser Glu Asn Gly Asp
        275                 280                 285

Lys Thr Lys Asn Ser Thr Thr Glu Ile Ala Ala Thr Ala Ser Tyr Arg
    290                 295                 300

Phe Gly Asn Ala Val Pro Arg Ile Ser Tyr Ala His Gly Phe Asp Phe
305                 310                 315                 320

Ile Glu Arg Gly Lys Lys Gly Glu Asn Thr Ser Tyr Asp Gln Ile Ile
                325                 330                 335

Ala Gly Val Asp Tyr Asp Phe Ser Lys Arg Thr Ser Ala Ile Val Ser
            340                 345                 350

Gly Ala Trp Leu Lys Arg Asn Thr Gly Ile Gly Asn Tyr Thr Gln Ile
        355                 360                 365

Asn Ala Ala Ser Val Gly Leu Arg His Lys Phe
    370                 375
```

```
<210> SEQ ID NO 8
<211> LENGTH: 358
<212> TYPE: PRT
<213> ORGANISM: Artificial sequence
<220> FEATURE:
<223> OTHER INFORMATION: porA mutant

<400> SEQUENCE: 8

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ser Arg Ile Arg Thr Lys
        35                  40                  45

Ile Ser Asp Phe Gly Ser Phe Ile Gly Phe Lys Gly Ser Glu Asp Leu
    50                  55                  60

Gly Asp Gly Leu Lys Ala Val Trp Gln Leu Glu Gln Asp Val Ser Val
65                  70                  75                  80

Ala Gly Gly Gly Ala Thr Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asp Pro Trp Asp Ser Asn Asn Asp
        115                 120                 125

Val Ala Ser Gln Leu Gly Ile Phe Lys Arg His Asp Asp Met Pro Val
130                 135                 140

Ser Val Arg Tyr Asp Ser Pro Glu Phe Ser Gly Phe Ser Gly Ser Val
145                 150                 155                 160

Gln Phe Val Pro Ile Gln Asn Ser Lys Ser Ala Tyr Thr Pro Ala Pro
                165                 170                 175

Ala Val Val Gly Lys Pro Gly Ser Asp Val Tyr Tyr Ala Gly Leu Asn
            180                 185                 190

Tyr Lys Asn Gly Gly Phe Ala Gly Asn Tyr Ala Phe Lys Tyr Ala Arg
        195                 200                 205

His Ala Asn Val Gly Arg Asn Ala Phe Glu Leu Phe Leu Ile Gly Ser
    210                 215                 220

Gly Ser Asp Gln Ala Lys Gly Thr Asp Pro Leu Lys Asn His Gln Val
225                 230                 235                 240

His Arg Leu Thr Gly Gly Tyr Glu Glu Gly Gly Leu Asn Leu Ala Leu
                245                 250                 255

Ala Ala Gln Leu Asp Leu Ser Glu Asn Gly Asp Lys Thr Lys Asn Ser
            260                 265                 270

Thr Thr Glu Ile Ala Ala Thr Ala Ser Tyr Arg Phe Gly Asn Ala Val
        275                 280                 285

Pro Arg Ile Ser Tyr Ala His Gly Phe Asp Phe Ile Glu Arg Gly Lys
    290                 295                 300

Lys Gly Glu Asn Thr Ser Tyr Asp Gln Ile Ala Gly Val Asp Tyr
305                 310                 315                 320

Asp Phe Ser Lys Arg Thr Ser Ala Ile Val Ser Gly Ala Trp Leu Lys
                325                 330                 335

Arg Asn Thr Gly Ile Gly Asn Tyr Thr Gln Ile Asn Ala Ala Ser Val
            340                 345                 350

Gly Leu Arg His Lys Phe
        355
```

<210> SEQ ID NO 9
<211> LENGTH: 320
<212> TYPE: PRT
<213> ORGANISM: Artificial sequence
<220> FEATURE:
<223> OTHER INFORMATION: porA mutant

<400> SEQUENCE: 9

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Ser Arg Ile Arg Thr Lys Ile Ser Asp Phe Gly
        35                  40                  45

Ser Phe Ile Gly Phe Lys Gly Ser Glu Asp Leu Gly Asp Gly Leu Lys
    50                  55                  60

Ala Val Trp Gln Leu Glu Gln Asp Val Ser Val Ala Gly Gly Gly Ala
65                  70                  75                  80

Thr Gln Trp Gly Asn Arg Glu Ser Phe Ile Gly Leu Ala Gly Glu Phe
                85                  90                  95

Gly Thr Leu Arg Ala Gly Arg Val Ala Asn Gln Phe Asp Asp Ala Ser
            100                 105                 110

Gln Ala Ile Asp Pro Trp Asp Ser Asn Asn Asp Val Ala Ser Gln Leu
        115                 120                 125

Gly Ile Phe Lys Arg His Asp Asp Met Pro Val Ser Val Arg Tyr Asp
    130                 135                 140

Ser Pro Glu Phe Ser Gly Phe Ser Gly Ser Val Gln Phe Val Pro Ile
145                 150                 155                 160

Val Val Gly Lys Pro Gly Ser Asp Val Tyr Tyr Ala Gly Leu Asn Tyr
                165                 170                 175

Lys Asn Gly Gly Phe Ala Gly Asn Tyr Ala Phe Lys Tyr Ala Arg His
            180                 185                 190

Ala Asn Val Gly Leu Lys Asn His Gln Val His Arg Leu Thr Gly Gly
        195                 200                 205

Tyr Glu Glu Gly Gly Leu Asn Leu Ala Leu Ala Ala Gln Leu Asp Leu
    210                 215                 220

Ser Glu Asn Gly Asp Lys Thr Lys Asn Ser Thr Thr Glu Ile Ala Ala
225                 230                 235                 240

Thr Ala Ser Tyr Arg Phe Gly Asn Ala Val Pro Arg Ile Ser Tyr Ala
                245                 250                 255

His Gly Phe Asp Phe Ile Glu Arg Gly Lys Lys Gly Glu Asn Thr Ser
            260                 265                 270

Tyr Asp Gln Ile Ile Ala Gly Val Asp Tyr Asp Phe Ser Lys Arg Thr
        275                 280                 285

Ser Ala Ile Val Ser Gly Ala Trp Leu Lys Arg Asn Thr Gly Ile Gly
    290                 295                 300

Asn Tyr Thr Gln Ile Asn Ala Ala Ser Val Gly Leu Arg His Lys Phe
305                 310                 315                 320
```

<210> SEQ ID NO 10
<211> LENGTH: 393
<212> TYPE: PRT
<213> ORGANISM: Artificial sequence
<220> FEATURE:
<223> OTHER INFORMATION: porA mutant

<400> SEQUENCE: 10

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
            35                  40                  45

Gly Ala Ser Gly Gln Val Lys Val Thr Lys Val Thr Lys Ala Lys Ser
50                      55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
            85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
            115                 120                 125

Arg Val Ala Asn Gln Phe Asp Asp Ala Ser Gln Ala Ile Asp Pro Trp
130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Phe Asp Phe Ile Glu Arg Gly Lys Lys Gly Glu Asn
            195                 200                 205

Thr Ser Pro Ala Val Val Gly Lys Pro Gly Ser Asp Val Tyr Tyr Ala
210                 215                 220

Gly Leu Asn Tyr Lys Asn Gly Gly Phe Ala Gly Asn Tyr Ala Phe Lys
225                 230                 235                 240

Tyr Ala Arg His Ala Asn Val Gly Arg Asn Ala Phe Glu Leu Phe Leu
                245                 250                 255

Ile Gly Ser Gly Ser Asp Gln Ala Lys Gly Thr Asp Pro Leu Lys Asn
            260                 265                 270

His Gln Val His Arg Leu Thr Gly Gly Tyr Glu Glu Gly Gly Leu Asn
            275                 280                 285

Leu Ala Leu Ala Ala Gln Leu Asp Leu Ser Glu Asn Gly Asp Lys Thr
290                 295                 300

Lys Asn Ser Thr Thr Glu Ile Ala Ala Thr Ala Ser Tyr Arg Phe Gly
305                 310                 315                 320

Asn Ala Val Pro Arg Ile Ser Tyr Ala His Gly Phe Asp Phe Ile Glu
                325                 330                 335

Arg Gly Lys Lys Gly Glu Asn Thr Ser Tyr Asp Gln Ile Ile Ala Gly
            340                 345                 350

Val Asp Tyr Asp Phe Ser Lys Arg Thr Ser Ala Ile Val Ser Gly Ala
            355                 360                 365

Trp Leu Lys Arg Asn Thr Gly Ile Gly Asn Tyr Thr Gln Ile Asn Ala
370                 375                 380

Ala Ser Val Gly Leu Arg His Lys Phe
385                 390

<210> SEQ ID NO 11
<211> LENGTH: 392

<212> TYPE: PRT
<213> ORGANISM: Artificial sequence
<220> FEATURE:
<223> OTHER INFORMATION: porA mutant

<400> SEQUENCE: 11

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
            115                 120                 125

Arg Val Ala Asn Gln Phe Asp Asp Ala Ser Gln Ala Ile Asp Pro Trp
        130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Lys Arg Asn Thr Gly Ile Gly Asn Tyr Thr Gln Ile
        195                 200                 205

Asn Pro Ala Val Val Gly Lys Pro Gly Ser Asp Val Tyr Tyr Ala Gly
    210                 215                 220

Leu Asn Tyr Lys Asn Gly Gly Phe Ala Gly Asn Tyr Ala Phe Lys Tyr
225                 230                 235                 240

Ala Arg His Ala Asn Val Gly Arg Asn Ala Phe Glu Leu Phe Leu Ile
                245                 250                 255

Gly Ser Gly Ser Asp Gln Ala Lys Gly Thr Asp Pro Leu Lys Asn His
            260                 265                 270

Gln Val His Arg Leu Thr Gly Gly Tyr Glu Gly Gly Leu Asn Leu
        275                 280                 285

Ala Leu Ala Ala Gln Leu Asp Leu Ser Glu Asn Gly Asp Lys Thr Lys
    290                 295                 300

Asn Ser Thr Thr Glu Ile Ala Ala Thr Ala Ser Tyr Arg Phe Gly Asn
305                 310                 315                 320

Ala Val Pro Arg Ile Ser Tyr Ala His Gly Phe Asp Phe Ile Glu Arg
                325                 330                 335

Gly Lys Lys Gly Glu Asn Thr Ser Tyr Asp Gln Ile Ile Ala Gly Val
            340                 345                 350

Asp Tyr Asp Phe Ser Lys Arg Thr Ser Ala Ile Val Ser Gly Ala Trp
        355                 360                 365

Leu Lys Arg Asn Thr Gly Ile Gly Asn Tyr Thr Gln Ile Asn Ala Ala
    370                 375                 380

Ser Val Gly Leu Arg His Lys Phe
385                 390

<210> SEQ ID NO 12
<211> LENGTH: 372
<212> TYPE: PRT
<213> ORGANISM: Artificial sequence
<220> FEATURE:
<223> OTHER INFORMATION: porA mutant

<400> SEQUENCE: 12

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ser Arg Ile Arg Thr Lys
        35                  40                  45

Ile Ser Asp Phe Gly Ser Phe Ile Gly Phe Lys Gly Ser Glu Asp Leu
    50                  55                  60

Gly Asp Gly Leu Lys Ala Val Trp Gln Leu Glu Gln Asp Val Ser Val
65                  70                  75                  80

Ala Gly Gly Gly Ala Thr Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asp Pro Trp Asp Ser Asn Asn Asp
        115                 120                 125

Val Ala Ser Gln Leu Gly Ile Phe Lys Arg His Asp Asp Met Pro Val
    130                 135                 140

Ser Val Arg Tyr Asp Ser Pro Glu Phe Ser Gly Phe Ser Gly Ser Val
145                 150                 155                 160

Gln Phe Val Pro Ile Gln Asn Ser Lys Ser Ala Tyr Thr Pro Ala Phe
                165                 170                 175

Asp Phe Ile Glu Arg Gly Lys Lys Gly Glu Asn Thr Ser Pro Ala Val
            180                 185                 190

Val Gly Lys Pro Gly Ser Asp Val Tyr Tyr Ala Gly Leu Asn Tyr Lys
        195                 200                 205

Asn Gly Gly Phe Ala Gly Asn Tyr Ala Phe Lys Tyr Ala Arg His Ala
    210                 215                 220

Asn Val Gly Arg Asn Ala Ser Glu Leu Phe Leu Ile Gly Ser Gly Ser
225                 230                 235                 240

Asp Gln Ala Lys Gly Thr Asp Pro Leu Lys Asn His Gln Val His Arg
                245                 250                 255

Leu Thr Gly Gly Tyr Glu Glu Gly Gly Leu Asn Leu Ala Leu Ala Ala
            260                 265                 270

Gln Leu Asp Leu Ser Glu Asn Gly Asp Lys Thr Lys Asn Ser Thr Thr
        275                 280                 285

Glu Ile Ala Ala Thr Ala Ser Tyr Arg Phe Gly Asn Ala Val Pro Arg
    290                 295                 300

Ile Ser Tyr Ala His Gly Phe Asp Phe Ile Glu Arg Gly Lys Lys Gly
305                 310                 315                 320

Glu Asn Thr Ser Tyr Asp Gln Ile Ile Ala Gly Val Asp Tyr Asp Phe
                325                 330                 335

Ser Lys Arg Thr Ser Ala Ile Val Ser Gly Ala Trp Leu Lys Arg Asn
            340                 345                 350

Thr Gly Ile Gly Asn Tyr Thr Gln Ile Asn Ala Ala Ser Val Gly Leu
        355                 360                 365
Arg His Lys Phe
    370

<210> SEQ ID NO 13
<211> LENGTH: 371
<212> TYPE: PRT
<213> ORGANISM: Artificial sequence
<220> FEATURE:
<223> OTHER INFORMATION: porA mutant

<400> SEQUENCE: 13

Met Arg Lys Lys Leu Thr Ala Leu Val Leu Ser Ala Leu Pro Leu Ala
1               5                   10                  15
Ala Val Ala Asp Val Ser Leu Tyr Gly Glu Ile Lys Ala Gly Val Glu
            20                  25                  30
Gly Arg Asn Tyr Gln Leu Gln Leu Thr Glu Ser Arg Ile Arg Thr Lys
        35                  40                  45
Ile Ser Asp Phe Gly Ser Phe Ile Gly Phe Lys Gly Ser Glu Asp Leu
    50                  55                  60
Gly Asp Gly Leu Lys Ala Val Trp Gln Leu Glu Gln Asp Val Ser Val
65                  70                  75                  80
Ala Gly Gly Gly Ala Thr Gln Trp Gly Asn Arg Glu Ser Phe Ile Gly
                85                  90                  95
Leu Ala Gly Glu Phe Gly Thr Leu Arg Ala Gly Arg Val Ala Asn Gln
            100                 105                 110
Phe Asp Asp Ala Ser Gln Ala Ile Asp Pro Trp Asp Ser Asn Asn Asp
        115                 120                 125
Val Ala Ser Gln Leu Gly Ile Phe Lys Arg His Asp Asp Met Pro Val
130                 135                 140
Ser Val Arg Tyr Asp Ser Pro Glu Phe Ser Gly Phe Ser Gly Ser Val
145                 150                 155                 160
Gln Phe Val Pro Ile Gln Asn Ser Lys Ser Ala Tyr Thr Pro Ala Lys
                165                 170                 175
Arg Asn Thr Gly Ile Gly Asn Tyr Thr Gln Ile Asn Pro Ala Val Val
            180                 185                 190
Gly Lys Pro Gly Ser Asp Val Tyr Tyr Ala Gly Leu Asn Tyr Lys Asn
        195                 200                 205
Gly Gly Phe Ala Gly Asn Tyr Ala Phe Lys Tyr Ala Arg His Ala Asn
    210                 215                 220
Val Gly Arg Asn Ala Phe Glu Leu Phe Leu Ile Gly Ser Gly Ser Asp
225                 230                 235                 240
Gln Ala Lys Gly Thr Asp Pro Leu Lys Asn His Gln Val His Arg Leu
                245                 250                 255
Thr Gly Gly Tyr Glu Glu Gly Gly Leu Asn Leu Ala Leu Ala Ala Gln
            260                 265                 270
Leu Asp Leu Ser Glu Asn Gly Asp Lys Thr Lys Asn Ser Thr Thr Glu
        275                 280                 285
Ile Ala Ala Thr Ala Ser Tyr Arg Phe Gly Asn Ala Val Pro Arg Ile
    290                 295                 300
Ser Tyr Ala His Gly Phe Asp Phe Ile Glu Arg Gly Lys Lys Gly Glu
305                 310                 315                 320
Asn Thr Ser Tyr Asp Gln Ile Ile Ala Gly Val Asp Tyr Asp Phe Ser
                325                 330                 335

```
Lys Arg Thr Ser Ala Ile Val Ser Gly Ala Trp Leu Lys Arg Asn Thr
                340                 345                 350

Gly Ile Gly Asn Tyr Thr Gln Ile Asn Ala Ala Ser Val Gly Leu Arg
            355                 360                 365

His Lys Phe
        370

<210> SEQ ID NO 14
<211> LENGTH: 385
<212> TYPE: PRT
<213> ORGANISM: Artificial sequence
<220> FEATURE:
<223> OTHER INFORMATION: porA mutant

<400> SEQUENCE: 14

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Phe Asp Phe Ile Glu Arg
        35                  40                  45

Gly Lys Lys Gly Glu Asn Thr Ser Ser Arg Ile Arg Thr Lys Ile Ser
    50                  55                  60

Asp Phe Gly Ser Phe Ile Gly Phe Lys Gly Ser Glu Asp Leu Gly Asp
65                  70                  75                  80

Gly Leu Lys Ala Val Trp Gln Leu Glu Gln Asp Val Ser Val Ala Gly
                85                  90                  95

Gly Gly Ala Thr Gln Trp Gly Asn Arg Glu Ser Phe Ile Gly Leu Ala
            100                 105                 110

Gly Glu Phe Gly Thr Leu Arg Ala Gly Arg Val Ala Asn Gln Phe Asp
        115                 120                 125

Asp Ala Ser Gln Ala Ile Asp Pro Trp Asp Ser Asn Asn Asp Val Ala
    130                 135                 140

Ser Gln Leu Gly Ile Phe Lys Arg His Asp Asp Met Pro Val Ser Val
145                 150                 155                 160

Arg Tyr Asp Ser Pro Glu Phe Ser Gly Phe Ser Gly Ser Val Gln Phe
                165                 170                 175

Val Pro Ile Gln Asn Ser Lys Ser Ala Tyr Thr Pro Ala Lys Arg Asn
            180                 185                 190

Thr Gly Ile Gly Asn Tyr Thr Gln Ile Asn Pro Ala Val Val Gly Lys
        195                 200                 205

Pro Gly Ser Asp Val Tyr Tyr Ala Gly Leu Asn Tyr Lys Asn Gly Gly
    210                 215                 220

Phe Ala Gly Asn Tyr Ala Phe Lys Tyr Ala Arg His Ala Asn Val Gly
225                 230                 235                 240

Arg Asn Ala Phe Glu Leu Phe Leu Ile Gly Ser Gly Ser Asp Gln Ala
                245                 250                 255

Lys Gly Thr Asp Pro Leu Lys Asn His Gln Val His Arg Leu Thr Gly
            260                 265                 270

Gly Tyr Glu Glu Gly Gly Leu Asn Leu Ala Leu Ala Ala Gln Leu Asp
        275                 280                 285

Leu Ser Glu Asn Gly Asp Lys Thr Lys Asn Ser Thr Thr Glu Ile Ala
    290                 295                 300

Ala Thr Ala Ser Tyr Arg Phe Gly Asn Ala Val Pro Arg Ile Ser Tyr
305                 310                 315                 320
```

```
Ala His Gly Phe Asp Phe Ile Glu Arg Gly Lys Lys Gly Glu Asn Thr
                325                 330                 335

Ser Tyr Asp Gln Ile Ile Ala Gly Val Asp Tyr Asp Phe Ser Lys Arg
            340                 345                 350

Thr Ser Ala Ile Val Ser Gly Ala Trp Leu Lys Arg Asn Thr Gly Ile
        355                 360                 365

Gly Asn Tyr Thr Gln Ile Asn Ala Ala Ser Val Gly Leu Arg His Lys
    370                 375                 380

Phe
385

<210> SEQ ID NO 15
<211> LENGTH: 364
<212> TYPE: PRT
<213> ORGANISM: Artificial sequence
<220> FEATURE:
<223> OTHER INFORMATION: porA mutant

<400> SEQUENCE: 15

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Phe Asp Phe Ile Glu Arg
        35                  40                  45

Gly Lys Lys Gly Glu Asn Thr Ser Ser Arg Ile Arg Thr Lys Ile Ser
    50                  55                  60

Asp Phe Gly Ser Phe Ile Gly Phe Lys Gly Ser Glu Asp Leu Gly Asp
65                  70                  75                  80

Gly Leu Lys Ala Val Trp Gln Leu Glu Gln Asp Val Ser Val Ala Gly
                85                  90                  95

Gly Gly Ala Thr Gln Trp Gly Asn Arg Glu Ser Phe Ile Gly Leu Ala
            100                 105                 110

Gly Glu Phe Gly Thr Leu Arg Ala Gly Arg Val Ala Asn Gln Phe Asp
        115                 120                 125

Asp Ala Ser Gln Ala Ile Asp Pro Trp Asp Ser Asn Asn Asp Val Ala
    130                 135                 140

Ser Gln Leu Gly Ile Phe Lys Arg His Asp Asp Met Pro Val Ser Val
145                 150                 155                 160

Arg Tyr Asp Ser Pro Glu Phe Ser Gly Phe Ser Gly Ser Val Gln Phe
                165                 170                 175

Val Pro Ile Gln Asn Ser Lys Ser Ala Tyr Thr Pro Ala Lys Arg Asn
            180                 185                 190

Thr Gly Ile Gly Asn Tyr Thr Gln Ile Asn Pro Ala Val Val Gly Lys
        195                 200                 205

Pro Gly Ser Asp Val Tyr Tyr Ala Gly Leu Asn Tyr Lys Asn Gly Gly
    210                 215                 220

Phe Ala Gly Asn Tyr Ala Phe Lys Tyr Ala Arg His Ala Asn Val Gly
225                 230                 235                 240

Leu Lys Asn His Gln Val His Arg Leu Thr Gly Gly Tyr Glu Glu Gly
                245                 250                 255

Gly Leu Asn Leu Ala Leu Ala Ala Gln Leu Asp Leu Ser Glu Asn Gly
            260                 265                 270

Asp Lys Thr Lys Asn Ser Thr Thr Glu Ile Ala Ala Thr Ala Ser Tyr
        275                 280                 285
```

```
Arg Phe Gly Asn Ala Val Pro Arg Ile Ser Tyr Ala His Gly Phe Asp
        290                 295                 300

Phe Ile Glu Arg Gly Lys Lys Gly Glu Asn Thr Ser Tyr Asp Gln Ile
305                 310                 315                 320

Ile Ala Gly Val Asp Tyr Asp Phe Ser Lys Arg Thr Ser Ala Ile Val
                325                 330                 335

Ser Gly Ala Trp Leu Lys Arg Asn Thr Gly Ile Gly Asn Tyr Thr Gln
            340                 345                 350

Ile Asn Ala Ala Ser Val Gly Leu Arg His Lys Phe
        355                 360
```

<210> SEQ ID NO 16
<211> LENGTH: 329
<212> TYPE: PRT
<213> ORGANISM: Artificial sequence
<220> FEATURE:
<223> OTHER INFORMATION: porA mutant

<400> SEQUENCE: 16

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ser Arg Ile Arg Thr Lys
        35                  40                  45

Ile Ser Asp Phe Gly Ser Phe Ile Gly Phe Lys Gly Ser Glu Asp Leu
    50                  55                  60

Gly Asp Gly Leu Lys Ala Val Trp Gln Leu Glu Gln Asp Val Ser Val
65                  70                  75                  80

Ala Gly Gly Gly Ala Thr Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asp Pro Trp Asp Ser Asn Asn Asp
        115                 120                 125

Val Ala Ser Gln Leu Gly Ile Phe Lys Arg His Asp Asp Met Pro Val
130                 135                 140

Ser Val Arg Tyr Asp Ser Pro Glu Phe Ser Gly Phe Ser Gly Ser Val
145                 150                 155                 160

Gln Phe Val Pro Ile Gln Asn Ser Lys Ser Ala Tyr Thr Pro Ala Pro
                165                 170                 175

Ala Val Val Gly Lys Pro Gly Ser Asp Val Tyr Tyr Ala Gly Leu Asn
            180                 185                 190

Tyr Lys Asn Gly Gly Phe Ala Gly Asn Tyr Ala Phe Lys Tyr Ala Arg
        195                 200                 205

His Ala Asn Val Gly Leu Lys Asn His Gln Val His Arg Leu Thr Gly
    210                 215                 220

Gly Tyr Glu Glu Gly Leu Asn Leu Ala Leu Ala Ala Gln Leu Asp
225                 230                 235                 240

Leu Ser Ser Thr Thr Glu Ile Ala Ala Thr Ala Ser Tyr Arg Phe Gly
                245                 250                 255

Asn Ala Val Pro Arg Ile Ser Tyr Ala His Gly Phe Asp Phe Ile Glu
            260                 265                 270

Arg Gly Lys Lys Gly Glu Asn Thr Ser Tyr Asp Gln Ile Ile Ala Gly
        275                 280                 285
```

```
Val Asp Tyr Asp Phe Ser Lys Arg Thr Ser Ala Ile Val Ser Gly Ala
    290                 295                 300

Trp Leu Lys Arg Asn Thr Gly Ile Gly Asn Tyr Thr Gln Ile Asn Ala
305                 310                 315                 320

Ala Ser Val Gly Leu Arg His Lys Phe
                325
```

<210> SEQ ID NO 17
<211> LENGTH: 406
<212> TYPE: PRT
<213> ORGANISM: Artificial sequence
<220> FEATURE:
<223> OTHER INFORMATION: porA mutant

<400> SEQUENCE: 17

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
                20                  25                  30

Gly Arg Asn Tyr Gln Leu Gln Leu Thr Glu Ala Gln Ala Ala Asn Gly
            35                  40                  45

Gly Ala Phe Asp Phe Ile Glu Arg Gly Lys Gly Glu Asn Thr Ser
    50                  55                  60

Ser Gly Gln Val Lys Val Thr Lys Val Thr Lys Ala Lys Ser Arg Ile
65                  70                  75                  80

Arg Thr Lys Ile Ser Asp Phe Gly Ser Phe Ile Gly Phe Lys Gly Ser
                85                  90                  95

Glu Asp Leu Gly Asp Gly Leu Lys Ala Val Trp Gln Leu Glu Gln Asp
            100                 105                 110

Val Ser Val Ala Gly Gly Ala Thr Gln Trp Gly Asn Arg Glu Ser
        115                 120                 125

Phe Ile Gly Leu Ala Gly Glu Phe Gly Thr Leu Arg Ala Gly Arg Val
    130                 135                 140

Ala Asn Gln Phe Asp Asp Ala Ser Gln Ala Ile Asp Pro Trp Asp Ser
145                 150                 155                 160

Asn Asn Asp Val Ala Ser Gln Leu Gly Ile Phe Lys Arg His Asp Asp
                165                 170                 175

Met Pro Val Ser Val Arg Tyr Asp Ser Pro Glu Phe Ser Gly Phe Ser
            180                 185                 190

Gly Ser Val Gln Phe Val Pro Ile Gln Asn Ser Lys Ser Ala Tyr Thr
        195                 200                 205

Pro Ala Tyr Tyr Thr Lys Asn Thr Asn Asn Asn Leu Thr Leu Val Pro
    210                 215                 220

Ala Val Val Gly Lys Pro Gly Ser Asp Val Tyr Tyr Ala Gly Leu Asn
225                 230                 235                 240

Tyr Lys Asn Gly Gly Phe Ala Gly Asn Tyr Ala Phe Lys Tyr Ala Arg
                245                 250                 255

His Ala Asn Val Gly Arg Asn Ala Phe Glu Leu Phe Leu Ile Gly Ser
            260                 265                 270

Gly Ser Asp Gln Ala Lys Gly Thr Asp Pro Leu Lys Asn His Gln Val
        275                 280                 285

His Arg Leu Thr Gly Gly Tyr Glu Glu Gly Leu Asn Leu Ala Leu
    290                 295                 300

Ala Ala Gln Leu Asp Leu Ser Glu Asn Gly Asp Lys Thr Lys Asn Ser
305                 310                 315                 320
```

```
Thr Thr Glu Ile Ala Thr Ala Ser Tyr Arg Phe Gly Asn Ala Val
            325                 330                 335

Pro Arg Ile Ser Tyr Ala His Gly Phe Asp Phe Ile Glu Arg Gly Lys
            340                 345                 350

Lys Gly Glu Asn Thr Ser Tyr Asp Gln Ile Ile Ala Gly Val Asp Tyr
            355                 360                 365

Asp Phe Ser Lys Arg Thr Ser Ala Ile Val Ser Gly Ala Trp Leu Lys
            370                 375                 380

Arg Asn Thr Gly Ile Gly Asn Tyr Thr Gln Ile Asn Ala Ala Ser Val
385                 390                 395                 400

Gly Leu Arg His Lys Phe
                    405
```

<210> SEQ ID NO 18
<211> LENGTH: 405
<212> TYPE: PRT
<213> ORGANISM: Artificial sequence
<220> FEATURE:
<223> OTHER INFORMATION: porA mutant

<400> SEQUENCE: 18

```
Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
    130                 135                 140

Asp Ser Asn Asn Asp Val Ala Ser Gln Leu Gly Ile Phe Lys Arg His
145                 150                 155                 160

Asp Asp Met Pro Val Ser Val Arg Tyr Asp Ser Pro Glu Phe Ser Gly
                165                 170                 175

Phe Ser Gly Ser Val Gln Phe Val Pro Ile Gln Asn Ser Lys Ser Ala
            180                 185                 190

Tyr Thr Pro Ala Tyr Tyr Thr Lys Asn Thr Asn Lys Arg Asn Thr Gly
        195                 200                 205

Ile Gly Asn Tyr Thr Gln Ile Asn Asn Leu Thr Leu Val Pro Ala
    210                 215                 220

Val Val Gly Lys Pro Gly Ser Asp Val Tyr Tyr Ala Gly Leu Asn Tyr
225                 230                 235                 240

Lys Asn Gly Gly Phe Ala Gly Asn Tyr Ala Phe Lys Tyr Ala Arg His
                245                 250                 255

Ala Asn Val Gly Arg Asn Ala Phe Glu Leu Phe Leu Ile Gly Ser Gly
            260                 265                 270
```

```
Ser Asp Gln Ala Lys Gly Thr Asp Pro Leu Lys Asn His Gln Val His
            275                 280                 285

Arg Leu Thr Gly Gly Tyr Glu Glu Gly Leu Asn Leu Ala Leu Ala
    290                 295                 300

Ala Gln Leu Asp Leu Ser Glu Asn Gly Asp Lys Thr Lys Asn Ser Thr
305                 310                 315                 320

Thr Glu Ile Ala Ala Thr Ala Ser Tyr Arg Phe Gly Asn Ala Val Pro
                325                 330                 335

Arg Ile Ser Tyr Ala His Gly Phe Asp Phe Ile Glu Arg Gly Lys Lys
                340                 345                 350

Gly Glu Asn Thr Ser Tyr Asp Gln Ile Ile Ala Gly Val Asp Tyr Asp
                355                 360                 365

Phe Ser Lys Arg Thr Ser Ala Ile Val Ser Gly Ala Trp Leu Lys Arg
    370                 375                 380

Asn Thr Gly Ile Gly Asn Tyr Thr Gln Ile Asn Ala Ala Ser Val Gly
385                 390                 395                 400

Leu Arg His Lys Phe
                405

<210> SEQ ID NO 19
<211> LENGTH: 419
<212> TYPE: PRT
<213> ORGANISM: Artificial sequence
<220> FEATURE:
<223> OTHER INFORMATION: porA mutant

<400> SEQUENCE: 19

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Phe Asp Phe Ile Glu Arg Gly Lys Lys Gly Glu Asn Thr Ser
50                  55                  60

Ser Gly Gln Val Lys Val Thr Lys Val Thr Lys Ala Lys Ser Arg Ile
65                  70                  75                  80

Arg Thr Lys Ile Ser Asp Phe Gly Ser Phe Ile Gly Phe Lys Gly Ser
                85                  90                  95

Glu Asp Leu Gly Asp Gly Leu Lys Ala Val Trp Gln Leu Glu Gln Asp
            100                 105                 110

Val Ser Val Ala Gly Gly Ala Thr Gln Trp Gly Asn Arg Glu Ser
    115                 120                 125

Phe Ile Gly Leu Ala Gly Glu Phe Gly Thr Leu Arg Ala Gly Arg Val
    130                 135                 140

Ala Asn Gln Phe Asp Asp Ala Ser Gln Ala Ile Asp Pro Trp Asp Ser
145                 150                 155                 160

Asn Asn Asp Val Ala Ser Gln Leu Gly Ile Phe Lys Arg His Asp Asp
                165                 170                 175

Met Pro Val Ser Val Arg Tyr Asp Ser Pro Glu Phe Ser Gly Phe Ser
                180                 185                 190

Gly Ser Val Gln Phe Val Pro Ile Gln Asn Ser Lys Ser Ala Tyr Thr
        195                 200                 205

Pro Ala Tyr Tyr Thr Lys Asn Thr Asn Lys Arg Asn Thr Gly Ile Gly
210                 215                 220
```

```
Asn Tyr Thr Gln Ile Asn Asn Leu Thr Leu Val Pro Ala Val Val
225                 230                 235                 240

Gly Lys Pro Gly Ser Asp Val Tyr Tyr Ala Gly Leu Asn Tyr Lys Asn
                245                 250                 255

Gly Gly Phe Ala Gly Asn Tyr Ala Phe Lys Tyr Ala Arg His Ala Asn
            260                 265                 270

Val Gly Arg Asn Ala Phe Glu Leu Phe Leu Ile Gly Ser Gly Ser Asp
        275                 280                 285

Gln Ala Lys Gly Thr Asp Pro Leu Lys Asn His Gln Val His Arg Leu
290                 295                 300

Thr Gly Tyr Glu Glu Gly Leu Asn Leu Ala Leu Ala Ala Gln
305                 310                 315                 320

Leu Asp Leu Ser Glu Asn Gly Asp Lys Thr Lys Asn Ser Thr Thr Glu
                325                 330                 335

Ile Ala Ala Thr Ala Ser Tyr Arg Phe Gly Asn Ala Val Pro Arg Ile
                340                 345                 350

Ser Tyr Ala His Gly Phe Asp Phe Ile Glu Arg Gly Lys Lys Gly Glu
                355                 360                 365

Asn Thr Ser Tyr Asp Gln Ile Ile Ala Gly Val Asp Tyr Asp Phe Ser
            370                 375                 380

Lys Arg Thr Ser Ala Ile Val Ser Gly Ala Trp Leu Lys Arg Asn Thr
385                 390                 395                 400

Gly Ile Gly Asn Tyr Thr Gln Ile Asn Ala Ser Val Gly Leu Arg
                405                 410                 415

His Lys Phe

<210> SEQ ID NO 20
<211> LENGTH: 386
<212> TYPE: PRT
<213> ORGANISM: Artificial sequence
<220> FEATURE:
<223> OTHER INFORMATION: porA mutant

<400> SEQUENCE: 20

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
                20                  25                  30

Gly Arg Asn Tyr Gln Leu Gln Leu Thr Glu Phe Asp Phe Ile Glu Arg
            35                  40                  45

Gly Lys Lys Gly Glu Asn Thr Ser Ser Arg Ile Arg Thr Lys Ile Ser
        50                  55                  60

Asp Phe Gly Ser Phe Ile Gly Phe Lys Gly Ser Glu Asp Leu Gly Asp
65                  70                  75                  80

Gly Leu Lys Ala Val Trp Gln Leu Glu Gln Asp Val Ser Val Ala Gly
                85                  90                  95

Gly Gly Ala Thr Gln Trp Gly Asn Arg Glu Ser Phe Ile Gly Leu Ala
            100                 105                 110

Gly Glu Phe Gly Thr Leu Arg Ala Gly Arg Val Ala Asn Gln Phe Asp
        115                 120                 125

Asp Ala Ser Gln Ala Ile Asp Pro Trp Asp Ser Asn Asn Asp Val Ala
    130                 135                 140

Ser Gln Leu Gly Ile Phe Lys Arg His Asp Asp Met Pro Val Ser Val
145                 150                 155                 160

Arg Tyr Asp Ser Pro Glu Phe Ser Gly Phe Ser Gly Ser Val Gln Phe
```

```
                    165                 170                 175
Val Pro Ile Gln Asn Ser Lys Ser Ala Tyr Thr Pro Ala Phe Asp Phe
                180                 185                 190

Ile Glu Arg Gly Lys Lys Gly Glu Asn Thr Ser Pro Ala Val Val Gly
            195                 200                 205

Lys Pro Gly Ser Asp Val Tyr Tyr Ala Gly Leu Asn Tyr Lys Asn Gly
        210                 215                 220

Gly Phe Ala Gly Asn Tyr Ala Phe Lys Tyr Ala Arg His Ala Asn Val
225                 230                 235                 240

Gly Arg Asn Ala Phe Glu Leu Phe Leu Ile Gly Ser Gly Ser Asp Gln
                245                 250                 255

Ala Lys Gly Thr Asp Pro Leu Lys Asn His Gln Val His Arg Leu Thr
            260                 265                 270

Gly Gly Tyr Glu Glu Gly Leu Asn Leu Ala Leu Ala Ala Gln Leu
        275                 280                 285

Asp Leu Ser Glu Asn Gly Asp Lys Thr Lys Asn Ser Thr Thr Glu Ile
290                 295                 300

Ala Ala Thr Ala Ser Tyr Arg Phe Gly Asn Ala Val Pro Arg Ile Ser
305                 310                 315                 320

Tyr Ala His Gly Phe Asp Phe Ile Glu Arg Gly Lys Lys Gly Glu Asn
                325                 330                 335

Thr Ser Tyr Asp Gln Ile Ile Ala Gly Val Asp Tyr Asp Phe Ser Lys
            340                 345                 350

Arg Thr Ser Ala Ile Val Ser Gly Ala Trp Leu Lys Arg Asn Thr Gly
        355                 360                 365

Ile Gly Asn Tyr Thr Gln Ile Asn Ala Ala Ser Val Gly Leu Arg His
370                 375                 380

Lys Phe
385

<210> SEQ ID NO 21
<211> LENGTH: 384
<212> TYPE: PRT
<213> ORGANISM: Artificial sequence
<220> FEATURE:
<223> OTHER INFORMATION: porA mutant

<400> SEQUENCE: 21

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Lys Arg Asn Thr Gly Ile
        35                  40                  45

Gly Asn Tyr Thr Gln Ile Asn Ser Arg Ile Arg Thr Lys Ile Ser Asp
    50                  55                  60

Phe Gly Ser Phe Ile Gly Phe Lys Gly Ser Glu Asp Leu Gly Asp Gly
65                  70                  75                  80

Leu Lys Ala Val Trp Gln Leu Glu Gln Asp Val Ser Val Ala Gly Gly
                85                  90                  95

Gly Ala Thr Gln Trp Gly Asn Arg Glu Ser Phe Ile Gly Leu Ala Gly
            100                 105                 110

Glu Phe Gly Thr Leu Arg Ala Gly Arg Val Ala Asn Gln Phe Asp Asp
        115                 120                 125

Ala Ser Gln Ala Ile Asp Pro Trp Asp Ser Asn Asn Asp Val Ala Ser
```

```
            130                 135                 140
Gln Leu Gly Ile Phe Lys Arg His Asp Asp Met Pro Val Ser Val Arg
145                 150                 155                 160

Tyr Asp Ser Pro Glu Phe Ser Gly Phe Ser Gly Ser Val Gln Phe Val
                165                 170                 175

Pro Ile Gln Asn Ser Lys Ser Ala Tyr Thr Pro Ala Lys Arg Asn Thr
                180                 185                 190

Gly Ile Gly Asn Tyr Thr Gln Ile Asn Pro Ala Val Val Gly Lys Pro
                195                 200                 205

Gly Ser Asp Val Tyr Tyr Ala Gly Leu Asn Tyr Lys Asn Gly Phe
210                 215                 220

Ala Gly Asn Tyr Ala Phe Lys Tyr Ala Arg His Ala Asn Val Gly Arg
225                 230                 235                 240

Asn Ala Phe Glu Leu Phe Leu Ile Gly Ser Gly Ser Asp Gln Ala Lys
                245                 250                 255

Gly Thr Asp Pro Leu Lys Asn His Gln Val His Arg Leu Thr Gly Gly
                260                 265                 270

Tyr Glu Glu Gly Gly Leu Asn Leu Ala Leu Ala Ala Gln Leu Asp Leu
                275                 280                 285

Ser Glu Asn Gly Asp Lys Thr Lys Asn Ser Thr Thr Glu Ile Ala Ala
290                 295                 300

Thr Ala Ser Tyr Arg Phe Gly Asn Ala Val Pro Arg Ile Ser Tyr Ala
305                 310                 315                 320

His Gly Phe Asp Phe Ile Glu Arg Gly Lys Lys Gly Glu Asn Thr Ser
                325                 330                 335

Tyr Asp Gln Ile Ile Ala Gly Val Asp Tyr Asp Phe Ser Lys Arg Thr
                340                 345                 350

Ser Ala Ile Val Ser Gly Ala Trp Leu Lys Arg Asn Thr Gly Ile Gly
                355                 360                 365

Asn Tyr Thr Gln Ile Asn Ala Ala Ser Val Gly Leu Arg His Lys Phe
                370                 375                 380

<210> SEQ ID NO 22
<211> LENGTH: 385
<212> TYPE: PRT
<213> ORGANISM: Artificial sequence
<220> FEATURE:
<223> OTHER INFORMATION: porA mutant

<400> SEQUENCE: 22

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
                20                  25                  30

Gly Arg Asn Tyr Gln Leu Gln Leu Thr Glu Lys Arg Asn Thr Gly Ile
                35                  40                  45

Gly Asn Tyr Thr Gln Ile Asn Ser Arg Ile Arg Thr Lys Ile Ser Asp
                50                  55                  60

Phe Gly Ser Phe Ile Gly Phe Lys Gly Ser Glu Asp Leu Gly Asp Gly
65                  70                  75                  80

Leu Lys Ala Val Trp Gln Leu Glu Gln Asn Val Ser Val Ala Gly Gly
                85                  90                  95

Gly Ala Thr Gln Trp Gly Asn Arg Glu Ser Phe Ile Gly Leu Ala Gly
                100                 105                 110

Glu Phe Gly Thr Leu Arg Ala Gly Arg Val Ala Asn Gln Phe Asp Asp
```

|  | 115 |  |  | 120 |  |  |  | 125 |  |  |
|---|---|---|---|---|---|---|---|---|---|---|

Ala Ser Gln Ala Ile Asp Pro Trp Asp Ser Asn Asn Asp Val Ala Ser
130 135 140

Gln Leu Gly Ile Phe Lys Arg His Asp Asp Met Pro Val Ser Val Arg
145 150 155 160

Tyr Asp Ser Pro Glu Phe Ser Gly Phe Ser Gly Ser Val Gln Phe Val
165 170 175

Pro Ile Gln Asn Ser Lys Ser Ala Tyr Thr Pro Ala Phe Asp Phe Ile
180 185 190

Glu Arg Gly Lys Lys Gly Glu Asn Thr Ser Pro Ala Val Val Gly Lys
195 200 205

Pro Gly Ser Asp Val Tyr Tyr Ala Gly Leu Asn Tyr Lys Asn Gly Gly
210 215 220

Phe Ala Gly Asn Tyr Ala Phe Lys Tyr Ala Arg His Ala Asn Val Gly
225 230 235 240

Arg Asn Ala Phe Glu Leu Phe Leu Ile Gly Ser Gly Ser Asp Gln Ala
245 250 255

Lys Gly Thr Asp Pro Leu Lys Asn His Gln Val His Arg Leu Thr Gly
260 265 270

Gly Tyr Glu Glu Gly Leu Asn Leu Ala Leu Ala Ala Gln Leu Asp
275 280 285

Leu Ser Glu Asn Gly Asp Lys Thr Lys Asn Ser Thr Thr Glu Ile Ala
290 295 300

Ala Thr Ala Ser Tyr Arg Phe Gly Asn Ala Val Pro Arg Ile Ser Tyr
305 310 315 320

Ala His Gly Phe Asp Phe Ile Glu Arg Gly Lys Lys Gly Glu Asn Thr
325 330 335

Ser Tyr Asp Gln Ile Ile Ala Gly Val Asp Tyr Asp Phe Ser Lys Arg
340 345 350

Thr Ser Ala Ile Val Ser Gly Ala Trp Leu Lys Arg Asn Thr Gly Ile
355 360 365

Gly Asn Tyr Thr Gln Ile Asn Ala Ala Ser Val Gly Leu Arg His Lys
370 375 380

Phe
385

```
<210> SEQ ID NO 23
<211> LENGTH: 1101
<212> TYPE: DNA
<213> ORGANISM: Artificial sequence
<220> FEATURE:
<223> OTHER INFORMATION: porA mutant

<400> SEQUENCE: 23
atgcgaaaaa aacttaccgc cctcgtattg tccgcactgc cgcttgcggc cgttgccgat      60
gtcagcctat acggcgaaat caaagccggc gtggaaggca ggaactacca gagccgcatc    120
aggacgaaaa tcagtgattt cggctcgttt atcggcttta aggggagtga ggatttgggc    180
gacgggctga aggctgtttg gcagcttgag caagacgtat ccgttgccgg cggcggcgcg    240
acccagtggg gcaacaggga atcctttatc ggcttggcag gcgaattcgg tacgctgcgc    300
gccggtcgcg ttgcgaatca gtttgacgat gccagccaag ccattgatcc ttgggacagc    360
aataatgatg tggcttcgca attgggtatt ttcaaacgcc acgacgacat gccggtttcc    420
gtacgctacg attcccccga attttccggt ttcagcggca gcgttcaatt cgttccgatc    480
```

```
caaaacagca agtccgccta tacgccggct tattatacta agaatacaaa caataatctt    540
actctcgttc cggctgttgt cggcaagccc ggatcggatg tgtattatgc cggtctgaat    600
tacaaaaatg gcggttttgc cgggaactat gcctttaaat atgcgagaca cgccaatgtc    660
ggacgtaatg cttttgagtt gttcttgatc ggcagcggga gtgatcaagc caaaggtacc    720
gatcccttga aaaccatca ggtacaccgt ctgacgggcg gctatgagga aggcggcttg    780
aatctcgcct ggcggctca gttggatttg tctgaaaatg gcgacaaaac caaaaacagt    840
acgaccgaaa ttgccgccac tgcttcctac cgcttcggta atgcagttcc acgcatcagc    900
tatgcccatg gtttcgactt tatcgaacgc ggtaaaaaag gcgaaaatac cagctacgat    960
caaatcatcg ccggcgttga ttatgatttt tccaaacgca cttccgccat cgtgtctggc   1020
gcttggctga aacgcaatac cggcatcggc aactacactc aaattaatgc cgcctccgtc   1080
ggtttgcgcc acaaattcta a                                             1101

<210> SEQ ID NO 24
<211> LENGTH: 1104
<212> TYPE: DNA
<213> ORGANISM: Artificial sequence
<220> FEATURE:
<223> OTHER INFORMATION: porA mutant

<400> SEQUENCE: 24
atgcgaaaaa aacttaccgc cctcgtattg tccgcactgc cgcttgcggc cgttgccgat     60
gtcagcctat acggcgaaat caaagccggc gtggaaggca ggaactacca gctgcaattg    120
actgaagcac aagccgctaa cggtggagcg agcggtcagg taaaagttac taaagttact    180
aaggccaaaa gccgcatcag gacgaaaatc agtgatttcg gctcgtttat cggctttaag    240
gggagtgagg atttgggcga cgggctgaag gctgtttggc agcttgagca agacgtatcc    300
gttgccggcg gcggcgcgac ccagtggggc aacagggaat cctttatcgg cttggcaggc    360
gaattcggta cgctgcgcgc cggtcgcgtt gcgaatcagt ttgacgatgc cagccaagcc    420
attgatcctt gggacagcaa taatgatgtg gcttcgcaat gggtatttt caaacgccac    480 gacgacatgc cggtttccgt acgctacgat tcccccgaat tttccggttt cagcggcagc    540
gttcaattcg ttccgatcgt tgtcggcaag cccggatcgg atgtgtatta tgccggtctg    600
aattacaaaa atgcggtttt gccgggaac tatgccttta aatatgcgag acacgccaat    660
gtcggacgta atgcttttga gttgttcttg atcggcagcg ggagtgatca agccaaaggt    720
accgatccct gaaaaacca tcaggtacac cgtctgacgg gcggctatga ggaaggcggc    780
ttgaatctcg cccttggcgg ctcagttgga ttgtctgaaa atgcgacaa accaaaaac    840 agtacgaccg aaattgccgc cactgcttcc taccgcttcg gtaatgcagt tccacgcatc    900
agctatgccc atggtttcga ctttatcgaa cgcggtaaaa aaggcgaaaa taccagctac    960
gatcaaatca tcgccggcgt tgattatgat ttttccaaac gcacttccgc catcgtgtct   1020
ggcgcttggc tgaaacgcaa taccggcatc ggcaactaca ctcaaattaa tgccgcctcc   1080
gtcggtttgc gccacaaatt ctaa                                         1104

<210> SEQ ID NO 25
<211> LENGTH: 1026
<212> TYPE: DNA
<213> ORGANISM: Artificial sequence
<220> FEATURE:
<223> OTHER INFORMATION: porA mutant

<400> SEQUENCE: 25
```

```
atgcgaaaaa aacttaccgc cctcgtattg tccgcactgc cgcttgcggc cgttgccgat     60
gtcagcctat acggcgaaat caaagccggc gtggaaggca ggaactacca gagccgcatc    120
aggacgaaaa tcagtgattt cggctcgttt atcggcttta aggggagtga ggatttgggc    180
gacgggctga aggctgtttg gcagcttgag caagacgtat ccgttgccgg cggcggcgcg    240
acccagtggg gcaacaggga atcctttatc ggcttggcag gcgaattcgg tacgctgcgc    300
gccggtcgcg ttgcgaatca gtttgacgat gccagccaag ccattgatcc ttgggacagc    360
aataatgatg tggcttcgca attgggtatt ttcaaacgcc acgacgacat gccggtttcc    420
gtacgctacg attcccccga attttccggt ttcagcggca gcgttcaatt cgttccgatc    480
gttgtcggca agcccggatc ggatgtgtat tatgccggtc tgaattacaa aaatggcggt    540
tttgccggga actatgcctt taaatatgcg agacacgcca atgtcggacg taatgctttt    600
gagttgttct tgatcggcag cgggagtgat caagccaaag gtaccgatcc cttgaaaaac    660
catcaggtac accgtctgac gggcggctat gaggaaggcg gcttgaatct cgccttggcg    720
gctcagttgg atttgtctga aaatggcgac aaaaccaaaa acagtacgac cgaaattgcc    780
gccactgctt cctaccgctt cggtaatgca gttccacgca tcagctatgc ccatggtttc    840
gactttatcg aacgcggtaa aaaaggcgaa ataccagct acgatcaaat catcgccggc    900
gttgattatg attttccaa acgcacttcc gccatcgtgt ctggcgcttg gctgaaacgc    960
aataccggca tcggcaacta cactcaaatt aatgccgcct ccgtcggttt gcgccacaaa   1020
ttctaa                                                              1026

<210> SEQ ID NO 26
<211> LENGTH: 963
<212> TYPE: DNA
<213> ORGANISM: Artificial sequence
<220> FEATURE:
<223> OTHER INFORMATION: porA mutant

<400> SEQUENCE: 26
atgcgaaaaa aacttaccgc cctcgtattg tccgcactgc cgcttgcggc cgttgccgat     60
gtcagcctat acggcgaaat caaagccggc gtggaaggca ggaactacca gagccgcatc    120
aggacgaaaa tcagtgattt cggctcgttt atcggcttta aggggagtga ggatttgggc    180
gacgggctga aggctgtttg gcagcttgag caagacgtat ccgttgccgg cggcggcgcg    240
acccagtggg gcaacaggga atcctttatc ggcttggcag gcgaattcgg tacgctgcgc    300
gccggtcgcg ttgcgaatca gtttgacgat gccagccaag ccattgatcc ttgggacagc    360
aataatgatg tggcttcgca attgggtatt ttcaaacgcc acgacgacat gccggtttcc    420
gtacgctacg attcccccga attttccggt ttcagcggca gcgttcaatt cgttccgatc    480
gttgtcggca agcccggatc ggatgtgtat tatgccggtc tgaattacaa aaatggcggt    540
tttgccggga actatgcctt taaatatgcg agacacgcca atgtcggatt gaaaaaccat    600
caggtacacc gtctgacggg cggctatgag gaaggcggct tgaatctcgc cttggcggct    660
cagttggatt tgtctgaaaa tggcgacaaa accaaaaaca gtacgaccga aattgccgcc    720
actgcttcct accgcttcgg taatgcagtt ccacgcatca gctatgccca tggtttcgac    780
tttatcgaac gcggtaaaaa aggcgaaaat accagctacg atcaaatcat cgccggcgtt    840
gattatgatt ttccaaaacg cacttccgcc atcgtgtctg gcgcttggct gaaacgcaat    900
accggcatcg gcaactacac tcaaattaat gccgcctccg tcggtttgcg ccacaaattc    960
```

```
taa                                                              963

<210> SEQ ID NO 27
<211> LENGTH: 1116
<212> TYPE: DNA
<213> ORGANISM: Artificial sequence
<220> FEATURE:
<223> OTHER INFORMATION: porA

<400> SEQUENCE: 27
atgcgaaaaa aacttaccgc cctcgtattg tccgcactgc cgcttgcggc cgttgccgat      60
gtcagcctat acggcgaaat caaagccggc gtggaaggca ggaactacca gctgcaattg     120
actgaaagcc gcatcaggac gaaaatcagt gatttcggct cgtttatcgg ctttaagggg     180
agtgaggatt tgggcgacgg gctgaaggct gtttggcagc ttgagcaaga cgtatccgtt     240
gccggcggcg gcgcgaccca gtggggcaac agggaatcct ttatcggctt ggcaggcgaa     300
ttcggtacgc tgcgcgccgg tcgcgttgcg aatcagtttg acgatgccag ccaagccatt     360
gatccttggg acagcaataa tgatgtggct tcgcaattgg gtattttcaa acgccacgac     420
gacatgccgg tttccgtacg ctacgattcc ccgaattttt ccggtttcag cggcagcgtt     480
caattcgttc cgatccaaaa cagcaagtcc gcctatacgc cggcttatta tactaagaat     540
acaaacaata atcttactct cgttccggct gttgtcggca agcccggatc ggatgtgtat     600
tatgccggtc tgaattacaa aaatggcggt tttgccggga actatgcctt taaatatgcg     660
agacacgcca atgtcggacg taatgctttt gagttgttct tgatcggcag cgggagtgat     720
caagccaaag gtaccgatcc cttgaaaaac catcaggtac accgtctgac gggcggctat     780
gaggaaggcg gcttgaatct cgccttggcg gctcagttgg atttgtctga aatggcgac      840
aaaaccaaaa acagtacgac cgaaattgcc gccactgctt cctaccgctt cggtaatgca     900
gttccacgca tcagctatgc ccatggtttc gactttatcg aacgcggtaa aaaaggcgaa     960
aataccagct acgatcaaat catcgccggc gttgattatg attttccaa acgcacttcc     1020
gccatcgtgt ctggcgcttg gctgaaacgc aataccggca tcggcaacta cactcaaatt    1080
aatgccgcct ccgtcggttt gcgccacaaa ttctaa                               1116

<210> SEQ ID NO 28
<211> LENGTH: 1140
<212> TYPE: DNA
<213> ORGANISM: Artificial sequence
<220> FEATURE:
<223> OTHER INFORMATION: porA mutant

<400> SEQUENCE: 28
atgcgaaaaa aacttaccgc cctcgtattg tccgcactgc cgcttgcggc cgttgccgat      60
gtcagcctat acggcgaaat caaagccggc gtggaaggca ggaactacca gctgcaattg     120
actgaagcac aagccgctaa cggtggagcg agcggtcagg taaaagttac taaagttact     180
aaggccaaaa gccgcatcag gacgaaaatc agtgatttcg gtcgtttat cggctttaag      240
gggagtgagg atttgggcga cgggctgaag gctgtttggc agcttgagca agacgtatcc     300
gttgccggcg gcgcgcgac ccagtggggc aacagggaat cctttatcgg cttggcaggc     360
gaattcggta cgctgcgcgc cggtcgcgtt gcgaatcagt ttgacgatgc cagccaagcc     420
attgatcctt gggacagcaa taatgatgtg cttcgcaat tgggtatttt caaacgccac     480
gacgacatgc cggtttccgt acgctacgat tccccgaat tttccggttt cagcggcagc     540
gttcaattcg ttccgatcca aaacagcaag tccgcctata cgccggctcc ggctgttgtc    600
```

| | | |
|---|---|---|
| ggcaagcccg atcggatgt gtattatgcc ggtctgaatt acaaaaatgg cggttttgcc | 660 |
| gggaactatg cctttaaata tgcgagacac gccaatgtcg dacgtaatgc ttttgagttg | 720 |
| ttcttgatcg gcagcgggag tgatcaagcc aaaggtaccg atcccttgaa aaaccatcag | 780 |
| gtacaccgtc tgacgggcgg ctatgaggaa ggcggcttga atctcgcctt ggcggctcag | 840 |
| ttggatttgt ctgaaaatgg cgacaaaacc aaaaacagta cgaccgaaat tgccgccact | 900 |
| gcttcctacc gcttcggtaa tgcagttcca cgcatcagct atgcccatgg tttcgacttt | 960 |
| atcgaacgcg gtaaaaaagg cgaaaatacc agctacgatc aaatcatcgc cggcgttgat | 1020 |
| tatgattttt ccaaacgcac ttccgccatc gtgtctggcg cttggctgaa acgcaatacc | 1080 |
| ggcatcggca actacactca aattaatgcc gcctccgtcg gtttgcgcca caaattctaa | 1140 |

<210> SEQ ID NO 29
<211> LENGTH: 1077
<212> TYPE: DNA
<213> ORGANISM: Artificial sequence
<220> FEATURE:
<223> OTHER INFORMATION: porA mutant

<400> SEQUENCE: 29

| | | |
|---|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |
| actgaaagcc gcatcaggac gaaaatcagt gatttcggct cgtttatcgg ctttaagggg | 180 |
| agtgaggatt tgggcgacgg gctgaaggct gtttggcagc ttgagcaaga cgtatccgtt | 240 |
| gccggcggcg gcgcgaccca gtggggcaac agggaatcct ttatcggctt ggcaggcgaa | 300 |
| ttcggtacgc tgcgcgccgg tcgcgttgcg aatcagtttg acgatgccag ccaagccatt | 360 |
| gatccttggg acagcaataa tgatgtggct tcgcaattgg gtattttcaa cgccacgac | 420 |
| gacatgccgg tttccgtacg ctacgattcc ccgaattttt ccggtttcag cggcagcgtt | 480 |
| caattcgttc cgatccaaaa cagcaagtcc gcctatacgc cggctccggc tgttgtcggc | 540 |
| aagcccggat cggatgtgta ttatgccggt ctgaattaca aaaatggcgg ttttgccggg | 600 |
| aactatgcct ttaaatatgc gagacacgcc aatgtcggac gtaatgcttt tgagttgttc | 660 |
| ttgatcggca gcgggagtga tcaagccaaa ggtaccgatc ccttgaaaaa ccatcaggta | 720 |
| caccgtctga cgggcggcta tgaggaaggc ggcttgaatc tcgccttggc ggctcagttg | 780 |
| gatttgtctg aaaatggcga caaaaccaaa aacagtacga ccgaaattgc cgccactgct | 840 |
| tcctaccgct tcggtaatgc agttccacgc atcagctatg cccatggttt cgactttatc | 900 |
| gaacgcggta aaaaggcga aataccagc tacgatcaaa tcatcgccgg cgttgattat | 960 |
| gattttccca acgcacttc cgccatcgtg tctggcgctt ggctgaaacg caataccggc | 1020 |
| atcggcaact acactcaaat taatgccgcc tccgtcggtt tgcgccacaa attctaa | 1077 |

<210> SEQ ID NO 30
<211> LENGTH: 1014
<212> TYPE: DNA
<213> ORGANISM: Artificial sequence
<220> FEATURE:
<223> OTHER INFORMATION: porA mutant

<400> SEQUENCE: 30

| | | |
|---|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |

```
actgaaagcc gcatcaggac gaaaatcagt gatttcggct cgtttatcgg ctttaagggg     180
agtgaggatt tgggcgacgg gctgaaggct gtttggcagc ttgagcaaga cgtatccgtt     240
gccggcggcg gcgcgaccca gtggggcaac agggaatcct ttatcggctt ggcaggcgaa     300
ttcggtacgc tgcgcgccgg tcgcgttgcg aatcagtttg acgatgccag ccaagccatt     360
gatccttggg acagcaataa tgatgtggct tcgcaattgg gtattttcaa acgccacgac     420
gacatgccgg tttccgtacg ctacgattcc cccgaatttt ccggtttcag cggcagcgtt     480
caattcgttc cgatccaaaa cagcaagtcc gcctatacgc cggctccggc tgttgtcggc     540
aagcccggat cggatgtgta ttatgccggt ctgaattaca aaaatggcgg ttttgccggg     600
aactatgcct ttaaatatgc gagacacgcc aatgtcggat tgaaaaacca tcaggtacac     660
cgtctgacgg gcggctatga ggaaggcggc ttgaatctcg ccttggcggc tcagttggat     720
ttgtctgaaa atggcgacaa aaccaaaaac agtacgaccg aaattgccgc cactgcttcc     780
taccgcttcg gtaatgcagt tccacgcatc agctatgccc atggtttcga ctttatcgaa     840
cgcggtaaaa aaggcgaaaa taccagctac gatcaaatca tcgccggcgt tgattatgat     900
ttttccaaac gcacttccgc catcgtgtct ggcgcttggc tgaaacgcaa taccggcatc     960
ggcaactaca ctcaaattaa tgccgcctcc gtcggtttgc gccacaaatt ctaa          1014
```

<210> SEQ ID NO 31
<211> LENGTH: 1182
<212> TYPE: DNA
<213> ORGANISM: Artificial sequence
<220> FEATURE:
<223> OTHER INFORMATION: porA mutant

<400> SEQUENCE: 31

```
atgcgaaaaa aacttaccgc cctcgtattg tccgcactgc cgcttgcggc cgttgccgat      60
gtcagcctat acggcgaaat caaagccggc gtggaaggca ggaactacca gctgcaattg     120
actgaagcac aagccgctaa cggtggagcg agcggtcagg taaaagttac taaagttact     180
aaggccaaaa gccgcatcag gacgaaaatc agtgatttcg gctcgtttat cggctttaag     240
gggagtgagg atttgggcga cgggctgaag gctgtttggc agcttgagca agacgtatcc     300
gttgccggcg gcgcgcgcgac ccagtggggc aacagggaat cctttatcgg cttggcaggc     360
gaattcggta cgctgcgcgc cggtcgcgtt gcgaatcagt ttgacgatgc cagccaagcc     420
attgatcctt gggacagcaa taatgatgtg gcttcgcaat tgggtatttt caaacgccac     480
gacgacatgc cggtttccgt acgctacgat tccccgaat tttccggttt cagcggcagc     540
gttcaattcg ttccgatcca aaacagcaag tccgcctata cgccggcttt cgactttatc     600
gaacgcggta aaaaggcga aaataccagc cggctgttg tcggcaagcc cggatcggat     660
gtgtattatg ccggtctgaa ttacaaaaat ggcggttttg ccgggaacta tgcctttaaa     720
tatgcgagac acgccaatgt cggacgtaat gcttttgagt tgttcttgat cggcagcggg     780
agtgatcaag ccaaaggtac cgatcccttg aaaaaccatc aggtacaccg tctgacgggc     840
ggctatgagg aaggcggctt gaatctcgcc ttggcggctc agttggattt gtctgaaaat     900
ggcgacaaaa ccaaaaacag tacgaccgaa attgccgcca ctgcttccta ccgcttcggt     960
aatgcagttc cacgcatcag ctatgcccat ggtttcgact ttatcgaacg cggtaaaaaa    1020
ggcgaaaata ccagctacga tcaaatcatc gccggcgttg attatgattt ttccaaacgc    1080
acttccgcca tcgtgtctgg cgcttggctg aaacgcaata ccggcatcgg caactacact    1140
caaattaatg ccgcctccgt cggtttgcgc cacaaattct aa                       1182
```

<210> SEQ ID NO 32
<211> LENGTH: 1179
<212> TYPE: DNA
<213> ORGANISM: Artificial sequence
<220> FEATURE:
<223> OTHER INFORMATION: porA mutant

<400> SEQUENCE: 32

| | | | | | |
|---|---|---|---|---|---|
| atgcgaaaaa | aacttaccgc | cctcgtattg | tccgcactgc | cgcttgcggc | cgttgccgat | 60 |
| gtcagcctat | acggcgaaat | caaagccggc | gtggaaggca | ggaactacca | gctgcaattg | 120 |
| actgaagcac | aagccgctaa | cggtggagcg | agcggtcagg | taaaagttac | taaagttact | 180 |
| aaggccaaaa | gccgcatcag | gacgaaaatc | agtgatttcg | gctcgtttat | cggctttaag | 240 |
| gggagtgagg | atttgggcga | cgggctgaag | gctgtttggc | agcttgagca | agacgtatcc | 300 |
| gttgccggcg | gcggcgcgac | ccagtggggc | aacagggaat | cctttatcgg | cttggcaggc | 360 |
| gaattcggta | cgctgcgcgc | cggtcgcgtt | gcgaatcagt | ttgacgatgc | cagccaagcc | 420 |
| attgatcctt | gggacagcaa | taatgatgtg | gcttcgcaat | gggtattttt | caaacgccac | 480 |
| gacgacatgc | cggtttccgt | acgctacgat | cccccgaat | tttccggttt | cagcggcagc | 540 |
| gttcaattcg | ttccgatcca | aaacagcaag | tccgcctata | cgccggctaa | cgcaatacc | 600 |
| ggcatcggca | actacactca | aattaatccg | gctgttgtcg | gcaagcccgg | atcggatgtg | 660 |
| tattatgccg | gtctgaatta | caaaaatggc | ggttttgccg | gaactatgc | ctttaaatat | 720 |
| gcgagacacg | ccaatgtcgg | acgtaatgct | tttgagttgt | tcttgatcgg | cagcgggagt | 780 |
| gatcaagcca | aggtaccga | tcccttgaaa | aaccatcagg | tacaccgtct | gacgggcggc | 840 |
| tatgaggaag | gcggcttgaa | tctcgccttg | gcggctcagt | tggatttgtc | tgaaaatggc | 900 |
| gacaaaacca | aaaacagtac | gaccgaaatt | gccgccactg | cttcctaccg | cttcggtaat | 960 |
| gcagttccac | gcatcagcta | tgcccatggt | ttcgacttta | tcgaacgcgg | taaaaaaggc | 1020 |
| gaaaatacca | gctacgatca | aatcatcgcc | ggcgttgatt | atgattttc | caaacgcact | 1080 |
| tccgccatcg | tgtctggcgc | ttggctgaaa | cgcaataccg | gcatcggcaa | ctacactcaa | 1140 |
| attaatgccg | cctccgtcgg | tttgcgccac | aaattctaa | | | 1179 |

<210> SEQ ID NO 33
<211> LENGTH: 1119
<212> TYPE: DNA
<213> ORGANISM: Artificial sequence
<220> FEATURE:
<223> OTHER INFORMATION: porA mutant

<400> SEQUENCE: 33

| | | | | | |
|---|---|---|---|---|---|
| atgcgaaaaa | aacttaccgc | cctcgtattg | tccgcactgc | cgcttgcggc | cgttgccgat | 60 |
| gtcagcctat | acggcgaaat | caaagccggc | gtggaaggca | ggaactacca | gctgcaattg | 120 |
| actgaaagcc | gcatcaggac | gaaaatcagt | gatttcggct | cgtttatcgg | ctttaagggg | 180 |
| agtgaggatt | tgggcgacgg | gctgaaggct | gtttggcagc | ttgagcaaga | cgtatccgtt | 240 |
| gccggcggcg | gcgcgaccca | gtggggcaac | agggaatcct | ttatcggctt | ggcaggcgaa | 300 |
| ttcggtacgc | tgcgcgccgg | tcgcgttgcg | aatcagtttg | acgatgccag | ccaagccatt | 360 |
| gatccttggg | acagcaataa | tgatgtggct | tcgcaattgg | gtattttcaa | acgccacgac | 420 |
| gacatgccgg | tttccgtacg | ctacgattcc | ccgaattttt | ccggtttcag | cggcagcgtt | 480 |
| caattcgttc | cgatccaaaa | cagcaagtcc | gcctatacgc | cggctttcga | ctttatcgaa | 540 |

| | |
|---|---|
| cgcggtaaaa aaggcgaaaa taccagcccg gctgttgtcg gcaagcccgg atcggatgtg | 600 |
| tattatgccg gtctgaatta caaaaatggc ggttttgccg ggaactatgc ctttaaatat | 660 |
| gcgagacacg ccaatgtcgg acgtaatgct tctgagttgt tcttgatcgg cagcgggagt | 720 |
| gatcaagcca aagtaccga tcccttgaaa aaccatcagg tacaccgtct gacgggcggc | 780 |
| tatgaggaag gcggcttgaa tctcgccttg gcggctcagt tggatttgtc tgaaaacggc | 840 |
| gacaaaacca aaacagtac gaccgaaatt gccgccactg cttcctaccg cttcggtaat | 900 |
| gcagttccac gcatcagcta tgcccatggt ttcgacttta tcgaacgcgg taaaaaaggc | 960 |
| gaaaatacca gctacgatca aatcatcgcc ggcgttgatt atgatttttc caaacgcact | 1020 |
| tccgccatcg tgtctggcgc ttggctgaaa cgcaataccg gcatcggcaa ctacactcaa | 1080 |
| attaacgccg cctccgtcgg tttgcgccac aaattctaa | 1119 |

```
<210> SEQ ID NO 34
<211> LENGTH: 1116
<212> TYPE: DNA
<213> ORGANISM: Artificial sequence
<220> FEATURE:
<223> OTHER INFORMATION: porA mutant

<400> SEQUENCE: 34
```

| | |
|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |
| actgaaagcc gcatcaggac gaaaatcagt gatttcggct cgtttatcgg ctttaagggg | 180 |
| agtgaggatt tgggcgacgg gctgaaggct gtttggcagc ttgagcaaga cgtatccgtt | 240 |
| gccggcggcg cgcgacccca gtggggcaac agggaatcct ttatcggctt ggcaggcgaa | 300 |
| ttcggtacgc tgcgcgccgg tcgcgttgcg aatcagtttg acgatgccag ccaagccatt | 360 |
| gatccttggg acagcaataa tgatgtggct tcgcaattgg gtattttcaa acgccacgac | 420 |
| gacatgccgg tttccgtacg ctacgattcc ccgaattttt ccggtttcag cggcagcgtt | 480 |
| caattcgttc cgatccaaaa cagcaagtcc gcctatacgc cggctaaacg caataccggc | 540 |
| atcggcaact acactcaaat taatccggct gttgtcggca gcccggatc ggatgtgtat | 600 |
| tatgccggtc tgaattacaa aaatggcggt tttgccggga actatgcctt taaatatgcg | 660 |
| agacacgcca atgtcggacg taatgctttt gagttgttct tgatcggcag cgggagtgat | 720 |
| caagccaaag gtaccgatcc cttgaaaaac catcaggtac accgtctgac gggcggctat | 780 |
| gaggaaggcg gcttgaatct cgccttggcg gctcagttgg atttgtctga aaatggcgac | 840 |
| aaaaccaaaa acagtacgac cgaaattgcc gccactgctt cctaccgctt cggtaatgca | 900 |
| gttccacgca tcagctatgc ccatggtttc gactttatcg aacgcggtaa aaaggcgaa | 960 |
| aataccagct acgatcaaat catcgccggc gttgattatg attttccaa acgcacttcc | 1020 |
| gccatcgtgt ctggcgcttg gctgaaacgc aataccggca tcggcaacta cactcaaatt | 1080 |
| aatgccgcct ccgtcggttt gcgccacaaa ttctaa | 1116 |

```
<210> SEQ ID NO 35
<211> LENGTH: 1158
<212> TYPE: DNA
<213> ORGANISM: Artificial sequence
<220> FEATURE:
<223> OTHER INFORMATION: porA mutant

<400> SEQUENCE: 35
```

| | |
|---|---|
| atgcgaaaaa aacttaccgc cctcgtattg tccgcactgc cgcttgcggc cgttgccgat | 60 |

```
gtcagcctat acggcgaaat caaagccggc gtggaaggca ggaactacca gctgcaattg    120
actgaattcg actttatcga acgcggtaaa aaaggcgaaa ataccagcag ccgcatcagg    180
acgaaaatca gtgatttcgg ctcgtttatc ggctttaagg ggagtgagga tttgggcgac    240
gggctgaagg ctgtttggca gcttgagcaa gacgtatccg ttgccggcgg cggcgcgacc    300
cagtggggca acagggaatc ctttatcggc ttggcaggcg aattcggtac gctgcgcgcc    360
ggtcgcgttg cgaatcagtt tgacgatgcc agccaagcca ttgatccttg gacagcaat    420 aatgatgtgg cttcgcaatt gggtattttc aaacgccacg acgacatgcc ggtttccgta    480
cgctacgatt cccccgaatt ttccggtttc agcggcagcg ttcaattcgt tccgatccaa    540
aacagcaagt ccgcctatac gccggctaaa cgcaataccg gcatcggcaa ctacactcaa    600
attaatccgg ctgttgtcgg caagcccgga tcggatgtgt attatgccgg tctgaattac    660
aaaaatggcg gttttgccgg gaactatgcc tttaaatatg cgagacacgc caatgtcgga    720
cgtaatgctt ttgagttgtt cttgatcggc agcgggagtg atcaagccaa aggtaccgat    780
cccttgaaaa accatcaggt acaccgtctg acgggcggct atgaggaagg cggcttgaat    840
ctcgccttgg cggctcagtt ggatttgtct gaaaatggcg acaaaaccaa aaacagtacg    900
accgaaattg ccgccactgc ttcctaccgc ttcggtaatg cagttccacg catcagctat    960
gcccatggtt tcgactttat cgaacgcggt aaaaaaggcg aaaataccag ctacgatcaa   1020
atcatcgccg gcgttgatta tgattttcc aaacgcactt ccgccatcgt gtctggcgct   1080 tggctgaaaac gcaataccgg catcggcaac tacactcaaa ttaatgccgc ctccgtcggt   1140
ttgcgccaca aattctaa                                                  1158
```

<210> SEQ ID NO 36
<211> LENGTH: 1095
<212> TYPE: DNA
<213> ORGANISM: Artificial sequence
<220> FEATURE:
<223> OTHER INFORMATION: porA mutant

<400> SEQUENCE: 36

```
atgcgaaaaa aacttaccgc cctcgtattg tccgcactgc cgcttgcggc cgttgccgat     60
gtcagcctat acggcgaaat caaagccggc gtggaaggca ggaactacca gctgcaattg    120
actgaattcg actttatcga acgcggtaaa aaaggcgaaa ataccagcag ccgcatcagg    180
acgaaaatca gtgatttcgg ctcgtttatc ggctttaagg ggagtgagga tttgggcgac    240
gggctgaagg ctgtttggca gcttgagcaa gacgtatccg ttgccggcgg cggcgcgacc    300
cagtggggca acagggaatc ctttatcggc ttggcaggcg aattcggtac gctgcgcgcc    360
ggtcgcgttg cgaatcagtt tgacgatgcc agccaagcca ttgatccttg gacagcaat    420 aatgatgtgg cttcgcaatt gggtattttc aaacgccacg acgacatgcc ggtttccgta    480
cgctacgatt cccccgaatt ttccggtttc agcggcagcg ttcaattcgt tccgatccaa    540
aacagcaagt ccgcctatac gccggctaaa cgcaataccg gcatcggcaa ctacactcaa    600
attaatccgg ctgttgtcgg caagcccgga tcggatgtgt attatgccgg tctgaattac    660
aaaaatggcg gttttgccgg gaactatgcc tttaaatatg cgagacacgc caatgtcgga    720
ttgaaaaacc atcaggtaca ccgtctgacg gcggctatg aggaaggcgg cttgaatctc    780
gccttggcgg ctcagttgga tttgtctgaa aatggcgaca aaaccaaaaa cagtacgacc    840
gaaattgccg ccactgcttc ctaccgcttc ggtaatgcag ttccacgcat cagctatgcc    900
```

| | |
|---|---|
| catggtttcg actttatcga acgcggtaaa aaaggcgaaa ataccagcta cgatcaaatc | 960 |
| atcgccggcg ttgattatga ttttccaaa cgcacttccg ccatcgtgtc tggcgcttgg | 1020 |
| ctgaaacgca ataccggcat cggcaactac actcaaatta atgccgcctc cgtcggtttg | 1080 |
| cgccacaaat tctaa | 1095 |

<210> SEQ ID NO 37
<211> LENGTH: 990
<212> TYPE: DNA
<213> ORGANISM: Artificial sequence
<220> FEATURE:
<223> OTHER INFORMATION: porA mutant

<400> SEQUENCE: 37

| | |
|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |
| actgaaagcc gcatcaggac gaaaatcagt gatttcggct cgtttatcgg ctttaagggg | 180 |
| agtgaggatt tgggcgacgg gctgaaggct gtttggcagc ttgagcaaga cgtatccgtt | 240 |
| gccggcggcg gcgcgaccca gtggggcaac agggaatcct ttatcggctt ggcaggcgaa | 300 |
| ttcggtacgc tgcgcgccgg tcgcgttgcg aatcagtttg acgatgccag ccaagccatt | 360 |
| gatccttggg acagcaataa tgatgtggct tcgcaattgg gtattttcaa acgccacgac | 420 |
| gacatgccgg tttccgtacg ctacgattcc ccgaattt ccggtttcag cggcagcgtt | 480 |
| caattcgttc cgatccaaaa cagcaagtcc gcctatacgc cggctccggc tgttgtcggc | 540 |
| aagcccggat cggatgtgta ttatgccggt ctgaattaca aaaatggcgg ttttgccggg | 600 |
| aactatgcct ttaaatatgc gagacacgcc aatgtcggat tgaaaaacca tcaggtacac | 660 |
| cgtctgacgg gcggctatga ggaaggcggc ttgaatctcg ccttggcggc tcagttggat | 720 |
| ttgtctagta cgaccgaaat tgccgccact gcttcctacc gcttcggtaa tgcagttcca | 780 |
| cgcatcagct atgcccatgg tttcgacttt atcgaacgcg gtaaaaaagg cgaaaatacc | 840 |
| agctacgatc aaatcatcgc cggcgttgat tatgattttt ccaaacgcac ttccgccatc | 900 |
| gtgtctggcg cttggctgaa acgcaatacc ggcatcggca actacactca aattaatgcc | 960 |
| gcctccgtcg gtttgcgcca caaattctaa | 990 |

<210> SEQ ID NO 38
<211> LENGTH: 1221
<212> TYPE: DNA
<213> ORGANISM: Artificial sequence
<220> FEATURE:
<223> OTHER INFORMATION: porA mutant

<400> SEQUENCE: 38

| | |
|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |
| actgaagcac aagccgctaa cggtggagcg ttcgacttta tcgaacgcgg taaaaaaggc | 180 |
| gaaaatacca gcagcggtca ggtaaaagtt actaaagtta ctaaggccaa agccgcatc | 240 |
| aggacgaaaa tcagtgattt cggctcgttt atcggcttta aggggagtga ggatttgggc | 300 |
| gacgggctga aggctgtttg gcagcttgag caagacgtat ccgttgccgg cggcggcgcg | 360 |
| acccagtggg gcaacaggga atcctttatc ggcttggcag gcgaattcgg tacgctgcgc | 420 |
| gccggtcgcg ttgcgaatca gtttgacgat gccagccaag ccattgatcc ttgggacagc | 480 |
| aataatgatg tggcttcgca attgggtatt ttcaaacgcc acgacgacat gccggtttcc | 540 |

```
gtacgctacg attccccga atttccggt tcagcggca gcgttcaatt cgttccgatc      600
caaaacagca agtccgccta tacgccggct tattatacta agaatacaaa caataatctt   660
actctcgttc cggctgttgt cggcaagccc ggatcggatg tgtattatgc cggtctgaat   720
tacaaaaatg gcggttttgc cgggaactat gcctttaaat atgcgagaca cgccaatgtc   780
ggacgtaatg cttttgagtt gttcttgatc ggcagcggga gtgatcaagc caaaggtacc   840
gatcccttga aaaccatca ggtacaccgt ctgacgggcg ctatgagga aggcggcttg     900 aatctcgcct tggcggctca gttggatttg tctgaaaatg gcgacaaaac caaaaacagt   960
acgaccgaaa ttgccgccac tgcttcctac cgcttcggta tgcagttcc acgcatcagc   1020 tatgcccatg gtttcgactt tatcgaacgc ggtaaaaag gcgaaaatac cagctacgat   1080
caaatcatcg ccggcgttga ttatgatttt tccaaacgca cttccgccat cgtgtctggc  1140
gcttggctga aacgcaatac cggcatcggc aactacactc aaattaatgc cgcctccgtc  1200
ggtttgcgcc acaaattcta a                                             1221
```

<210> SEQ ID NO 39
<211> LENGTH: 1218
<212> TYPE: DNA
<213> ORGANISM: Artificial sequence
<220> FEATURE:
<223> OTHER INFORMATION: porA mutant

<400> SEQUENCE: 39

```
atgcgaaaaa aacttaccgc cctcgtattg tccgcactgc cgcttgcggc cgttgccgat    60
gtcagcctat acggcgaaat caaagccggc gtggaaggca ggaactacca gctgcaattg   120
actgaagcac aagccgctaa cggtggagcg agcggtcagg taaaagttac taaagttact   180
aaggccaaaa gccgcatcag gacgaaaatc agtgatttcg gctcgtttat cggctttaag   240
gggagtgagg atttgggcga cgggctgaag gctgtttggc agcttgagca agacgtatcc   300
gttgccggcg gcgcgcgac ccagtggggc aacagggaat cctttatcgg cttggcaggc   360
gaattcggta cgctgcgcgc cggtcgcgtt gcgaatcagt ttgacgatgc cagccaagcc   420
attgatcctt gggacagcaa taatgatgtg gcttcgcaat tgggtatttt caaacgccac   480
gacgacatgc cggtttccgt acgctacgat tcccccgaat tttccggttt cagcggcagc   540
gttcaattcg ttccgatcca aaacagcaag tccgcctata cgccggctta ttatactaag   600
aatacaaaca aacgcaatac cggcatcggc aactacactc aaattaataa taatcttact   660
ctcgttccgg ctgttgtcgg caagcccgga tcggatgtgt attatgccgg tctgaattac   720
aaaaatggcg gttttgccgg gaactatgcc tttaaatatg cgagacacgc caatgtcgga   780
cgtaatgctt ttgagttgtt cttgatcggc agcgggagtg atcaagccaa aggtaccgat   840
cccttgaaaa accatcaggt acaccgtctg acgggcggct atgaggaagg cggcttgaat   900
ctcgccttgg cggctcagtt ggatttgtct gaaaatggcg acaaaaccaa aaacagtacg   960
accgaaattg ccgccactgc ttcctaccgc ttcggtaatg cagttccacg catcagctat  1020
gcccatggtt tcgactttat cgaacgcggt aaaaaggcg aaaataccag ctacgatcaa   1080
atcatcgccg gcgttgatta tgattttccc aaacgcactt ccgccatcgt gtctggcgct  1140
tggctgaaac gcaataccgg catcggcaac tacactcaaa ttaatgccgc ctccgtcggt  1200
ttgcgccaca aattctaa                                                 1218
```

<210> SEQ ID NO 40

<211> LENGTH: 1260
<212> TYPE: DNA
<213> ORGANISM: Artificial sequence
<220> FEATURE:
<223> OTHER INFORMATION: porA mutant

<400> SEQUENCE: 40

| | |
|---|---|
| atgcgaaaaa aacttaccgc cctcgtattg tccgcactgc cgcttgcggc cgttgccgat | 60 |
| gtcagcctat acggcgaaat caaagccggc gtggaaggca ggaactacca gctgcaattg | 120 |
| actgaagcac aagccgctaa cggtggagcg ttcgacttta tcgaacgcgg taaaaaaggc | 180 |
| gaaaatacca gcagcggtca ggtaaaagtt actaaagtta ctaaggccaa agccgcatc | 240 |
| aggacgaaaa tcagtgattt cggctcgttt atcggcttta aggggagtga ggatttgggc | 300 |
| gacgggctga aggctgtttg gcagcttgag caagacgtat ccgttgccgg cggcggcgcg | 360 |
| acccagtggg gcaacaggga atcctttatc ggcttggcag gcgaattcgg tacgctgcgc | 420 |
| gccggtcgcg ttgcgaatca gtttgacgat gccagccaag ccattgatcc ttgggacagc | 480 |
| aataatgatg tggcttcgca attgggtatt ttcaaacgcc acgacgacat gccggtttcc | 540 |
| gtacgctacg attcccccga attttccggt ttcagcggca cgttcaattc gttccgatc | 600 |
| caaaacagca agtccgccta acgccggct tattatacta gaatacaaa caaacgcaat | 660 |
| accggcatcg gcaactacac tcaaattaat aataatctta ctctcgttcc ggctgttgtc | 720 |
| ggcaagcccg gatcggatgt gtattatgcc ggtctgaatt acaaaaatgg cggttttgcc | 780 |
| gggaactatg cctttaaata tgcgagacac gccaatgtcg acgtaatgc ttttgagttg | 840 |
| ttcttgatcg gcagcgggag tgatcaagcc aaaggtaccg atcccttgaa aaaccatcag | 900 |
| gtacaccgtc tgacgggcgg ctatgaggaa ggcggcttga atctcgcctt gcggctcag | 960 |
| ttggatttgt ctgaaaatgg cgacaaaacc aaaaacagta cgaccgaaat tgccgccact | 1020 |
| gcttcctacc gcttcggtaa tgcagttcca cgcatcagct atgcccatgg tttcgacttt | 1080 |
| atcgaacgcg gtaaaaaagg cgaaaatacc agctacgatc aaatcatcgc cggcgttgat | 1140 |
| tatgattttt ccaaacgcac ttccgccatc gtgtctggcg cttggctgaa acgcaatacc | 1200 |
| ggcatcggca actacactca aattaatgcc gcctccgtcg gtttgcgcca caaattctaa | 1260 |

<210> SEQ ID NO 41
<211> LENGTH: 1163
<212> TYPE: DNA
<213> ORGANISM: Artificial sequence
<220> FEATURE:
<223> OTHER INFORMATION: porA mutant

<400> SEQUENCE: 41

| | |
|---|---|
| atatgcgaaa aaacttacc gccctcgtat tgtccgcact gccgcttgcg gccgttgccg | 60 |
| atgtcagcct atacggcgaa atcaaagccg gcgtggaagg caggaactac cagctgcaat | 120 |
| tgactgaatt cgactttatc gaacgcggta aaaaggcga aataccagc agccgcatca | 180 |
| ggacgaaaat cagtgatttc ggctcgttta tcggctttaa ggggagtgag gatttgggcg | 240 |
| acgggctgaa ggctgtttgg cagcttgagc aagacgtatc cgttgccggc ggcggcgcga | 300 |
| cccagtgggg caacagggaa tcctttatcg gcttggcagg cgaattcggt acgctgcgcg | 360 |
| ccggtcgcgt tgcgaatcag tttgacgatg ccagccaagc cattgatcct tgggacagca | 420 |
| ataatgatgt ggcttcgcaa ttgggtattt tcaaacgcca cgacgacatg ccggtttccg | 480 |
| tacgctacga ttcccccgaa ttttccggtt tcagcggcag cgttcaattc gttccgatcc | 540 |
| aaaacagcaa gtccgcctat acgccggctt tcgactttat cgaacgcggt aaaaaaggcg | 600 |

```
aaaataccag cccggctgtt gtcggcaagc ccggatcgga tgtgtattat gccggtctga    660
attacaaaaa tggcggtttt gccgggaact atgcctttaa atatgcgaga cacgccaatg    720
tcggacgtaa tgcttttgag ttgttcttga tcggcagcgg gagtgatcaa gccaaaggta    780
ccgatccctt gaaaaaccat caggtacacc gtctgacggg cggctatgag gaaggcggct    840
tgaatctcgc cttggcggct cagttggatt tgtctgaaaa tggcgacaaa accaaaaaca    900
gtacgaccga aattgccgcc actgcttcct accgcttcgg taatgcagtt ccacgcatca    960
gctatgccca tggtttcgac tttatcgaac gcggtaaaaa aggcgaaaat accagctacg   1020
atcaaatcat cgccggcgtt gattatgatt tttccaaacg cacttccgcc atcgtgtctg   1080
gcgcttggct gaaacgcaat accggcatcg gcaactacac tcaaattaat gccgcctccg   1140
tcggtttgcg ccacaaattc taa                                           1163

<210> SEQ ID NO 42
<211> LENGTH: 1155
<212> TYPE: DNA
<213> ORGANISM: Artificial sequence
<220> FEATURE:
<223> OTHER INFORMATION: porA mutant

<400> SEQUENCE: 42
atgcgaaaaa aacttaccgc cctcgtattg tccgcactgc cgcttgcggc cgttgccgat     60
gtcagcctat acggcgaaat caaagccggc gtggaaggca ggaactacca gctgcaattg    120
actgaaaaac gcaataccgg catcggcaac tacactcaaa ttaatagccg catcaggacg    180
aaaatcagtg atttcggctc gtttatcggc tttaagggga gtgaggattt gggcgacggg    240
ctgaaggctg tttggcagct tgagcaagac gtatccgttg ccggcggcgg cgcgacccag    300
tggggcaaca gggaatcctt tatcggcttg gcaggcgaat tcggtacgct gcgcgccggt    360
cgcgttgcga atcagtttga cgatgccagc caagccattg atccttggga cagcaataat    420
gatgtggctt cgcaattggg tattttcaaa cgccacgacg acatgccggt ttccgtacgc    480
tacgattccc ccgaattttc cggtttcagc ggcagcgttc aattcgttcc gatccaaaac    540
agcaagtccg cctatacgcc ggctaaacgc aataccggca tcgcaactac cactcaaatt    600
aatccggctg ttgtcggcaa gcccggatcg gatgtgtatt atgccggtct gaattacaaa    660
aatggcggtt ttgccgggaa ctatgccttt aaatatgcga gacacgccaa tgtcggacgt    720
aatgcttttg agttgttctt gatcggcagc gggagtgatc aagccaaagg taccgatccc    780
ttgaaaaacc atcaggtaca ccgtctgacg ggcggctatg aggaaggcgg cttgaatctc    840
gccttggcgg ctcagttgga tttgtctgaa aatggcgaca aaaccaaaaa cagtacgacc    900
gaaattgccg ccactgcttc ctaccgcttc ggtaatgcag ttccacgcat cagctatgcc    960
catggtttcg actttatcga acgcggtaaa aaaggcgaaa ataccagcta cgatcaaatc   1020
atcgccggcg ttgattatga tttttccaaa cgcacttccg ccatcgtgtc tggcgcttgg   1080
ctgaaacgca ataccggcat cggcaactac actcaaatta atgccgcctc cgtcggtttg   1140
cgccacaaat tctaa                                                    1155

<210> SEQ ID NO 43
<211> LENGTH: 1158
<212> TYPE: DNA
<213> ORGANISM: Artificial sequence
<220> FEATURE:
<223> OTHER INFORMATION: porA mutant
```

-continued

```
<400> SEQUENCE: 43
atgcgaaaaa aacttaccgc cctcgtattg tccgcactgc cgcttgcggc cgttgccgat      60
gtcagcctat acggcgaaat caaagccggc gtggaaggca ggaactacca gctgcaattg     120
actgaaaaac gcaataccgg catcggcaac tacactcaaa ttaatagccg catcaggacg     180
aaaatcagtg atttcggctc gtttatcggc tttaagggga gtgaggattt gggcgacggg     240
ctgaaggctg tttggcagct tgagcaaaac gtatccgttg ccggcggcgg cgcgacccag     300
tggggcaaca gggaatcctt tatcggcttg gcaggcgaat cggtacgct gcgcgccggt      360 cgcgttgcga atcagtttga cgatgccagc caagccattg atccttggga cagcaataat     420
gatgtggctt cgcaattggg tatttcaaa cgccacgacg acatgccggt ttccgtacgc      480
tacgattccc ccgaattttc cggtttcagc ggcagcgttc aattcgttcc gatccaaaac     540
agcaagtccg cctatacgcc ggctttcgac tttatcgaac gcggtaaaaa aggcgaaaat     600
accagcccgg ctgttgtcgg caagcccgga tcggatgtgt attatgccgg tctgaattac     660
aaaaatggcg gttttgccgg gaactatgcc tttaaatatg cgagacacgc caatgtcgga     720
cgtaatgctt ttgagttgtt cttgatcggc agcgggagtg atcaagccaa aggtaccgat     780
cccttgaaaa accatcaggt acaccgtctg acgggcggct atgaggaagg cggcttgaat     840
ctcgccttgg cggctcagtt ggatttgtct gaaaatggcg acaaaaccaa aaacagtacg     900
accgaaattg ccgccactgc ttcctaccgc ttcggtaatg cagttccacg catcagctat     960
gcccatggtt tcgactttat cgaacgcggt aaaaaaggcg aaaataccag ctacgatcaa    1020
atcatcgccg gcgttgatta tgattttttcc aaacgcactt ccgccatcgt gtctggcgct    1080
tggctgaaac gcaataccgg catcggcaac tacactcaaa ttaatgccgc ctccgtcggt    1140
ttgcgccaca aattctaa                                                  1158

<210> SEQ ID NO 44
<211> LENGTH: 1179
<212> TYPE: DNA
<213> ORGANISM: Neisseria meningitidis

<400> SEQUENCE: 44
atgcgaaaaa aacttaccgc cctcgtattg tccgcactgc cgcttgcggc cgttgccgat      60
gtcagcctat acggcgaaat caaagccggc gtggaaggca ggaactacca gctgcaattg     120
actgaagcac aagccgctaa cggtggagcg agcggtcagg taaaagttac taaagttact     180
aaggccaaaa gccgcatcag gacgaaaatc agtgatttcg gctcgtttat cggctttaag     240
gggagtgagg atttgggcga cgggctgaag gctgtttggc agcttgagca agacgtatcc     300
gttgccggcg gcgcgcgac ccagtggggc aacagggaat cctttatcgg cttggcaggc     360
gaattcggta cgctgcgcgc cggtcgcgtt gcgaatcagt ttgacgatgc cagccaagcc     420
attgatcctt gggacagcaa taatgatgtg gcttcgcaat gggtatttt caaacgccac     480 gacgacatgc cggtttccgt acgctacgat tcccccgaat tttccggttt cagcggcagc     540
gttcaattcg ttccgatcca aaacagcaag tccgcctata cgccggctta ttatactaag     600
aatacaaaca ataatcttac tctcgttccg gctgttgtcg gcaagcccgg atcggatgtg     660
tattatgccg gtctgaatta caaaaatggc ggttttgccg ggaactatgc ctttaaatat     720
gcgagacacg ccaatgtcgg acgtaatgct tttgagttgt tcttgatcgg cagcgggagt     780
gatcaagcca aaggtaccga tcccttgaaa accatcaggt acaccgtctg acgggcggc     840 tatgaggaag gcggcttgaa tctcgccttg gcggctcagt tggatttgtc tgaaaatggc     900
```

-continued

```
gacaaaacca aaaacagtac gaccgaaatt gccgccactg cttcctaccg cttcggtaat    960
gcagttccac gcatcagcta tgcccatggt ttcgacttta tcgaacgcgg taaaaaaggc   1020
gaaaatacca gctacgatca aatcatcgcc ggcgttgatt atgattttc caaacgcact    1080
tccgccatcg tgtctggcgc ttggctgaaa cgcaataccg gcatcggcaa ctacactcaa   1140
attaatgccg cctccgtcgg tttgcgccac aaattctaa                          1179
```

<210> SEQ ID NO 45
<211> LENGTH: 20
<212> TYPE: PRT
<213> ORGANISM: Neisseria meningitidis

<400> SEQUENCE: 45

Ala Gln Ala Ala Asn Gly Gly Ala Ser Gly Gln Val Lys Val Thr Lys
1               5                   10                  15

Val Thr Lys Ala
            20

<210> SEQ ID NO 46
<211> LENGTH: 14
<212> TYPE: PRT
<213> ORGANISM: Neisseria meningitidis

<400> SEQUENCE: 46

Tyr Tyr Thr Lys Asn Thr Asn Asn Asn Leu Thr Leu Val Pro
1               5                   10

<210> SEQ ID NO 47
<211> LENGTH: 42
<212> TYPE: PRT
<213> ORGANISM: Nesserie meningitidis

<400> SEQUENCE: 47

Val Glu Gly Arg Asn Tyr Gln Leu Gln Leu Thr Glu Ala Gln Ala Ala
1               5                   10                  15

Asn Gly Gly Ala Ser Gly Gln Val Lys Val Thr Lys Val Thr Lys Ala
            20                  25                  30

Lys Arg Lys Ser Arg Ile Arg Thr Lys Ile
        35                  40

<210> SEQ ID NO 48
<211> LENGTH: 13
<212> TYPE: PRT
<213> ORGANISM: Nesseria meningitidis

<400> SEQUENCE: 48

Val Ser Val Gly Gly Gly Ala Thr Gln Trp Gly Asn Arg
1               5                   10

<210> SEQ ID NO 49
<211> LENGTH: 26
<212> TYPE: PRT
<213> ORGANISM: Nesseria meningitidis

<400> SEQUENCE: 49

Ala Ser Gln Ala Ile Asp Pro Trp Asp Ser Asn Asn Asp Val Ala Ser
1               5                   10                  15

Gln Leu Gly Ile Phe Lys Arg His Asp Asp
            20                  25

```
<210> SEQ ID NO 50
<211> LENGTH: 34
<212> TYPE: PRT
<213> ORGANISM: Neisseria meningitidis

<400> SEQUENCE: 50

Pro Ile Gln Asn Ser Lys Ser Ala Tyr Thr Pro Ala Tyr Tyr Thr Lys
1               5                   10                  15

Asn Thr Asn Asn Asn Leu Thr Leu Val Pro Ala Val Val Gly Lys Pro
            20                  25                  30

Gly Ser

<210> SEQ ID NO 51
<211> LENGTH: 31
<212> TYPE: PRT
<213> ORGANISM: Neisseria meningitidis

<400> SEQUENCE: 51

Arg His Ala Asn Val Gly Arg Asp Ala Phe Glu Leu Phe Leu Leu Gly
1               5                   10                  15

Ser Gly Ser Asp Gln Ala Lys Gly Thr Asp Pro Leu Lys Asn His
            20                  25                  30

<210> SEQ ID NO 52
<211> LENGTH: 14
<212> TYPE: PRT
<213> ORGANISM: Neisseria meningitidis

<400> SEQUENCE: 52

Leu Ser Glu Asn Gly Asp Lys Thr Lys Asn Ser Thr Thr Glu
1               5                   10

<210> SEQ ID NO 53
<211> LENGTH: 14
<212> TYPE: PRT
<213> ORGANISM: Neisseria meningitidis

<400> SEQUENCE: 53

Phe Asp Leu Ile Glu Arg Gly Lys Lys Gly Glu Asn Thr Ser
1               5                   10

<210> SEQ ID NO 54
<211> LENGTH: 13
<212> TYPE: PRT
<213> ORGANISM: Neisseria meningitidis

<400> SEQUENCE: 54

Lys Arg Asn Thr Gly Ile Gly Asn Tyr Thr Gln Ile Asn
1               5                   10

<210> SEQ ID NO 55
<211> LENGTH: 19
<212> TYPE: DNA
<213> ORGANISM: Artificial sequence
<220> FEATURE:
<223> OTHER INFORMATION: PCR primer

<400> SEQUENCE: 55
gttcggtcgt ttccgataa                                              19

<210> SEQ ID NO 56
<211> LENGTH: 20
<212> TYPE: DNA
<213> ORGANISM: Artificial sequence
```

<220> FEATURE:
<223> OTHER INFORMATION: PCR Primer

<400> SEQUENCE: 56
tttgaaaccc tgaccctctg                                              20

<210> SEQ ID NO 57
<211> LENGTH: 40
<212> TYPE: DNA
<213> ORGANISM: Artificial sequence
<220> FEATURE:
<223> OTHER INFORMATION: PCR primer

<400> SEQUENCE: 57
tatacccggg tcgcatatcg gcttcctttt gtaaatttga                        40

<210> SEQ ID NO 58
<211> LENGTH: 24
<212> TYPE: DNA
<213> ORGANISM: Artificial sequence
<220> FEATURE:
<223> OTHER INFORMATION: PCR primer

<400> SEQUENCE: 58
tccgtcggtt tgcgccacaa attc                                         24

<210> SEQ ID NO 59
<211> LENGTH: 29
<212> TYPE: DNA
<213> ORGANISM: Artificial sequence
<220> FEATURE:
<223> OTHER INFORMATION: PCR primer

<400> SEQUENCE: 59
gtgaaaaggc ctgatcccgt cgttttaca                                    29

<210> SEQ ID NO 60
<211> LENGTH: 33
<212> TYPE: DNA
<213> ORGANISM: Artificial sequence
<220> FEATURE:
<223> OTHER INFORMATION: PCR primer

<400> SEQUENCE: 60
gtgaaaaggc ctcaattctg attagaaaaa ctc                               33

<210> SEQ ID NO 61
<211> LENGTH: 22
<212> TYPE: DNA
<213> ORGANISM: Artificial sequence
<220> FEATURE:
<223> OTHER INFORMATION: PCR primer

<400> SEQUENCE: 61
ctggtagttc ctgccttcca cg                                           22

<210> SEQ ID NO 62
<211> LENGTH: 21
<212> TYPE: DNA
<213> ORGANISM: Artificial sequence
<220> FEATURE:
<223> OTHER INFORMATION: PCR primer

<400> SEQUENCE: 62
agccaagccg ctaacggtgg a                                            21

```
<210> SEQ ID NO 63
<211> LENGTH: 23
<212> TYPE: DNA
<213> ORGANISM: Artificial sequence
<220> FEATURE:
<223> OTHER INFORMATION: PCR primer

<400> SEQUENCE: 63
gatcggaacg aattgaacgc tgc                                           23

<210> SEQ ID NO 64
<211> LENGTH: 20
<212> TYPE: DNA
<213> ORGANISM: Artificial sequence
<220> FEATURE:
<223> OTHER INFORMATION: PCR primer

<400> SEQUENCE: 64
gttgtcggca agcccggatc                                               20

<210> SEQ ID NO 65
<211> LENGTH: 21
<212> TYPE: DNA
<213> ORGANISM: Artificial sequence
<220> FEATURE:
<223> OTHER INFORMATION: PCR primer

<400> SEQUENCE: 65
tccgacattg gcgtgtctcg c                                             21

<210> SEQ ID NO 66
<211> LENGTH: 27
<212> TYPE: DNA
<213> ORGANISM: Artificial sequence
<220> FEATURE:
<223> OTHER INFORMATION: PCR primer

<400> SEQUENCE: 66
ttgaaaaacc atcaggtaca ccgtctg                                       27

<210> SEQ ID NO 67
<211> LENGTH: 27
<212> TYPE: DNA
<213> ORGANISM: Artificial sequence
<220> FEATURE:
<223> OTHER INFORMATION: PCR primer

<400> SEQUENCE: 67
ttcagtcaat tgcagctggt agttcct                                       27

<210> SEQ ID NO 68
<211> LENGTH: 21
<212> TYPE: DNA
<213> ORGANISM: Artificial sequence
<220> FEATURE:
<223> OTHER INFORMATION: PCR primer

<400> SEQUENCE: 68
agccaagccg ctaacggtgg a                                             21

<210> SEQ ID NO 69
<211> LENGTH: 21
<212> TYPE: DNA
<213> ORGANISM: Artificial sequence
<220> FEATURE:
<223> OTHER INFORMATION: PCR primer
```

<400> SEQUENCE: 69
tccgacattg gcgtgtctcg c                                    21

<210> SEQ ID NO 70
<211> LENGTH: 27
<212> TYPE: DNA
<213> ORGANISM: Artificial sequence
<220> FEATURE:
<223> OTHER INFORMATION: PCR primer

<400> SEQUENCE: 70
ttgaaaaacc atcaggtaca ccgtctg                              27

<210> SEQ ID NO 71
<211> LENGTH: 24
<212> TYPE: DNA
<213> ORGANISM: Artificial sequence
<220> FEATURE:
<223> OTHER INFORMATION: PCR primer

<400> SEQUENCE: 71
agacaaatcc aactgagccg ccaa                                 24

<210> SEQ ID NO 72
<211> LENGTH: 24
<212> TYPE: DNA
<213> ORGANISM: Artificial sequence
<220> FEATURE:
<223> OTHER INFORMATION: PCR primer

<400> SEQUENCE: 72
agtacgaccg aaattgccgc cact                                 24

<210> SEQ ID NO 73
<211> LENGTH: 42
<212> TYPE: DNA
<213> ORGANISM: Artificial sequence
<220> FEATURE:
<223> OTHER INFORMATION: PCR primer

<400> SEQUENCE: 73
accgcgttcg ataaagtcga aagccggcgt ataggcggac tt             42

<210> SEQ ID NO 74
<211> LENGTH: 40
<212> TYPE: DNA
<213> ORGANISM: Artificial sequence
<220> FEATURE:
<223> OTHER INFORMATION: PCR primer

<400> SEQUENCE: 74
aaaaaaggcg aaaataccag cccggctgtt gtcggcaagc                40

<210> SEQ ID NO 75
<211> LENGTH: 36
<212> TYPE: DNA
<213> ORGANISM: Artificial sequence
<220> FEATURE:
<223> OTHER INFORMATION: PCR primer

<400> SEQUENCE: 75
gccggtattg cgtttagccg gcgtataggc ggactt                    36

<210> SEQ ID NO 76

<211> LENGTH: 43
<212> TYPE: DNA
<213> ORGANISM: Artificial sequence
<220> FEATURE:
<223> OTHER INFORMATION: PCR primer

<400> SEQUENCE: 76
atcggcaact acactcaaat taatccggct gttgtcggca agc                    43

<210> SEQ ID NO 77
<211> LENGTH: 48
<212> TYPE: DNA
<213> ORGANISM: Artificial sequence
<220> FEATURE:
<223> OTHER INFORMATION: PCR primer

<400> SEQUENCE: 77
accgcgttcg ataaagtcga attcagtcaa ttgcagctgg tagttcct               48

<210> SEQ ID NO 78
<211> LENGTH: 42
<212> TYPE: DNA
<213> ORGANISM: Artificial sequence
<220> FEATURE:
<223> OTHER INFORMATION: PCR primer

<400> SEQUENCE: 78
aaaaaaggcg aaaataccag cagccaagcc gctaacggtg ga                     42

<210> SEQ ID NO 79
<211> LENGTH: 21
<212> TYPE: DNA
<213> ORGANISM: Artificial sequence
<220> FEATURE:
<223> OTHER INFORMATION: PCR primer

<400> SEQUENCE: 79
tccgacattg gcgtgtctcg c                                            21

<210> SEQ ID NO 80
<211> LENGTH: 27
<212> TYPE: DNA
<213> ORGANISM: Artificial sequence
<220> FEATURE:
<223> OTHER INFORMATION: PCR primer

<400> SEQUENCE: 80
ttgaaaaacc atcaggtaca ccgtctg                                      27

<210> SEQ ID NO 81
<211> LENGTH: 45
<212> TYPE: DNA
<213> ORGANISM: Artificial sequence
<220> FEATURE:
<223> OTHER INFORMATION: PCR primer

<400> SEQUENCE: 81
accgcgttcg ataaagtcga acgctccacc gttagcggct tgtgc                  45

<210> SEQ ID NO 82
<211> LENGTH: 54
<212> TYPE: DNA
<213> ORGANISM: Artificial sequence
<220> FEATURE:
<223> OTHER INFORMATION: PCR primer

<400> SEQUENCE: 82
aaaaaaggcg aaaataccag cagcggtcag gtaaaagtta ctaaagttac taag            54

<210> SEQ ID NO 83
<211> LENGTH: 39
<212> TYPE: DNA
<213> ORGANISM: Artificial sequence
<220> FEATURE:
<223> OTHER INFORMATION: PCR primer

<400> SEQUENCE: 83
gccggtattg cgtttgtttg tattcttagt ataataagc                             39

<210> SEQ ID NO 84
<211> LENGTH: 51
<212> TYPE: DNA
<213> ORGANISM: Artificial sequence
<220> FEATURE:
<223> OTHER INFORMATION: PCR primer

<400> SEQUENCE: 84
atcggcaact acactcaaat taataacaat cttactctcg ttccggctgt t               51

<210> SEQ ID NO 85
<211> LENGTH: 361
<212> TYPE: PRT
<213> ORGANISM: Neisseria meningitidis

<400> SEQUENCE: 85

Glu Gly Arg Asn Tyr Gln Leu Gln Leu Thr Glu Ala Gln Ala Ala Asn
1               5                   10                  15

Gly Gly Ala Ser Gly Gln Val Lys Val Thr Lys Val Thr Lys Ala Lys
                20                  25                  30

Ser Arg Ile Arg Thr Lys Ile Ser Asp Phe Gly Ser Phe Ile Gly Phe
            35                  40                  45

Lys Gly Ser Glu Asp Leu Gly Asp Gly Leu Lys Ala Val Trp Gln Leu
        50                  55                  60

Glu Gln Asp Val Ser Val Ala Gly Gly Ala Thr Gln Trp Gly Asn
65                  70                  75                  80

Arg Glu Ser Phe Ile Gly Leu Ala Gly Glu Phe Gly Thr Leu Arg Ala
                85                  90                  95

Gly Arg Val Ala Asn Gln Phe Asp Asp Ala Ser Gln Ala Ile Asp Pro
            100                 105                 110

Trp Asp Ser Asn Asn Asp Val Ala Ser Gln Leu Gly Ile Phe Lys Arg
        115                 120                 125

His Asp Asp Met Pro Val Ser Val Arg Tyr Asp Ser Pro Glu Phe Ser
    130                 135                 140

Gly Phe Ser Gly Ser Val Gln Phe Val Pro Ile Gln Asn Ser Lys Ser
145                 150                 155                 160

Ala Tyr Thr Pro Ala Tyr Tyr Thr Lys Asn Thr Asn Asn Leu Thr
                165                 170                 175

Leu Val Pro Ala Val Val Gly Lys Pro Gly Ser Asp Val Tyr Tyr Ala
            180                 185                 190

Gly Leu Asn Tyr Lys Asn Gly Phe Ala Gly Asn Tyr Ala Phe Lys
        195                 200                 205

Tyr Ala Arg His Ala Asn Val Gly Arg Asn Ala Phe Glu Leu Phe Leu
    210                 215                 220

Ile Gly Ser Gly Ser Asp Gln Ala Lys Gly Thr Asp Pro Leu Lys Asn
225                 230                 235                 240

His Gln Val His Arg Leu Thr Gly Gly Tyr Glu Gly Gly Leu Asn
            245                 250                 255

Leu Ala Leu Ala Ala Gln Leu Asp Leu Ser Glu Asn Gly Asp Lys Thr
        260                 265                 270

Lys Asn Ser Thr Thr Glu Ile Ala Ala Thr Ala Ser Tyr Arg Phe Gly
            275                 280                 285

Asn Ala Val Pro Arg Ile Ser Tyr Ala His Gly Phe Asp Phe Ile Glu
        290                 295                 300

Arg Gly Lys Lys Gly Glu Asn Thr Ser Tyr Asp Gln Ile Ile Ala Gly
305                 310                 315                 320

Val Asp Tyr Asp Phe Ser Lys Arg Thr Ser Ala Ile Val Ser Gly Ala
                325                 330                 335

Trp Leu Lys Arg Asn Thr Gly Ile Gly Asn Tyr Thr Gln Ile Asn Ala
            340                 345                 350

Ala Ser Val Gly Leu Arg His Lys Phe
            355                 360

<210> SEQ ID NO 86
<211> LENGTH: 350
<212> TYPE: PRT
<213> ORGANISM: Neisseria meningitidis

<400> SEQUENCE: 86

Glu Gly Asn Asn Ile Gln Leu Gln Leu Thr Glu Pro Pro Ser Lys Gly
1               5                   10                  15

Gln Thr Gly Asn Lys Val Thr Lys Gly Lys Ser Arg Ile Arg Thr Lys
            20                  25                  30

Ile Asn Asp Phe Gly Ser Phe Ile Gly Phe Lys Gly Ser Glu Asp Leu
        35                  40                  45

Gly Glu Gly Leu Lys Ala Val Trp Gln Leu Glu Gln Asp Val Ser Val
    50                  55                  60

Ala Gly Gly Gly Ala Thr Gln Trp Gly Asn Arg Glu Ser Phe Ile Gly
65                  70                  75                  80

Leu Ala Gly Glu Phe Gly Thr Leu Arg Ala Gly Arg Val Ala Asn Gln
                85                  90                  95

Phe Asp Asp Ala Ser Gln Ala Ile Asp Pro Trp Asp Ser Asn Asn Asp
            100                 105                 110

Val Ala Ser Gln Leu Gly Ile Phe Lys Arg His Asp Asp Met Pro Val
        115                 120                 125

Ser Val Arg Tyr Asp Ser Pro Asp Phe Ser Gly Phe Ser Gly Ser Val
    130                 135                 140

Gln Phe Val Pro Ala Gln Asn Ser Lys Ser Ala Tyr Thr Pro Ala Thr
145                 150                 155                 160

Tyr Thr Val Asp Ser Ser Gly Val Val Thr Pro Val Pro Ala Val Val
                165                 170                 175

Gly Lys Pro Gly Ser Asp Val Tyr Tyr Ala Gly Leu Asn Tyr Lys Asn
            180                 185                 190

Gly Gly Phe Ala Gly Asn Tyr Ala Phe Lys Tyr Ala Lys His Ala Asn
        195                 200                 205

Val Gly Arg Asp Ala Phe Asn Leu Phe Leu Gly Arg Ile Gly Glu
    210                 215                 220

Gly Asp Glu Ala Lys Gly Thr Asp Pro Leu Lys Asn His Gln Val His
225                 230                 235                 240

Arg Leu Thr Gly Gly Tyr Glu Glu Gly Gly Leu Asn Leu Ala Leu Ala

-continued

```
            245                 250                 255
Ala Gln Leu Asp Leu Ser Glu Asn Gly Asp Lys Thr Lys Asn Ser Thr
            260                 265                 270

Thr Glu Ile Ala Ala Thr Ala Ser Tyr Arg Phe Gly Asn Ala Val Pro
        275                 280                 285

Arg Ile Ser Tyr Ala His Gly Phe Asp Phe Ile Glu Arg Gly Lys Lys
    290                 295                 300

Gly Glu His Thr Ser Tyr Asp Gln Ile Ile Ala Gly Val Asp Tyr Asp
305                 310                 315                 320

Phe Ser Lys Arg Thr Ser Ala Ile Val Ser Gly Ala Trp Leu Lys Arg
                325                 330                 335

Asn Thr Gly Ile Gly Asn Tyr Thr Gln Ile Asn Ala Ala Ser
                340                 345                 350

<210> SEQ ID NO 87
<211> LENGTH: 355
<212> TYPE: PRT
<213> ORGANISM: Neisseria meningitidis

<400> SEQUENCE: 87

Glu Gly Arg Asn Ile Gln Leu Gln Leu Thr Glu Pro Leu Gln Asn Ile
1               5                   10                  15

Gln Gln Pro Gln Val Thr Lys Arg Lys Ser Arg Ile Arg Thr Lys Ile
            20                  25                  30

Ser Asp Phe Gly Ser Phe Ile Gly Phe Lys Gly Ser Glu Asp Leu Gly
        35                  40                  45

Glu Gly Leu Lys Ala Val Trp Gln Leu Glu Gln Asp Val Ser Val Ala
    50                  55                  60

Gly Gly Gly Ala Thr Arg Trp Gly Asn Arg Glu Ser Phe Val Gly Leu
65                  70                  75                  80

Ala Gly Glu Phe Gly Thr Leu Arg Ala Gly Arg Val Ala Asn Gln Phe
                85                  90                  95

Asp Asp Ala Ser Lys Ala Ile Asp Pro Trp Asp Ser Asn Asn Val Val
            100                 105                 110

Ala Ser Gln Leu Gly Ile Phe Lys Arg His Asp Asp Met Pro Val Ser
        115                 120                 125

Val Arg Tyr Asp Ser Pro Glu Phe Ser Gly Phe Ser Gly Ser Val Gln
    130                 135                 140

Phe Val Pro Ala Gln Asn Ser Lys Ser Ala Tyr Thr Pro Ala His Phe
145                 150                 155                 160

Val Gln Gln Thr Pro Gln Ser Gln Pro Thr Leu Val Pro Ala Val Val
                165                 170                 175

Gly Lys Pro Gly Ser Asp Val Tyr Tyr Ala Gly Leu Asn Tyr Lys Asn
            180                 185                 190

Gly Gly Phe Ala Gly Asn Tyr Ala Phe Lys Tyr Ala Lys His Ala Asn
        195                 200                 205

Val Gly Arg Asp Ala Phe Glu Leu Phe Leu Leu Gly Ser Gly Ser Asp
    210                 215                 220

Glu Ala Lys Gly Thr Asp Pro Leu Lys Asn His Gln Val His Arg Leu
225                 230                 235                 240

Thr Gly Gly Tyr Glu Glu Gly Gly Leu Asn Leu Ala Leu Ala Ala Gln
                245                 250                 255

Leu Asp Leu Ser Glu Asn Ala Asp Lys Thr Lys Asn Ser Thr Thr Glu
            260                 265                 270
```

```
Ile Ala Ala Thr Ala Ser Tyr Arg Phe Gly Asn Ala Val Pro Arg Ile
            275                 280                 285

Ser Tyr Ala His Gly Phe Asp Phe Ile Glu Arg Gly Lys Lys Gly Glu
    290                 295                 300

Asn Thr Ser Tyr Asp Gln Ile Ile Ala Gly Val Asp Tyr Asp Phe Ser
305                 310                 315                 320

Lys Arg Thr Ser Ala Ile Val Ser Gly Ala Trp Leu Lys Arg Asn Thr
                325                 330                 335

Gly Ile Gly Asn Tyr Thr Gln Ile Asn Ala Ala Ser Val Gly Leu Arg
            340                 345                 350

His Lys Phe
        355

<210> SEQ ID NO 88
<211> LENGTH: 388
<212> TYPE: PRT
<213> ORGANISM: Neisseria meningitidis

<400> SEQUENCE: 88

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
                20                  25                  30

Gly Asn Asn Ile Gln Leu Gln Leu Thr Glu Pro Pro Ser Gln Gly Gln
            35                  40                  45

Thr Gly Asn Lys Val Thr Lys Gly Lys Ser Arg Ile Arg Thr Lys Ile
    50                  55                  60

Ser Asp Phe Gly Ser Phe Ile Gly Phe Arg Gly Ser Glu Asp Leu Gly
65                  70                  75                  80

Glu Gly Leu Lys Ala Val Trp Gln Leu Glu Gln Asp Val Ser Val Ala
                85                  90                  95

Gly Gly Gly Ala Thr Gln Trp Gly Asn Arg Glu Ser Phe Ile Gly Leu
            100                 105                 110

Ala Gly Glu Phe Gly Thr Leu Arg Ala Gly Arg Val Ala Asn Gln Phe
        115                 120                 125

Asp Asp Ala Ser Gln Ala Ile Asp Pro Trp Asp Ser Asn Asn Asp Val
130                 135                 140

Ala Ser Gln Leu Gly Ile Phe Lys Arg His Asp Asp Met Pro Val Ser
145                 150                 155                 160

Val Arg Tyr Asp Ser Pro Glu Phe Ser Gly Phe Ser Gly Ser Val Gln
                165                 170                 175

Phe Val Pro Ala Gln Asn Ser Lys Ser Ala Tyr Thr Pro Ala Thr Leu
            180                 185                 190

Ala Asn Gly Ala Asn Asn Thr Ile Ile Arg Val Pro Ala Val Val Gly
        195                 200                 205

Lys Pro Gly Ser Asp Val Tyr Tyr Ala Gly Leu Asn Tyr Lys Asn Gly
    210                 215                 220

Gly Phe Ala Gly Asn Tyr Ala Phe Lys Tyr Ala Arg His Ala Asn Val
225                 230                 235                 240

Gly Arg Asp Ala Phe Asn Leu Phe Leu Leu Gly Arg Ile Gly Asp Asp
                245                 250                 255

Asp Glu Ala Lys Gly Thr Asp Pro Leu Lys Asn His Gln Val His Arg
            260                 265                 270

Leu Thr Ser Gly Tyr Glu Glu Gly Gly Leu Asn Leu Ala Leu Ala Ala
        275                 280                 285
```

```
Gln Leu Asp Leu Ser Glu Asn Gly Asp Lys Thr Lys Asn Ser Thr Thr
    290                 295                 300

Glu Ile Ala Ala Thr Ala Ser Tyr Arg Phe Gly Asn Ala Val Pro Arg
305                 310                 315                 320

Ile Ser Tyr Ala His Gly Phe Asp Phe Ile Glu Arg Gly Lys Lys Gly
                325                 330                 335

Glu Asn Thr Ser Tyr Asp Gln Ile Ile Ala Gly Val Asp Tyr Asp Phe
            340                 345                 350

Ser Lys Arg Thr Ser Ala Ile Val Ser Gly Ala Trp Leu Lys Arg Asn
        355                 360                 365

Thr Gly Ile Gly Asn Tyr Thr Gln Ile Asn Ala Ala Ser Val Gly Leu
370                 375                 380

Arg His Lys Phe
385

<210> SEQ ID NO 89
<211> LENGTH: 385
<212> TYPE: PRT
<213> ORGANISM: Nesseria meningitidis

<400> SEQUENCE: 89

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Asn Asn Ile Gln Leu Gln Leu Thr Glu Pro Leu Pro Asn Ile Gln
        35                  40                  45

Pro Gln Val Thr Lys Arg Lys Ser Arg Ile Arg Thr Lys Ile Ser Asp
    50                  55                  60

Phe Gly Ser Phe Ile Gly Phe Lys Gly Ser Glu Asp Leu Gly Glu Gly
65                  70                  75                  80

Leu Lys Ala Val Trp Gln Leu Glu Gln Asp Val Ser Val Ala Gly Gly
                85                  90                  95

Gly Ala Ser Gln Trp Gly Asn Arg Glu Ser Phe Ile Gly Leu Ala Gly
            100                 105                 110

Glu Phe Gly Thr Leu Arg Ala Gly Arg Val Ala Asn Gln Phe Asp Asp
        115                 120                 125

Ala Ser Gln Ala Ile Asp Pro Trp Asp Ser Asn Asn Asp Val Ala Ser
130                 135                 140

Gln Leu Gly Ile Phe Lys Arg His Asp Asp Met Pro Val Ser Val Arg
145                 150                 155                 160

Tyr Asp Ser Pro Glu Val Ser Gly Phe Ser Gly Ser Val Gln Phe Val
                165                 170                 175

Pro Ala Gln Asn Ser Lys Ser Ala Tyr Thr Pro Ala His Phe Val Gln
            180                 185                 190

Gln Thr Pro Gln Ser Gln Pro Thr Leu Val Pro Ala Val Val Gly Lys
        195                 200                 205

Pro Gly Ser Asp Val Tyr Tyr Ala Gly Leu Asn Tyr Lys Asn Gly Gly
    210                 215                 220

Phe Ala Gly Asn Tyr Ala Phe Lys Tyr Ala Lys His Ala Asn Val Gly
225                 230                 235                 240

Arg Asp Ala Phe Glu Leu Phe Leu Gly Ser Gly Ser Asp Glu Ala
                245                 250                 255

Lys Gly Thr Asp Pro Leu Lys Asn His Gln Val His Arg Leu Thr Gly
```

```
                260                 265                 270
Gly Tyr Glu Glu Gly Leu Asn Leu Ala Leu Ala Ala Gln Leu Asp
            275                 280                 285
Leu Ser Glu Asn Ala Asp Lys Thr Lys Asn Ser Thr Thr Glu Ile Ala
290                 295                 300
Ala Thr Ala Ser Tyr Arg Phe Gly Asn Ala Val Pro Arg Ile Ser Tyr
305                 310                 315                 320
Ala His Gly Phe Asp Phe Ile Glu Arg Gly Lys Lys Gly Glu Asn Thr
                325                 330                 335
Ser Tyr Asp Gln Ile Ile Ala Gly Val Asp Tyr Asp Phe Ser Lys Arg
            340                 345                 350
Thr Ser Ala Ile Val Ser Gly Ala Trp Leu Lys Arg Asn Thr Gly Ile
        355                 360                 365
Gly Asn Tyr Thr Gln Ile Asn Ala Ala Ser Val Gly Leu Arg His Lys
        370                 375                 380
Phe
385

<210> SEQ ID NO 90
<211> LENGTH: 387
<212> TYPE: PRT
<213> ORGANISM: Neisseria meningitidis

<400> SEQUENCE: 90

Met Arg Lys Lys Leu Thr Ala Leu Val Leu Ser Ala Leu Pro Leu Ala
1               5                   10                  15
Ala Val Ala Asp Val Ser Leu Tyr Gly Glu Ile Lys Ala Gly Val Glu
            20                  25                  30
Gly Arg Asn Phe Gln Leu Gln Leu Thr Glu Pro Pro Ser Lys Ser Gln
        35                  40                  45
Pro Gln Val Lys Val Thr Lys Ala Lys Ser Arg Ile Arg Thr Lys Ile
    50                  55                  60
Ser Asp Phe Gly Ser Phe Ile Gly Phe Lys Gly Ser Glu Asp Leu Gly
65                  70                  75                  80
Glu Gly Leu Lys Ala Val Trp Gln Leu Glu Gln Asp Val Ser Val Ala
                85                  90                  95
Gly Gly Gly Ala Thr Gln Trp Gly Asn Arg Glu Ser Phe Val Gly Leu
            100                 105                 110
Ala Gly Glu Phe Gly Thr Leu Arg Ala Gly Arg Val Ala Asn Gln Phe
        115                 120                 125
Asp Asp Ala Ser Gln Ala Ile Asp Pro Trp Asp Ser Asn Asn Asp Val
    130                 135                 140
Ala Ser Gln Leu Gly Ile Phe Lys Arg His Asp Asp Met Pro Val Ser
145                 150                 155                 160
Val Arg Tyr Asp Ser Pro Asp Phe Ser Gly Phe Ser Gly Ser Val Gln
                165                 170                 175
Phe Val Pro Ile Gln Asn Ser Lys Ser Ala Tyr Thr Pro Ala His Tyr
            180                 185                 190
Thr Arg Gln Asn Asn Ala Asp Val Phe Val Pro Ala Val Val Gly Lys
        195                 200                 205
Pro Gly Ser Asp Val Tyr Tyr Ala Gly Leu Asn Tyr Lys Asn Gly Gly
    210                 215                 220
Phe Ala Gly Ser Tyr Ala Phe Lys Tyr Ala Arg His Ala Asn Val Gly
225                 230                 235                 240
```

```
Arg Asp Ala Phe Glu Leu Phe Leu Leu Gly Ser Thr Ser Asp Glu Ala
                245                 250                 255
Lys Gly Thr Asp Pro Leu Lys Asn His Gln Val His Arg Leu Thr Gly
            260                 265                 270
Gly Tyr Glu Glu Gly Gly Leu Asn Leu Ala Leu Ala Ala Gln Leu Asp
        275                 280                 285
Leu Ser Glu Asn Gly Asp Lys Ala Lys Thr Lys Asn Ser Thr Thr Glu
    290                 295                 300
Ile Ala Ala Thr Ala Ser Tyr Arg Phe Gly Asn Ala Val Pro Arg Ile
305                 310                 315                 320
Ser Tyr Ala His Gly Phe Asp Leu Ile Glu Arg Gly Lys Lys Gly Glu
                325                 330                 335
Asn Thr Ser Tyr Asp Gln Ile Ile Ala Gly Val Asp Tyr Asp Phe Ser
            340                 345                 350
Lys Arg Thr Ser Ala Ile Val Ser Gly Ala Trp Leu Lys Arg Asn Thr
        355                 360                 365
Gly Ile Gly Asn Tyr Thr Gln Ile Asn Ala Ala Ser Val Gly Leu Arg
    370                 375                 380
His Lys Phe
385

<210> SEQ ID NO 91
<211> LENGTH: 8
<212> TYPE: PRT
<213> ORGANISM: Neisseria meningitidis

<400> SEQUENCE: 91

Glu Asn Gly Asp Lys Thr Lys Asn
1               5

<210> SEQ ID NO 92
<211> LENGTH: 24
<212> TYPE: DNA
<213> ORGANISM: Artificial sequence
<220> FEATURE:
<223> OTHER INFORMATION: PCR Primer

<400> SEQUENCE: 92
ggggtataat tgaagacgta tcgg                                          24

<210> SEQ ID NO 93
<211> LENGTH: 70
<212> TYPE: DNA
<213> ORGANISM: Artificial sequence
<220> FEATURE:
<223> OTHER INFORMATION: PCR Primer

<400> SEQUENCE: 93
taaatgcaaa gctaagcggc ttggaaagcc cggccggctt aaatttctta accaaaaaag   60
gaatacagca                                                          70
```

NEISSERIA PORIN PROTEINS

RELATED APPLICATIONS

The present application is a national stage application under 35 U.S.C. §371 of International Application Serial No. PCT/AU2011/000971, filed Aug. 1, 2011, which claims benefit of priority under 35 U.S.C. §119 to Australian Provisional Patent Application Serial No. AU 2010903418, filed on Jul. 30, 2010, the contents of each which are hereby incorporated by reference in their entirety.

TECHNICAL FIELD

THIS INVENTION relates to novel proteins that constitute modified forms of a *Neisseria meningitidis* PorA protein, to nucleic acids encoding such proteins, and to the use of these in therapeutic and prophylactic methods, compositions and particularly vaccines. More particularly, by disrupting non-conserved amino acids in surface loops of PorA, the invention provides proteins and encoding nucleic acids that may be useful in vaccines which effectively immunize against a broader spectrum of *N. meningitidis* strains than would be expected from a corresponding wild-type PorA protein.

BACKGROUND

*Neisseria meningitidis* is a Gram-negative bacterium and the causative agent of meningococcal meningitis and septicemia. Its only known host is the human, and it may be carried asymptomatically by approximately 10% of the population (Caugant et al, 1994, J. Clin. Microbiol. 32 323).

*N. meningitidis* may express a polysaccharide capsule, and this allows classification of the bacteria according to the nature of the capsule expressed. There are at least twelve serogroups of *N. meningitidis*: A, B, C, 29-E, H, I, K, L, W135, X, Y and Z, of which serogroups A, B, and C cause 90% of meningococcal disease (Poolman et al, 1995, Infect. Agents and Dis. 4 13). Vaccines directed against serogroups A and C are available, but the serogroup B capsular polysaccharide is poorly immunogenic and does not induce protection in humans.

Other membrane and extracellular components are therefore being examined for their suitability for inclusion in vaccines. Examples include the outer membrane proteins of classes 1, 2 and 3 (porin; encoded by por genes) and classes 4 (Rmp) and 5 (Opacity proteins; encoded by opa and opc genes). However, *N. meningitidis* is very effective at evading immune responses by antigenic and phase variation. For example, the Opc protein is an adhesin/invasin (Virji et al., 1995, Mol Microbiol. 18 741-54) that is highly immunogenic (Wiertz et al., 1996, Infect Immun. 64 298-304), yet its expression is phase-variable (Sarkari et al., 1994, Mol Microbiol. 13 207-17), and by diversion—generation of immune responses against hyperimmunogenic moving targets, in particular PorA.

PorA is highly variable between strains and generates an immune response in both patients and asymptomatic carriers, to the extent that it has been used as a marker for strain identification, representing the serosubtype system (McGuinness et al., 1990, J Exp Med. 171 1871-82). PorA is a key antigen, and has been used in previous effective and registered vaccine formulations and is considered an ideal antigen to elicit effective bactericidal antibodies. However, strain-to-strain variability in surface loops results in a variable target, and vaccines are typically PorA type-specific. Although efforts have been made to generate multivalent PorA vaccines covering up to six different PorA types (van der Voort et al., 1996, Infect Immun. 64 2745-51), this target has been judged to be too variable, and recent vaccine development has moved away from this antigen primarily for that reason.

The current model of PorA monomer topology indicates eight extracellular loops (Derrick et al., 1999, Infect. Immun. 67 2406-13; van der Ley et al., 1991, Infect. Immun. 59 2963). The longest loops (1 and 4) are the most variable, hence are referred to as Variable Region 1 (VR1) and Variable Region 2 (VR2). Less variability is seen in loops 5 and 6 (semi-variable SVR1 and 2 respectively), with essentially no variability in the remaining loops. Loop 3 is predicted to form a "plug" in the pore formed by each subunit of the PorA trimer. Even within VR1 and VR2, most of the variability is confined to residues predicted to form the tip of each loop. Indeed, in both mice and in immunized human volunteers, epitope mapping showed that the majority of the antibody response is directed at the "top" of loops 1 and 4, the region that is variable between strains (van der Voort, et al., 1997, FEMS Immunol. Med. Microbiol. 17 139-48), presumably explaining the strain specificity of anti-PorA responses.

SUMMARY

The present inventors have realized that the highly immunogenic surface loops of PorA are responsible for eliciting strain-specific immune responses that are not broadly protective, such that vaccines incorporating a PorA protein derived from a particular strain of *N. meningitidis* tend to preferentially immunize against that particular strain. As a result, the present inventors have sought to produce a PorA protein which elicits an immune response which is not as strain-specific as that elicited by wild-type PorA. By directing the immune response primarily against conserved epitopes, vaccines comprising the isolated protein should effectively immunize against a broader spectrum of *N. meningitidis* strains than would be expected following immunization with wild-type PorA.

In a first aspect, the invention provides an isolated protein comprising an amino acid sequence of a PorA protein of *Neisseria meningitidis*, wherein one or more amino acids of a variable region of said PorA protein are disrupted.

Suitably, the one or more amino acids of the variable region of said PorA protein are disrupted (e.g compared to a wild-type PorA protein) by comprising one or more PorA conserved regions, or conserved region amino acids. Preferably, the conserved regions are, or comprise, an amino acid sequence of a conserved loop 2, a conserved loop 3, a conserved loop 7 and/or a conserved loop 8.

Suitably, the variable region is selected from the group consisting of: a VR1; a VR2; an SVR1; and an SVR2 region.

Preferably, the variable region is selected from the group consisting of: a VR1; and a VR2 region.

The variable regions and the conserved regions may be of, derived from, or originate from, the same or different PorA protein.

Suitably, the isolated protein of the invention is capable of eliciting an immune response.

Preferably, the immune response is less strain-specific than that elicited by said corresponding wild-type PorA protein.

More preferably, said immune response provides protection against one or more strains of *N. meningitidis*, or even more preferably a plurality of strains of *N. meningitidis*.

Particular embodiments of isolated proteins of this aspect are provided in Specific examples of isolated proteins of this aspect are provided in FIGS. 1 and 2 (SEQ ID NOS:11-22).

Preferably, the isolated protein comprises an amino acid sequence set forth in any one of SEQ ID NOS:11-22.

Preferably, the disrupted variable region of the isolated protein does not consist of a deletion of a VR1 and/or a VR2 region, such as set forth in SEQ ID NOS:2-4.

The invention according to the first aspect includes homologs, fragments, variants and derivatives of the isolated proteins of the invention.

In one particular embodiment of this aspect, the isolated protein is present in an Outer Membrane Protein Vesicle (OMV).

In a second aspect, the invention provides an isolated nucleic acid encoding a polypeptide according to the first aspect.

Specific examples of isolated nucleic acids of this aspect are provided in FIG. 2 (SEQ ID NOS:23-43). Preferably, the isolated nucleic acid comprises a nucleotide sequence set forth in any one of SEQ ID NOS:32-43.

The invention according to the second aspect includes homologs, fragments, variants and derivatives of the isolated nucleic acids of the invention.

In a third aspect, the invention provides a genetic construct comprising an isolated nucleic acid according to the second aspect and one or more additional nucleotide sequences.

In a preferred form, the genetic construct is an expression construct comprising an expression vector and an isolated nucleic acid according to the second aspect, wherein said isolated nucleic acid is operably linked to one or more regulatory nucleic acids in said expression vector.

In a fourth aspect, the invention provides a host cell comprising a genetic construct according to the third aspect.

In one preferred embodiment, the host cell is a bacterium comprising a chromosomally-integrated expression construct.

Preferably, the bacterium is *Neisseria meningitidis*.

In a fifth aspect of the invention, there is provided a method of producing a recombinant isolated protein according to the first aspect, said method comprising the steps of:
 (i) culturing a host cell containing an expression vector according to the third aspect such that said polypeptide is expressed in said host cell; and
(ii) isolating said recombinant polypeptide.

In a sixth aspect, the invention provides an antibody or antibody fragment that binds to, or is raised against, an isolated protein of the invention, fragment, variant or derivative thereof.

In a seventh aspect, the invention provides a method of detecting *N. meningitidis* bacteria, said method including the steps of:—

(i) combining the antibody or antibody fragment of the sixth aspect with a biological sample obtained from a mammal; and
(ii) determining the presence or absence of a complex comprising said antibody or antibody fragment and *N. meningitidis* bacteria and/or *N. meningitidis* PorA protein in said sample, wherein the presence of said complex is indicative of said N meningitidis bacteria.

In an eighth aspect, the invention provides a method of detecting an antibody to *N. meningitidis* PorA protein, said method including the steps of:—

(i) contacting a biological sample obtained from a mammal with the isolated protein of the first aspect; and
(ii) determining the presence or absence of a complex comprising said isolated protein and *N. meningitidis* PorA antibodies in said sample.

In a ninth aspect, the invention provides a method of detecting a bactericidal antibody to *N. meningitidis*, said method including the steps of:—

(i) contacting a biological sample obtained from a mammal immunized with the isolated protein of the first aspect with *N. meningitidis* bacteria; and
(ii) determining the presence or absence of said bactericidal antibody in said sample.

In an tenth aspect, there is provided a method of detecting *N. meningitidis* bacteria, said method including the step of detecting a nucleic acid sequence according to the second aspect in a biological sample obtained from a mammal which indicates the presence of said bacteria.

Preferably, the mammal is a human.

In an eleventh aspect, the invention provides a kit for detecting an *N. meningitidis* infection, said kit comprising: an isolated protein according to the first aspect; an isolated nucleic acid according to the second aspect; and/or the antibody or antibody fragment of the sixth aspect; and optionally one or more other reagents.

In a twelfth aspect, the invention provides a pharmaceutical composition comprising: an isolated protein according to the first aspect; an isolated nucleic acid according to the second aspect; a genetic construct according to the third aspect; a host cell according to the fourth aspect; and/or an antibody or antibody fragment according the sixth aspect; and a pharmaceutically acceptable carrier, diluent or excipient.

In one embodiment, the pharmaceutical composition comprises a bacterium that comprises a chromosomally-integrated expression construct.

Preferably, the bacterium is *Neisseria meningitidis*.

In another embodiment, the pharmaceutical composition comprises the isolated protein in an Outer Membrane Protein Vesicle (OMV).

Suitably, the pharmaceutical composition is an immunogenic composition.

Preferably, the pharmaceutical composition is a vaccine.

In a thirteenth aspect, the invention provides a method of preventing or treating an *N. meningitidis* infection in a mammal, said method including the step of administering an isolated protein according to the first aspect; an isolated nucleic acid according to the second aspect; a genetic construct according to the third aspect; a host cell according to the fourth aspect; an antibody or antibody fragment according to the sixth aspect; and/or a pharmaceutical composition according to the twelfth aspect to the mammal to thereby prevent or treat said *N. meningitidis* infection in said mammal.

In one embodiment, the method administers a bacterium that comprises a chromosomally-integrated expression construct.

Preferably, the bacterium is *Neisseria meningitidis*.

In another embodiment, the method administers the isolated protein in an Outer Membrane Protein Vesicle (OMV).

Preferably, the mammal of the aforementioned aspects is a human.

Throughout this specification, unless the context requires otherwise, the words "comprise", "comprises" and "comprising" will be understood to mean the inclusion of a stated integer or group of integers but not the exclusion of any other integer or group of integers.

BRIEF DESCRIPTION OF THE FIGURES

FIG. 1: Line-up of amino acid sequence of wild-type PorA compared to embodiments of the isolated protein of the invention. Bold underline indicates van der Ley model loops (van der Ley et al., 1991, Infect. Immun. 59 2963). Italic indicates VR1 and VR2. - indicates insertion of spaces to achieve alignments. Wild type MC58 strain PorA amino acid sequence (SEQ ID NO:1); pPorDELL1 (SEQ ID NO:2); pPorDELL4 (SEQ ID NO:3); pPorDELL1-4 (SEQ ID NO:4); pPorDELL1-4-5 (SEQ ID NO:5); pDELVR1 (SEQ ID NO:6); pDELVR2 (SEQ ID NO:7); pDELVR1-2 (SEQ ID NO:8); pDELVR1-2-5 (SEQ ID NO:9); pDELVR1-2-5-6 (SEQ ID NO:10); pVR2-7 (SEQ ID NO:11); pVR2-8 (SEQ ID NO:12); pΔVR1VR2-7 (SEQ ID NO:13); pΔVR1VR2-8 (SEQ ID NO:14); pVR1-7VR2-8 (SEQ ID NO:15); pVR1-7VR2-8Δ5 (SEQ ID NO:16); pPOR7in1; (SEQ ID NO:17); pPor8in4 (SEQ ID NO:18) and pPOR7in1, 8in4 (SEQ ID NO:19).

FIG. 2: (A) Amino acid sequences of embodiments of the isolated proteins of the invention (SEQ ID NOS:2-18; see FIG. 1) and encoding nucleotide sequences as follows: pPorΔL1 (SEQ ID NO:23); pPorΔL4 (SEQ ID NO:24); pPorΔL1-4 (SEQ ID NO:25); pPorDEL1-4-5 (SEQ ID NO:26); pDELVR1 (SEQ ID NO:27); pDELVR2 (SEQ ID NO:28); pDELVR1-2 (SEQ ID NO:29); pDELVR1-2-5 (SEQ ID NO:30); pDELVR1-2-5-6 (SEQ ID NO:31); pVR2-7 (SEQ ID NO:32); pVR2-8 (SEQ ID NO:33); pΔVR1VR2-7 (SEQ ID NO:34); pΔVR1VR2-8 (SEQ ID NO:35); pVR1-7VR2-8 (SEQ ID NO:36); pVR1-7VR2-8Δ5 (SEQ ID NO:37); pPOR7in1; (SEQ ID NO:38); pPor8in4 (SEQ ID NO:39) and pPOR7in1, 8in4 (SEQ ID NO:40). Wild type MC58 strain porA nucleotide sequence is also provided (SEQ ID NO:44). (B) Amino acid sequences and encoding nucleic acids of further embodiments of the isolated proteins of the invention where VR1 and/or VR2 regions have been deleted and replaced with conserved loop 7 or loop 8 amino acids. AA seq pVR1-7VR2-7 (SEQ ID NO:20); VR18VR28 (SEQ ID NO:21) AA seq pVR1-8VR2-7 (SEQ ID NO:22); DNA seq pVR1-7VR2-7 (SEQ ID NO:41); DNA seq pVR1-8VR2-8 (SEQ ID NO:42); and DNA seq pVR1-8VR2-7 (SEQ ID NO:43).

Figure 3B:
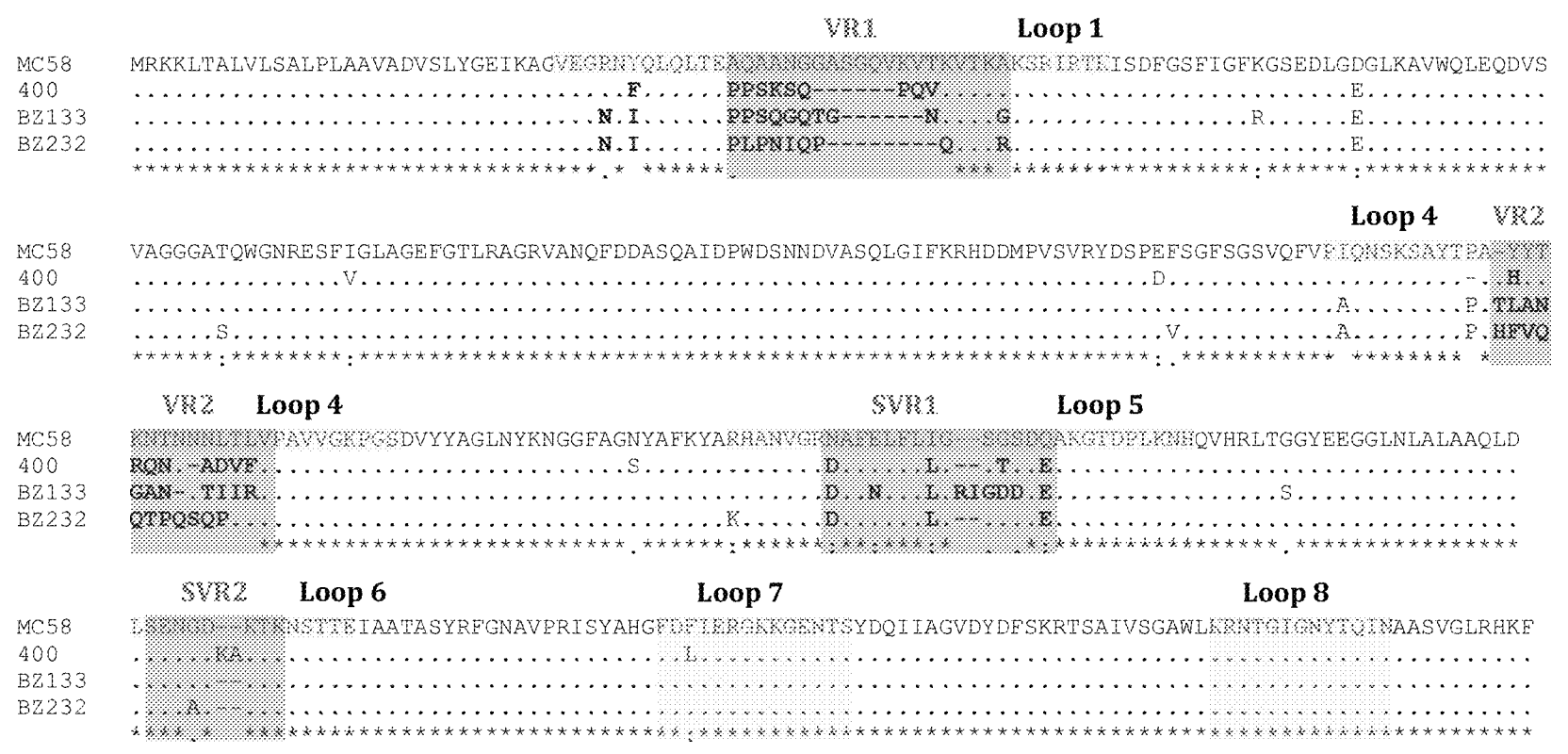

FIG. 3: (A) Lineup of partial amino acid sequence of MC58 and two other PorA wild-types with different sequence in one or more of VR1, VR2, SVR1 and SVR2 (SEQ ID NOS:85-87). Bold underline indicates van der Ley model (van der Ley et al., 1991, Infect. Immun. 59 2963) loops of MC58 PorA. Italic indicates VR1 and VR2 of MC58 PorA. - indicates insertion of spaces to achieve alignments. * under alignments indicate identical residues in all 3 sequences, where dots indicate conserved amino acids between sequences. (B) Alignment of PorA sequence from strains MC58, BZ133, BZ232, and 400 and consensus (SEQ ID NOS:1 and 88-90). Loops 1, 4, 5, 6, 7, and 8 are highlighted and are as described by the models of van der Ley et al 1991 supra, or Derrick et al 1999 supra. In the alignment, . indicates sequence identical to MC58 PorA, - indicates gap in sequence alignment. In the consensus, * indicates amino acids conserved in all of these sequences. : indicates conserved residues. . indicates semi-conserved residues.

FIG. 4: Western blotting detection of PorA protein constructs. Deoxycholate OMVs of *N. meningitidis* were separated on precast 8-12% Novex polyacrylamide gels and either stained with Coomassie blue (left panel), or Western blotted (right panel). PorA was detected using anti-PorA polyclonal antibody (Santa-Cruz Biotechnology Inc.). Lane 1: Molecular weight marker (apparent size indicated to left in kDa). Lane 2: ¢9 OMV, Lane 3: 9-Fix OMV, Lane 4: 9-1 OMV, Lane 5: 1728-2 OMV, Lane 6: 027-3, Lane 7: 028-10 OMV, Lane 8: 145-5 OMV. Strains are described in Table 5.

Figure 5:
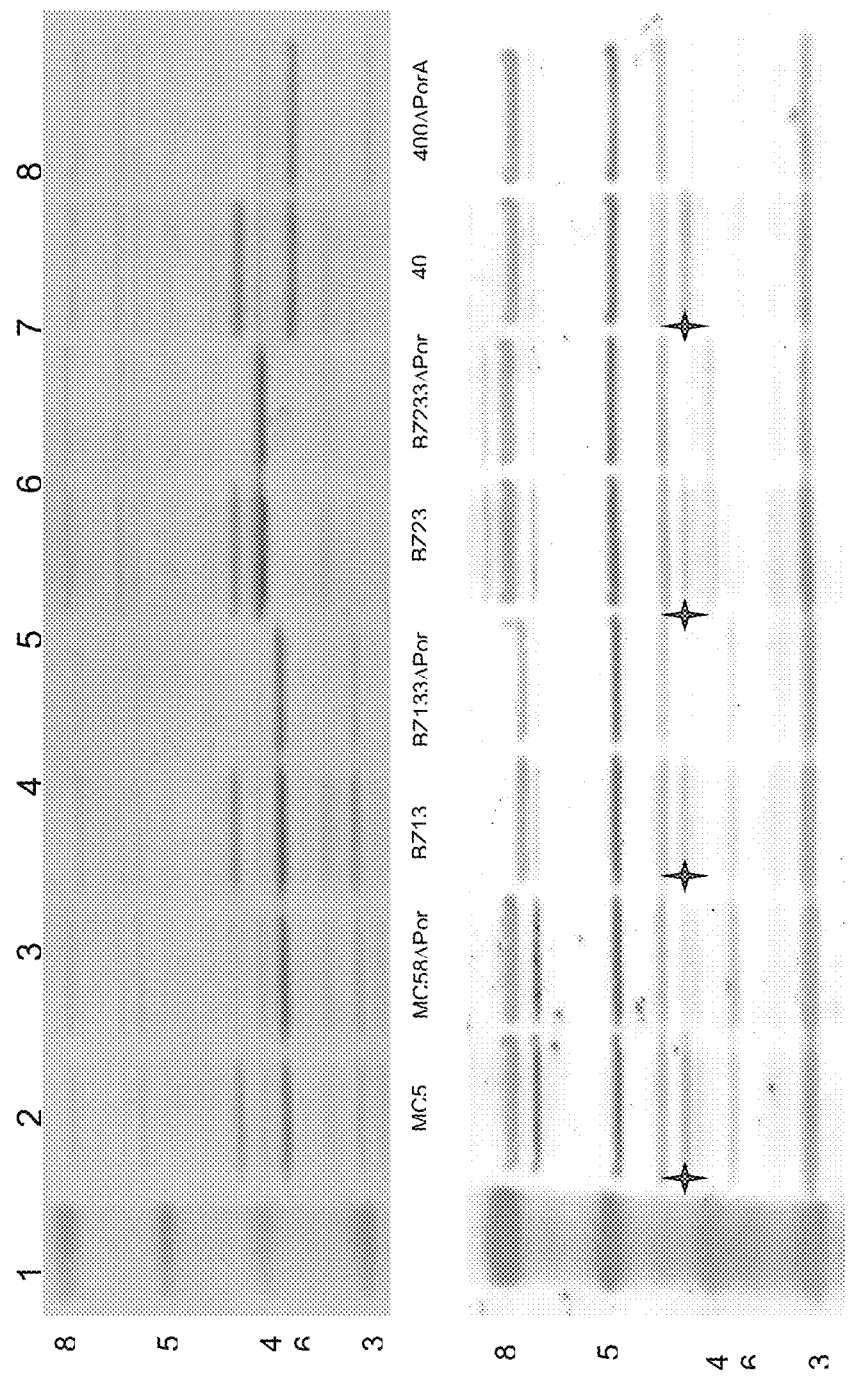

FIG. 5: Western blotting detection of porA protein constructs. Membrane proteins were prepared by sarkosyl extraction from four strains of differing PorA serosubtypes and their isogenic porA::tet mutants, and separated by electrophoresis prior to Commassie staining (top panel) or western immunoblotting (bottom panel). Proteins in the western blot were detected by pooled serum from 10 mice vaccinated with deoxycholate OMVs from strain 1728-2.

FIG. 6: ELISA analysis of sera from mice vaccinated with OMV from strains expressing recombinant PorA constructs: detection of cross-reactivity to surface epitopes of heterologous PorA. Reciprocal of Geometric mean titre data (from triplicate wells) is shown for Experiment 1 (A) and Experiment 2 (B).

DETAILED DESCRIPTION

It will be appreciated that central to the present invention is the realization that by disrupting surface loops comprising non-conserved amino acids in a wild-type PorA protein, an immune response may be elicited upon immunization which, by directing the immune response against conserved epitope sequences, will provide protection against a plurality of heterologous strains of *N. meningitidis*.

In one aspect, the invention provides an isolated protein comprising an amino acid sequence of a PorA protein of *Neisseria meningitidis*, wherein one or more variable regions of said PorA protein are disrupted so that the isolated PorA protein elicits an immune response against a plurality of strains of *Neisseria meningitidis*. Suitably, the one or more amino acids of the variable region of said PorA protein are disrupted (e.g compared to a wild-type PorA protein) by comprising one or more PorA conserved regions, or conserved region amino acids.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native or recombinant form.

By "protein" is meant an amino acid polymer. The amino acids may be natural or non-natural amino acids as are well understood in the art.

A "peptide" is a protein having no more than sixty (60) amino acids.

A polypeptide is a protein having more than sixty (60) amino acids.

By "disrupted" in this context is meant that while the isolated protein of the invention comprises an amino acid sequence of a PorA protein (including trans-membrane and/or intracellular amino acid sequences), one or more variable regions or variable region amino acids are at least partly, or are completely, absent and have been replaced by one or more conserved region amino acids and/or the one or more variable regions have one or more conserved region amino acids present or inserted in a variable region amino acid sequence.

Suitably, the variable region is selected from the group consisting of a VR1; a VR2; an SVR1; and an SVR2 region. Preferably, the disrupted variable region of the isolated protein does not consist of a deletion of a VR1 and/or VR2 region, such as set forth in SEQ ID NOS:2-4.

Table 1 provides a comparison of the amino acid sequences of variable regions described herein (i.e., VR1, VR2, SVR1, SVR2) and conserved regions as described herein with surface or extracellular loops 1-8 of PorA (such as exemplified by the amino acid sequence of a wild-type PorA protein of *N. meningitidis* strain MC58; SEQ ID NO:1). Reference is also made to FIGS. 3A and 3B, which demonstrate the diversity in variable region amino acid sequences between numerous strains and serotypes of *N. meningitidis*. The variability in VR1 and VR2 are more fully exemplified by reference to ≤http://pubmlst.org/neisseria/PorA/vr1.shtml≥ and ≤http://pubmlst.org/neisseria/PorA/vr2.shtml≥, and as described in Russell et al., 2004, Emerg Infect Dis. 10 674-8. It will therefore be appreciated that the present invention is applicable to PorA of any strain or serotype of *N. meningitidis*.

Specific examples of isolated proteins of the invention are provided in FIGS. 1 and 2 (SEQ ID NOS:5-22, or preferably SEQ ID NOS:11-22).

The most variable of the above variable regions are VR1 and VR2. SVR1 and SVR2 are semi-variable regions, SVR1 comprising more non-conserved amino acids than SVR2. Accordingly, preferably the disrupted variable region is a VR1 and/or a VR2 region. However, in particular embodiments SVR1 is disrupted, alone or in addition to one or more other variable regions such as VR1 and/or VR2.

As will be evident from FIG. 3 and Table 1 in particular, loops 1, 4, 5 and 6 generally correlate with variable regions as referred to herein. However, it will be appreciated that VR1 is a non-conserved or variable subsequence of loop 1 (e.g. AQAANGGASGQVKVTKVTKA; SEQ ID NO:45) and that VR2 is a non-conserved or variable subsequence of loop 4 (e.g. YYTKNTNNNLTLVP; SEQ ID NO:46) Accordingly, isolated proteins of the invention may have, in addition to disruptions of VR1 and/or VR2, a disruption of one or more amino acids of loops 1 and/or 4 that are not part of VR1 and VR2.

Similarly, isolated proteins of the invention may have, in addition to disruptions of SVR1 and/or SVR2, a disruption of one or more amino acids of loops 1 and/or 6 that are not part of SVR1 and/or SVR2.

SVR1 and SVR2 were originally defined in relation to the PorA gene of strain MC50 (accession no. X12899) at amino acids 247 to 261 (SVR1) and 299 to 302 (SVR2) in Claudio et al., 1998, Clin Diagn. Lab Immunol. 5 845-855. The van der Ley model referred to herein has loop 6 as comprising LSEN-GDKAKTKNSTTE (SEQ ID NO:52; see Table 1). Typically, although not exclusively, an SVR2 region may include the majority but not all loop 6 amino acids, such as ENGDKTKN (SEQ ID NO: 91) in light of the variation seen at some of these other residues in the line up shown in FIG. 3B.

As will be understood from the foregoing, in one broad embodiment, one or more entire PorA variable regions may be absent in an isolated protein of the invention, or one or a plurality of amino acids of one or more PorA variable regions may be absent, wherein one or a plurality of conserved PorA amino acids, such as loop 2, 3, 7 and/or 8 amino acids, or entire conserved loops (such as loop 2, 3, 7 and/or 8) effectively replace the absent variable region or variable region amino acids.

Particular embodiments comprise an amino acid sequence set forth in SEQ ID NOS:5-16 and 20-22. Preferred embodiments comprise an amino acid sequence set forth in SEQ ID NOS:11-16 and 20-22.

It will be appreciated that each VR1, VR2, SVR1 and/or SVR2 region can be independently manipulated to be deleted (e.g SEQ ID NOS:5-10), replaced with amino acids of conserved loops 7 or 8 (e.g. SEQ ID NOS: 11-16 and 20-22). Such manipulations can be combined so that a variable region may be deleted whilst another variable region is replaced with amino acids of conserved loop 7 or 8 (e.g SEQ ID NO: 13 & 14), or different variable regions can both be replaced by amino acid sequence of loops 7 or 8 (e.g. SEQ ID NOS 15, 16 and 20-22).

By way of example, a plurality of variable region amino acids may be two, three, four, five, six, seven, eight, nine, ten, eleven, twelve, thirteen, fourteen, fifteen, sixteen, seventeen, eighteen, nineteen, twenty or twenty-five or more amino acids of any variable region inclusive of VR1, VR2, SVR1 and SVR2. Suitably, the amino acids are contiguous. Specific examples are provided in Tables 2 and 3 and FIG. 1.

Also by way of example, a plurality of conserved amino acids of loop 2, 3, 7 or 8 may be two, three, four, five, six, seven, eight, nine, ten, eleven, twelve, thirteen, fourteen, fifteen, sixteen, seventeen, eighteen, nineteen or twenty or more amino acids of any one of these loops. Suitably, the amino acids are contiguous. Specific examples are provided in Tables 2 and 3 and FIG. 1.

Preferably, VR1 and VR2 are entirely absent, or one or a plurality of VR1 or VR2 amino acids are absent. In specific embodiments, loop 7 amino acids replace an entire VR1 region and/or loop 8 amino acids replace an entire VR2 region (SEQ ID NOS:11-16). In other embodiments, a VR1 region is absent and replaced by a conserved loop 8 or loop 7 amino acid sequence and/or a VR1 region is absent and replaced by a conserved loop 7 or loop 8 amino acid sequence (SEQ ID NOS:20-22).

In another broad embodiment, one or a plurality of conserved amino acids (such as loop 2, 3, 7 and/or 8 amino acids), or entire conserved loops (such as loop 2, 3, 7 and/or 8) are inserted into, or otherwise present in, PorA variable regions inclusive of VR1, VR2, SVR1 and SVR2. Suitably, the amino acids of the variable region or regions are present, wherein the conserved loop amino acids are present in, or inserted into, the variable region amino acid sequence.

Preferably, the conserved loop amino acids are present in, or inserted into, the VR1 and/or VR2 regions of PorA. Particular embodiments comprise an amino acid sequence set forth in SEQ ID NOS:17-19.

In an alternative embodiment, one or more variable regions of said PorA protein are disrupted (e.g compared to a wild-type PorA protein) without comprising one or more PorA conserved regions, or conserved region amino acids. Preferred examples of this alternative embodiment where one or more variable regions are absent without the insertion or presence of one or more PorA conserved regions, or conserved region amino acids are provided in SEQ ID NOS:5-10.

It will also be understood that while FIG. 1 (SEQ ID NO:1) and Table 1 refer to *N. meningitidis* strain MC58, the invention may be practiced in relation to any strain of *N. meningitidis*. More specifically, an isolated protein of the invention may comprise amino acid sequences of a plurality of different strains of *N. meningitidis*. By way of example only, conserved amino acids of PorA of the 2996 (Genbank accession number X60105.1) strain of *N. meningitidis* may be included in a PorA protein comprising an amino acid sequence that is essentially derived from, or corresponds to, PorA of M1336 strain of *N. meningitidis* (GenBank accession number AAF70297.1).

A summary of PorA protein constructs is provided in Table 7.

It will be appreciated that disruption of the one or more variable regions results in altered, modified or otherwise improved immunogenicity of conserved amino acid sequences of the isolated protein (relative to a wild-type or non-disrupted PorA protein). Suitably, the isolated protein of the invention elicits an immune response against a plurality of strains of *Neisseria meningitidis*.

As used herein, "elicits an immune response" refers to the ability of an isolated protein of the invention to produce an immune response in a mammal to which it is administered, wherein the response is directed to *N. meningitidis* and/or said protein. Preferably, the immune response includes production of bactericidal antibodies. More preferably, the immune response is protective against *N. meningitidis* infection.

Suitably, the elicited immune response is less strain specific, or more cross reactive, than that elicited by a wild-type PorA protein and/or a PorA protein without one or more disrupted variable regions.

"Strain-specific" is used herein in the context of an immune response which is directed to, or at least predominantly directed to, an autologous *N. meningitidis* strain.

As used herein, "cross-reactive" means an ability of an isolated protein of the invention to elicit an immune response directed to one or more heterologous *N. meningitidis* strains.

As used herein, "cross-protective" means an ability of an isolated protein of the invention to elicit an immune response and thereby provide protection against infection by one or more heterologous *N. meningitidis* strains.

The invention also provides fragments, homologs and derivatives of isolated proteins of the invention, such as comprising the amino acid sequences set forth in any one of SEQ ID NOS:2-22, or preferably SEQ ID NOS:11-22.

In one embodiment, a protein "fragment" includes an amino acid sequence that constitutes less than 100%, but at least 20%, 30%, 40%, 50%, 60%, 70%, 80% or 90-99% of said isolated protein.

In another embodiment, a "fragment" is a peptide, for example at least 6, preferably at least 10, 12, 15 and more preferably at least 20 or 30 amino acids in length.

In a preferred embodiment, the fragment comprises an amino acid sequence of a disrupted variable region as disclosed herein. Preferably, the fragment does not consist of a deletion of a VR1 and/or VR2 region, such as set forth in SEQ ID NOS:2-4.

Peptide fragments may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteases such as endoLys-C, endoArg-C, endoGlu-C and *staphylococcus* V8-protease. The digested fragments can be purified by, for example, high performance liquid chromatographic (HPLC) techniques.

It will also be appreciated that larger peptides and polypeptides comprising a plurality of the same or different fragments are contemplated.

Suitably, a fragment of the isolated protein of the invention comprises one or more antigenic determinants or epitopes. Preferably, the antigenic determinants or epitopes are capable of eliciting an immune response against a plurality of *N. meningitidis* strains.

Immunogenic fragments may be identified by administering the fragment to a mammal; and detecting an immune response in the mammal. Such response will include production of elements which specifically bind *N. meningitidis* and/or said isolated protein, variant or derivative, and/or a protective effect against *N. meningitidis* infection.

Optionally, prior to testing a particular fragment for immunogenicity in the above method, a variety of predictive methods may be used to deduce whether a particular fragment can be used to obtain an antibody that cross-reacts with the native antigen. These predictive methods may be based on amino-terminal or carboxy-terminal sequence as for example described in Chapter 11.14 of Ausubel et al., supra. Alternatively, these predictive methods may be based on predictions of hydrophilicity as for example described by Kyte & Doolittle 1982, J. Mol. Biol. 157 105 and Hopp & Woods, 1983, Mol. Immunol. 20 483) which are incorporated by reference herein, or predictions of secondary structure as for example described by Choo & Fasman, 1978, Ann. Rev. Biochem. 47 251), which is incorporated herein by reference.

In addition, "epitope mapping" uses antibodies of the invention to identify cross-reactive epitopes by first testing their ability to provide cross-protection, followed by identifying the epitope recognized by said antibodies. An exemplary method is provided in Coligan et al., CURRENT PROTOCOLS IN IMMUNOLOGY, supra.

As used herein, a protein "homolog" shares a definable nucleotide or amino acid sequence relationship with an isolated protein of the invention. Suitably, the homolog comprises one or more amino acids of a variable region (e.g VR1, VR2, SVR1 and/or SVR2) that are disrupted compared to a wild-type PorA protein.

Suitably, the homolog is not a wild-type PorA protein. Preferably, the variant does not consist of a deletion of a VR1 and/or VR2 region, such as set forth in SEQ ID NOS:2-4.

Preferably, protein homologs share at least 70% or 75%, preferably at least 80% or 85% or more preferably at least 90%, 91%, 92%, 93%, 94%, 95%, 96%, 97%, 98% or 99% sequence identity with the amino acid sequences of the invention, including but not limited to the amino acid sequences set forth in any one of SEQ ID NOS:5-22, or preferably SEQ ID NOS:11-22.

For example, such homologs are contemplated as having amino acid sequences that differ from those exemplified herein, but which are immunogenic and preferably provide cross-protective immunity.

The term "homolog" as used herein includes variant proteins. As used herein "variant" proteins of the invention have one or more amino acids deleted or substituted by different amino acids. It is well understood in the art that some amino acids may be substituted or deleted without changing the immunogenic activity of the polypeptide (conservative substitutions).

More substantial changes to immunogenicity may be made by introducing substitutions or deletions that are less conservative (non-conservative substitutions).

The term "variant" also includes isolated proteins of the invention produced from, or comprising amino acid sequences of, allelic variants.

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

Thus, it is well within the capabilities of the skilled person to prepare protein and nucleic acid homologs of the invention, such as variants as hereinbefore defined, by recombinant DNA technology. For example, nucleic acids of the invention can be mutated using either random mutagenesis for example using transposon mutagenesis, or site-directed mutagenesis. The resultant DNA fragments are then cloned into suitable expression hosts such as E. coli.

As used herein, "derivative" proteins have been altered, for example by conjugation or complexing with other chemical moieties, by post-translational modification (e.g phosphorylation, acetylation etc), modification of glycosylation (e.g. adding, removing or altering glycosylation) and/or inclusion of additional amino acid sequences as would be understood in the art.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g polyhistidine) fusion partners, maltose binding protein (MBP), Protein A, glutathione S-transferase (GST), fluorescent protein sequences (e.g. GFP), epitope tags such as myc, FLAG and haemagglutinin tags.

Other derivatives include isolated proteins having the polypeptide may be fused to an oligosaccharide based vaccine component where it acts as a carrier protein.

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Another aspect of the invention provides an isolated nucleic acid that encodes an isolated protein of the invention, inclusive of fragments variants and derivatives of the isolated protein.

The term "nucleic acid" as used herein designates single- or double-stranded DNU and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or SEQUENASE™.

Particular embodiments of isolated nucleic acids of the invention comprise a nucleotide sequence set forth in FIG. 2 (SEQ ID NOS:26-43).

Preferably, the isolated nucleic acid comprises a nucleotide sequence set forth in any one of SEQ ID NOS:32-43.

Another particular aspect of the invention provides a homolog of an isolated nucleic acid that encodes an isolated protein of the invention.

In one embodiment, nucleic acid homologs encode a homolog or variant of an isolated protein of the invention.

Suitably, nucleic acid homologs do not encode a wild-type PorA protein of N. meningitidis. Preferably, nucleic acid homologs comprise a nucleotide sequence that encodes one or more disrupted variable regions of PorA, as herein described.

In another embodiment, nucleic acid homologs share at least 60% or 65%, preferably at least 70% or 75%, more preferably at least 80% or 85%, and even more preferably at least 90% or 95% nucleotide sequence identity with an isolated nucleic acid of the invention, such as exemplified in FIG. 2 and/or SEQ ID NOS:26-43, or preferably SEQ ID NOS:32-43.

In yet another embodiment, nucleic acid homologs hybridize to isolated nucleic acids of the invention (such as those exemplified in FIG. 2 and/or SEQ ID NOS: NOS:26-43, or preferably SEQ ID NOS:32-43) under at least low stringency conditions, preferably under at least medium stringency conditions and more preferably under high stringency conditions.

"Hybridize and Hybridization" is used herein to denote the pairing of at least partly complementary nucleotide sequences to produce a DNA-DNA, RNA-RNA or DNA-RNA hybrid. Hybrid sequences comprising complementary nucleotide sequences occur through base-pairing between complementary purines and pyrimidines as are well known in the art.

In this regard, it will be appreciated that modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"High stringency conditions" designates those conditions under which only nucleic acid having a high frequency of complementary bases will hybridize.

Reference herein to high stringency conditions include and encompass:—
(i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
(ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1 mM EDTA, 40 mM NaHPO$_4$ (pH 7.2), 1% SDS for washing at a temperature in excess of 65° C. for about one hour; and
(iii) 0.2×SSC, 0.1% SDS for washing at or above 68° C. for about 20 minutes.

In general, washing is carried out at $T_m=69.3+0.41$ (G+C) %−12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of. Ausubel et al., supra. A skilled addressee will also recognize that various factors can be manipulated to optimize the specificity of the hybridization. Optimization of the stringency of the final washes can serve to ensure a high degree of hybridization.

Typically, complementary nucleotide sequences are identified by blotting techniques that include a step whereby nucleotides are immobilized on a matrix (preferably a synthetic membrane such as nitrocellulose), a hybridization step, and a detection step, typically using a labelled probe or other complementary nucleic acid. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al., supra, at pages 2.9.1 through 2.9.20. According to such methods, Southern blotting involves separating DNA molecules according to size by gel electrophoresis, transferring the size-separated DNA to a synthetic membrane, and hybridizing the membrane bound DNA to a complementary nucleotide sequence. An alternative blotting step is used when identifying complementary nucleic acids in a cDNA or genomic DNA library, such as through the process of plaque or colony hybridization. Other typical examples of this procedure is described in Chapters 8-12 of Sambrook et al., supra.

Methods for detecting labeled nucleic acids hybridized to an immobilized nucleic acid are well known to practitioners in the art. Such methods include autoradiography, chemiluminescent, fluorescent and colorimetric detection.

Nucleic acids may also be isolated, detected and/or subjected to recombinant DNA technology using nucleic acid sequence amplification techniques.

Suitable nucleic acid amplification techniques are well known to the skilled addressee, and include polymerase chain reaction (PCR); strand displacement amplification (SDA); rolling circle replication (RCR); nucleic acid sequence-based amplification (NASBA), Q-β replicase amplification and helicase-dependent amplification, although without limitation thereto.

As used herein, an "amplification product" refers to a nucleic acid product generated by nucleic acid amplification.

Nucleic acid amplification techniques may include particular quantitative and semi-quantitative techniques such as qPCR, real-time PCR and competitive PCR, as are well known in the art.

Yet another aspect of the invention provides a genetic construct that comprises an isolated nucleic acid of the invention and one or more additional nucleotide sequences.

Suitably, the genetic construct is in the form of, or comprises genetic components, of, a plasmid, bacteriophage, a cosmid, a yeast or bacterial artificial chromosome as are well understood in the art.

Genetic constructs may be suitable for maintenance and propagation of the isolated nucleic acid in bacteria or other host cells, for manipulation by recombinant DNA technology and/or expression of the nucleic acid or an encoded protein of the invention.

For the purposes of host cell expression, the genetic construct is an expression construct. Suitably, the expression construct comprises the nucleic acid of the invention operably linked to one or more additional sequences in an expression vector. Non-limiting examples of expression constructs are provided in Table 2 and Table 3.

An "expression vector" may be either a self-replicating extra-chromosomal vector such as a plasmid, or a vector that integrates into a host genome.

By "operably linked" is meant that said additional nucleotide sequence(s) is/are positioned relative to the nucleic acid of the invention preferably to initiate, regulate or otherwise control transcription.

In one embodiment, the additional nucleotide sequences are regulatory sequences. Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter.

In another embodiment, the additional nucleotide sequence is a selectable marker gene to allow the selection of transformed host cells. Selectable marker genes are well known in the art and will vary with the host cell used.

One particular embodiment of an additional nucleotide sequence comprises a modified poly-G sequence. Wild-type porA gene has a poly-G tract in its promoter that is variable within and between strains, and causes variable expression levels. To ensure consistent expression of isolated proteins of the invention, the poly-G tract can be modified to reduce variation, as $G_{11}$ is associated with optimal expression of PorA. To reduce changes in the poly-G tract, it may be modified such that it is replaced with $G_5AG_5$.

The expression construct may also include an additional nucleotide sequence encoding a fusion partner (typically provided by the expression vector) so that the recombinant polypeptide of the invention is expressed as a fusion protein, as hereinbefore described.

The expression construct may also include one or more additional nucleotide sequences that facilitate homologous recombination of the isolated nucleic acid present in the expression construct into the bacterial genome. By way of example only, the endogenous porA gene of N. meningitidis may be replaced with an exogenous nucleotide sequence (e.g. the LacZ-Kan$^r$ cassette from pLK6; Szabo et al., 1992, J. Bacteriol 174 7245-7252) or the sacB-Kan$^r$-Tet$^r$ cassette from pJJ260 (Neil et al., 2009, Infect Immun. 77 2285-2293.) that enables selection of transformants and homologous recombination with an expression construct comprising an isolated nucleic acid of the invention and an additional nucleotide sequence (e.g. LacZ-Kan$^r$ cassette from pLK6 or the sacB-Kan$^r$-Tet$^r$ cassette from pJJ260). Other homologous recombination approaches are well known to those of skill in the art.

For the particular purpose of fusion polypeptide purification by affinity chromatography, relevant matrices for affinity chromatography are glutathione-, amylose-, and nickel- or cobalt-conjugated resins respectively. Many such matrices are available in "kit" form, such as the QIAEXPRESST™ system (Qiagen) useful with (HIS$_6$) fusion partners and the Pharmacia GST purification system.

Preferably, the fusion partners also have protease cleavage sites, such as for Factor X$_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Isolated proteins of the invention (inclusive of fragments, derivatives and homologs) may be prepared by any suitable procedure known to those of skill in the art. Preferably, the isolated protein is a recombinant protein.

By way of example only, a recombinant isolated protein of the invention may be produced by a method including the steps of:
 (i) preparing an expression construct which comprises an isolated nucleic acid of the invention, operably linked to one or more regulatory nucleotide sequences;
 (ii) transfecting or transforming a suitable host cell with the expression construct;
 (iii) expressing a recombinant protein in said host cell; and
 (iv) isolating the recombinant protein from said host cell.

Suitable host cells for expression may be prokaryotic or eukaryotic. For example, suitable host cells may be mammalian cells, plant cells, yeast cells; insect cells or bacterial cells. One preferred host cell for expression of an isolated protein according to the invention is a bacterium. The bacterium used may be Escherichia coli or N. meningitidis.

In a preferred embodiment, the host cell is N. meningitidis. Preferably, the N. meningitidis host cell has been modified so as to not express endogenous PorA, Opa, Opc or capsular polysaccharide and expresses a desired lipopolysaccharide phenotype.

Introduction of genetic constructs into host cells (whether prokaryotic or eukaryotic) is well known in the art, as for example described in CURRENT PROTOCOLS IN MOLECULAR BIOLOGY Eds. Ausubel et al., (John Wiley & Sons, Inc. 1995-2009), in particular Chapters 9 and 16. In relation to transformation of N. meningitidis, such methods are well known in the art. It will also be appreciated that N. meningitidis is "naturally" transformable.

The recombinant protein may be conveniently prepared by a person skilled in the art using standard protocols as for example described in Sambrook, et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-2009), in particular Chapters 10 and 16; and CURRENT PROTOCOLS IN PROTEIN SCIENCE Eds. Coligan et al, (John Wiley & Sons, Inc. 1995-2009), in particular Chapters 1, 5 and 6.

Also provided are antibodies and/or antibody fragments raised against and which bind the isolated proteins, fragments, homologs and derivatives disclosed herein. Suitably, the antibodies and/or antibody fragments do not bind a wild-type PorA protein. Preferably, the antibodies and/or antibody fragments specifically bind a disrupted PorA variable region (e.g. VR1, VR2, SVR1 or SVR2 region) and do not bind a wild-type PorA variable region (e.g. VR1, VR2, SVR1 or SVR2 region).

Antibodies may be polyclonal or monoclonal, native or recombinant. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988, which are both herein incorporated by reference.

Generally, antibodies of the invention bind to or conjugate with an isolated protein, fragment, homolog or derivative of the invention. For example, the antibodies may be polyclonal antibodies. Such antibodies may be prepared for example by injecting an isolated protein, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

Monoclonal antibodies may be produced using the standard method as for example, described in an article by Miller & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the isolated proteins, fragments, variants or derivatives of the invention.

The invention also includes within its scope antibody fragments, such as Fc, Fab or F(ab)2 fragments of the polyclonal or monoclonal antibodies referred to above. Alternatively, the antibodies or antibody fragments may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter & Milstein, 1991, Nature 349 293.

Antibodies and antibody fragments may be used for passive immunization against *N. meningitidis* infection. Preferably, such antibodies are bactericidal.

Antibodies and antibody fragments may be used for epitope mapping, as hereinbefore described.

Antibodies and antibody fragments of the invention may be used for affinity chromatography. For example reference may be made to immunoaffinity chromatographic procedures described in Chapter 9.5 of Coligan et al., CURRENT PROTOCOLS IN IMMUNOLOGY, supra.

Antibodies and antibody fragments may be used for detection of *N. meningitidis* bacteria and/or *N. meninigitidis* PorA protein.

In an aspect, a method of detecting *N. meningitidis* bacteria in a mammal includes the steps of:—
(i) combining the antibody or antibody fragment of the invention with a biological sample obtained from a mammal; and
(ii) determining the presence or absence of a complex comprising said antibody or antibody fragment and *N. meninigitidis* bacteria and/or *N. meningitidis* PorA protein in said sample, wherein the presence of said complex is indicative of said *N. meningitidis* bacteria.

The presence or absence of *N. meningitidis* bacteria in the biological sample may be determined by obtaining the biological sample from a mammal, mixing an antibody or antibody fragment described above with the biological sample, and detecting specifically-bound antibody or antibody fragment which indicates the presence of *N. meningitidis* bacteria in the sample. Typically, the specifically-bound antibody or antibody fragment forms a complex with *N. meningitidis* PorA protein in the biological sample.

Suitably, the *N. meningitidis* PorA protein is derived from or originates from *N. meningitidis* bacteria that infect said mammal.

The term "biological sample" as used herein refers to a sample that may be extracted, untreated, treated, diluted or concentrated from an individual; such as a patient. Suitably, the biological sample is selected from the group consisting of whole blood, serum, plasma, saliva, urine, sweat, ascitic fluid, peritoneal fluid, synovial fluid, amniotic fluid, cerebrospinal fluid, skin biopsy, and the like.

In another aspect a method of detecting an antibody to *N. meningitidis* PorA protein in a biological sample includes the steps of
(i) contacting a biological sample obtained from a mammal with the isolated protein of the invention (such as according to SEQ ID NOS:2-22 or preferably SEQ ID NOS:11-22); and
(ii) determining the presence or absence of a complex comprising said isolated protein and anti-*N. meningitidis* PorA antibodies in said sample.

Suitably, the anti-*N. meningitidis* PorA antibodies are endogenous antibodies elicited in response to infection of the mammal by *N. meningitidis* bacteria.

Any suitable technique for protein detection may be used including immunoassays, protein arrays (inclusive of protein in situ arrays, DNA to protein arrays and nucleic acid programmable arrays and two-dimensional (2D) expression profiling), although without limitation thereto. Immunoassays may include, but are not limited to immunoblotting, Western blotting and dot blotting, radioimmunoassays (RIAs), enzyme-linked immunosorbent assays (ELISAs) and immunochromatographic techniques (ICTs) which are well known those of skill in the art. For example, reference may be made to Chapter 7 of Coligan et al., CURRENT PROTOCOLS IN IMMUNOLOGY, supra which discloses a variety of immunoassays that may be used in accordance with the present invention. Immunoassays may include competitive assays as understood in the art.

In a preferred embodiment, detection is effected by modifying said isolated protein, fragment, homolog or derivative, or said antibody or antibody fragment with a label. One embodiment uses the labelled protein, fragment, homolog or derivative in an immunoassay to detect the *N. meningitidis*-specific antibodies. Another embodiment uses the labeled antibody or antibody fragment in an immunoassay to detect the PorA protein.

In regard to antibodies and antibody fragments, the label may include the following:
(A) direct attachment of the label to the antibody or antibody fragment;
(B) indirect attachment of the label to the antibody or antibody fragment; i.e., attachment of the label to another reagent (such as a secondary antibody)which subsequently binds to the antibody or antibody fragment; and
(C) attachment to a subsequent reaction product of the antibody or antibody fragment.

The label may be selected from a group including a chromogen, a catalyst, an enzyme, a fluorophore, a chemiluminescent molecule, a lanthanide ion such as Europium ($Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

Non-limiting examples of enzyme labels useful in the present invention include alkaline phosphatase, horseradish peroxidase, luciferase, β-galactosidase, glucose oxidase, lysozyme, malate dehydrogenase and the like. The enzyme label may be used alone or in combination with a second enzyme in solution.

Non-limiting examples of fluorophores include fluorescein isothiocyanate (FITC), allophycocyanin (APC), fluoroscein derivatives such as FAM and ROX, Texas Red, tetramethylrhodamine isothiocyanate (TRITL), R-Phycoerythrin (RPE), Alexa and Bodipy fluorophores, although without limitation thereto.

Also provided is a method of detection of anti-*N. meningitidis* antibodies (e.g bactericidal antibodies) in a biological sample.

In an aspect, there is provided a method of detecting a bactericidal antibody to *N. meningitidis* including the steps of:—
(i) contacting a biological sample obtained from a mammal immunized with the isolated protein of the invention (such as according to SEQ ID NOS:2-22 or preferably SEQ ID NOS:11-22) with *N. meningitidis* bacteria; and
(ii) determining the presence or absence of said bactericidal antibody in said sample.

Typically, the bactericidal antibody is elicited in response to immunization with the isolated protein. An example of a bactericidal assay that detects bactericidal antibodies is provided hereinafter in the Examples.

In another broad aspect, the invention provides nucleic acid-based detection methods.

In one embodiment, a method of detecting *N. meningitidis* bacteria in a biological sample includes the steps of isolating the biological sample from a patient and using an isolated nucleic acid of the invention to detect detecting a nucleic acid sequence encoding a PorA protein in the sample. Detection of the nucleic acid may be performed using any suitable technique. For example, a labeled nucleic acid according to the invention may be used as a probe in a Southern blot of a nucleic acid extract obtained from a patient as is well known in the art.

Alternatively, a labeled nucleic acid according to the invention may be utilized as a probe in a Northern blot of an RNA or cDNA extract from the patient. Preferably, a nucleic acid extract from the patient is utilized in concert with oligonucleotide primers corresponding to sense and antisense sequences of a nucleic acid sequence of the invention, with a nucleic acid amplification technique such as PCR, to thereby produce an amplification product. The amplification product may be detected by any of the number of techniques, such as by probe hybridization as hereinbefore described.

A variety of automated solid-phase detection techniques are also appropriate for detecting nucleic acids. These include very large scale immobilized primer arrays (VLSIPS™), magnetic bead-based capture of PCR amplification products and nucleic acid arrays, as are well understood in the art.

The present invention also provides kits for the detection of an N. meningitidis infection. The kit may comprise one or more detection agents for detecting N. meningitidis bacteria, endogenous N. meningitidis PorA protein or encoding nucleic acid, or antibodies in a biological sample. The kit will contain one or more particular detection agents described above depending upon the nature of the test method employed. In this regard, the kits may include one or more of an isolated protein, fragment, homolog, derivative, antibody, antibody fragment or nucleic acid (e.g. primers or probes) according to the invention. Any one or more of these may be labelled, as hereinbefore described. The kits may also optionally include one or more other reagents such as detection reagents such as labeled secondary antibodies, enzymes and/or substrates for colorimetric or bioluminescent detection, positive and/or negative controls, washing solutions, dilution buffers, protein or nucleic acid size markers, DNA polymerase, DNA ligase, Taq polymerase etc. depending on the detection method employed.

Further aspects of the invention provide prophylactic and therapeutic methods and/or pharmaceutical compositions for treating an N. meningitidis infection in a mammal.

In one particular aspect, a method of preventing or treating an N. meningitidis infection in a mammal includes the step of administering to the mammal an immunogenic agent selected from the group consisting of:

(i) an isolated protein of the invention (such as according to SEQ ID NOS:2-22 or preferably SEQ ID NOS:11-22, inclusive of homologs, derivatives and fragments thereof;

(ii) an isolated nucleic acid of the invention (such as according to SEQ ID NOS:23-43 or preferably SEQ ID NOS: 32-43), inclusive of homologs, derivatives and fragments thereof;

(iii) an expression construct encoding the isolated nucleic acid of (ii);

(iv) a host cell comprising the expression construct of (iii);

(v) an antibody or antibody fragment which binds an isolated protein of the invention; and/or (vi) a pharmaceutical composition comprising one or more of (i)-(v) to thereby prevent or treat said N. meningitidis infection in said mammal.

Suitably, the immunogenic agent elicits an immune response in said mammal that is less strain specific, or more cross reactive, than that elicited by a wild-type PorA protein and/or a PorA protein without one or more disrupted variable regions. Preferably, the elicited immune response is a protective immune response.

Preferably, the mammal is a human.

In one particular preferred embodiment, the isolated protein of the invention, inclusive of homologs, derivatives and fragments thereof, is present in an OMV.

There are many well known methods for preparation of OMV vaccines, for example as described in Frasch, C., L. van Alphen, et al. (2001). Outer Membrane. Protein Vesicle Vaccines for Meningococcal Disease. *Meningococcal Vaccines: Methods and Protocols*. A. Pollard and M. Maiden, eds, Humana Press. 66: 81-107.

In another particular preferred embodiment, the isolated protein of the invention, inclusive of homologs, derivatives and fragments thereof, is expressed by a bacterium comprising a chromosomally-integrated expression construct. Preferably, the bacterium is N. meningitidis.

Suitably, the pharmaceutical composition comprises a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for administering the immunogenic agents of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is immunogenically-effective to protect patients from N. meningitidis infection, or treat an existing infection. The dose administered to a patient, in the context of the present invention, should be sufficient to effect a beneficial response in a patient over time such as a reduction in the level of *N. meningitidis*, or to inhibit infection by *N. meningitidis*. The quantity of the immunogenic agent(s) to be administered may depend on the subject to be treated inclusive of the age, sex, weight and general health condition thereof. In this regard, precise amounts of the immunogenic agent(s) required to be administered will depend on the judgement of the practitioner.

In determining the effective amount of the immunogenic agent to be administered in the treatment or prophylaxis against *N. meningitidis*, the physician may evaluate circulating plasma levels, progression of disease, and the production of anti-*N. meningitidis* antibodies. In any event, suitable dosages of the immunogenic agents of the invention may be readily determined by those of skill in the art. Such dosages may be in the order of nanograms to milligrams of the immunogenic agents of the invention.

In particular embodiments, the immunogenic agents of the invention may be administered at a therapeutic or prophylactic vaccine. Accordingly, the invention extends to the production of vaccines containing as actives one or more of the immunogenic agents of the invention. A variety of applicable procedures are contemplated for producing such vaccines. Exemplary procedures include, for example, those described in NEW GENERATION VACCINES (1997, Levine et al., Marcel Dekker, Inc. New York, Basel Hong Kong) which is incorporated herein by reference.

An immunogenic agent according to the invention can be mixed, conjugated or fused with other antigens, including B or T cell epitopes of other antigens. In addition, it can be conjugated to a carrier as described below.

When a haptenic peptide of the invention is used (i.e., a peptide which reacts with cognate antibodies, but cannot itself elicit an immune response), it can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a haptenic peptide of the invention can be coupled to a T cell epitope of a bacterial toxin, toxoid or CRM. In this regard, reference may be made to U.S. Pat. No. 5,785,973.

The immunogenic agents of the invention may be administered as multivalent subunit vaccines in combination with antigens of *N. meningitidis*, or antigens of other organisms inclusive of the pathogenic bacteria *H. influenzae, M. catarrhalis, N. gonorrhoeae, E. coli, S. pneumoniae* etc. Alternatively or additionally, they may be administered in concert with oligosaccharide or polysaccharide components of *N. meningitidis*.

Vaccines and other immunogenic compositions may include an adjuvant as is well known in the art. Adjuvants contemplated by the present invention include, but are not limited to: surface active substances such as hexadecylamine, octadecylamine, octadecyl amino acid esters, lysolecithin, dimethyldioctadecylammonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS). In embodiments relating to OMV delivery, these vesicles may be produced with or without adjuvants, such as Aluminium salts With regard to examples of adjuvants, reference is also made to International Publication WO99/36544 incorporated herein by reference.

In particular embodiments, compositions and methods for treating *N. meningitidis* infections, inclusive of vaccines and methods of immunization, may include DNA expression constructs encoding isolated proteins of the invention.

For example, the immunogenic agents of the invention may be expressed by attenuated viral hosts. By "attenuated viral hosts" is meant viral vectors that are either naturally, or have been rendered, substantially avirulent. A virus may be rendered substantially avirulent by any suitable physical (e.g., heat treatment) or chemical means (e.g., formaldehyde treatment). By "substantially avirulent" is meant a virus whose infectivity has been destroyed. Ideally, the infectivity of the virus is destroyed without affecting the proteins that carry the immunogenicity of the virus. From the foregoing, it will be appreciated that attenuated viral hosts may comprise live viruses or inactivated viruses.

Attenuated viral hosts which may be useful in a vaccine according to the invention may comprise viral vectors inclusive of adenovirus, cytomegalovirus and preferably pox viruses such as vaccinia (e.g. U.S. Pat. No. 4,603,112) and attenuated *Salmonella* strains (e.g. as described in U.S. Pat. No. 4,550,081). Live vaccines are particularly advantageous because they lead to a prolonged stimulus that can confer substantially long-lasting immunity. Another reference which describes a variety of viral vectors potentially suitable for immunization using *Neisseria* proteins, and methods of delivery, is International Publication WO99/36544 incorporated herein by reference.

Multivalent vaccines can be prepared from one or more microorganisms that express different epitopes of *N. meningitidis* (e.g., other surface proteins or epitopes of *N. meningitidis*). In addition, epitopes of other pathogenic microorganisms can be incorporated into the vaccine. For example, this may involve the construction of a recombinant vaccinia virus to express a nucleic acid sequence according to the invention. Upon introduction into a host, the recombinant vaccinia virus expresses the immunogenic agent, and thereby elicits a host CTL response. For example, reference may be made to U.S. Pat. No. 4,722,848, incorporated herein by reference, which describes vaccinia vectors and methods useful in immunization protocols.

A wide variety of other vectors useful for therapeutic administration or immunization with the immunogenic agents of the invention will be apparent to those skilled in the art from the present disclosure.

In order that the invention may be readily understood and put into practical effect, particular preferred embodiments will now be described by way of the following non-limiting examples.

EXAMPLES

Introduction

PorA is a major protein of *Neisseria meningitidis*. PorA is highly variable between strains and generates an immune response in both patients and asymptomatic carriers, to the extent that it has been used as a marker for strain identification, representing the serosubtype system (McGuinness et at 1990, supra). The current model of PorA monomer topology indicates eight extracellular loops. (Derrick et at 1999, supra; van der Ley et at 1991, supra). As summarized in Table 1, the longest loops (1 and 4) are the most variable, less variability is seen in loops 5 and 6 (semi-variable SVR1 and 2 respectively), with essentially no variability in the remaining loops. Loop 3 mis predicted to form a "plug" in the pore formed by each subunit of the PorA trimer. Even within loops 1 and 4, the majority of the variation between strains is confined those residues predicted to form the tip of the loops. These are known as Variable region (VR) 1 and 2. The VR1 and VR2 sequences of many strains have been identified (see for example FIG. 3 and Tables 3 and 4; Russell et al., 2004, Emerg. Infect. Dis. 10 674; ≤http://neisseria.org/nm/typing/pora/vr1.shtml≥ and ≤http://neisseria.org/nm/typing/pora/vr2.shtml≥). Surprisingly there is much scientific literature that describes how regions outside of VR1/VR2 also contribute to immune responses against *N. meningitidis* (Jordans et al., 2004, Infect. Immun. 72 6503-10; van der Voort et al., 1996, supra; Martin et al., 2000, Vaccine 18 2476-81; Wedege et al., 2003, Infect. Immun. 71 3775-81; Kotelnikova et al., 2005, Bull. Exp. Biol. 139 593-5; U.S. Pat. No. 7,238,345).

The invention provides two broad embodiments exemplified herein: (1) deletion of variable regions to focus immune responses to regions of PorA that are conserved between *Neisseria meningitidis* strains; and (2) novel presentation of conserved regions enhances immune responses to conserved regions of *Neisseria meningitidis*

Example 1

Generation of PorA Alleles with Variable Loops or Regions Deleted, and PorA Alleles with Selectable Markers The porA gene and flanking sequence was amplified by PCR from genomic DNA of *Neisseria meningitidis* strain MC58 and cloned into pGEMTeasy to generate pPorA. This plasmid was used as template for various inverse PCR reactions, or for restriction digest-mediated recombinatorial construction. Plasmids were sequenced. Plasmids made in this fashion had one or more deletions and/or disruptions as listed in Table 2 and Table 3. Additional plasmids were constructed by standard molecular biology methods (restriction digest, ligation, cloning) to generate plasmids with the porA gene replaced by selectable markers (see Table 2). It will be apparent that number of amino acids deleted can be larger or smaller than those described.

Example 2

Plasmids with Conserved Regions Replacing Variable Regions

Plasmids pDELVR1-2, and pPorA were used as templates to generate by PCR and other standard molecular biology techniques several PorA alleles in which the VR1 and VR2 encoding regions of porA were replaced or modified with sequence of loops 7 and 8 as described in Table 3 and FIG. 1. It should be apparent that DNA sequence encoding other conserved amino acids sequence of PorA e.g. sequence defined as "loop 2", VSVGGGATQWGNR (SEQ ID NO:48) or any other conserved PorA peptide sequences, could be incorporated into loops 1 and/or 4 for enhanced presentation to the human or animal immune systems.

A lineup of the described MC58 and recombinant PorA sequences is presented .in FIG. 1.

Example 3

Replacement of Wild-Type PorA with Gene Expressing Recombinant PorA

The plasmids with PorA nucleotide sequences described in Table 2, Table 3 and FIG. 1 and FIG. 2 can be transformed into *Neisseria meningitidis* by natural transformation and homologous recombination results in replacement of the wild-type porA with recombinant sequence. Alternately, the recombinant porA alleles can be amplified from plasmids encompassing said recombinant porA alleles and these amplimers can be used to transform *N. meningitidis*. To facilitate identification of transformants, recipient *Neisseria meningitidis* strains were prepared in which the porA gene was deleted and replaced with either the LacZ-Kan$^r$ cassette from pLK6 genes, or with the sacB-Kan$^r$-Tet$^r$ cassette from pJJ260 (see Table 2). Strain ¢3 was the recipient strain (Virji et al., 1995, supra). Strain ¢9 (Virji et al., 1995, supra) was also transformed with pPorDel:LacZkan and blue colonies selected after growth on media containing X-gal. Subsequently chromosomal DNA of ¢2:delPorASacb was transformed into ¢9:delPorALacZ with selection on X-Gal, and white colonies selected to generate ¢9delPorASacb. This latter strain was used as a recipient for transformation with plasmid containing variant porA alleles. Growth on media containing 10% sucrose allowed selection for clones that had replaced the porA:sacB allele with the variant PorA gene. In this way, strains of *N. meningitidis* have been generated that express PorA with loops 1, 4, and 5 deleted, or with VR1 and VR2 replaced or modified with loops 7 and 8 respectively. It will be apparent that a recombinant porA gene can be transcriptionally linked to other promoters and inserted into the chromosome of *N. meningitidis* by homologous recombination.

Example 4

Modification of Poly-G Tract to Improve Bacterial Expression

The wild-type porA gene has a poly-G tract in its promoter that is variable within and between strains, and causes variable expression. To ensure consistent expression of PorA and variants, the poly-G tract was modified to reduce variation, as 11G is associated with optimal expression of PorA. To reduce changes in the PolyG tract, it may be modified such that it is replaced with $G_5AG_5$. This sequence is the same length as $G_{11}$, but will change in length less frequently than the $G_{11}$ homopolymeric tract. To this end, a sequence was synthesised encompassing approximately 330 nucleotides upstream of the porA, which modified region includes $G_5AG_5$ in place of the native poly-G tract. This sequence includes the nucleotides encoding the first 38 amino acids of PorA, and also incorporates part of the kanamycin resistance gene of pJJ260. This sequence was synthesised by DNA 2.0, cloned into a plasmid vector. This was excised with SphI and RsrII, and used to replace a SphI-RsrII fragment of pPorDel: SacB. The resultant plasmid, pPorDelSacFixG, was transformed into strain ¢9 of *N. meningitidis* (Virji et al., 1995, supra) resulting in strain ¢3-Fix. Such recipients may replace all or part of the porA promoter. ¢3-Fix (used for subsequent transformation) contains G11 in the promoter. Subsequent transformation with DNA encompassing recombinant porA results in replacement of the TetRSacBKan region with the variant porA allele. In this way, plasmid DNA, or PCR amplimers (amplified with primers PorAF1: 5' GTTCGGTCGTTTC- CGATAA-3' (SEQ ID NO:54) and OMWF 5'-GGGG-TATAATTGAAGACGTATCGG-3' (SEQ ID NO:92), or genomic DNA, with selection on media containing 10% sucrose allowed identification of strains with recombinant porA expression. Sequence analysis further identified the number of G residues in the promoter (see Table 5). It will be apparent that a recombinant porA gene can be transcriptionally linked to other promoters and inserted into the chromosome of N. meningitidis by homologous recombination. For example, the promoter of the porB gene from N. meningitidis and a promoter of the opa gene of Neisseria are amplified from genomic DNA of N. meningitidis or N. gonorrhoeae, and the amplimer used to replace the porA promoter in any of the plasmids described in Table 3 prior to transformation of the recombinant allele into N. meningitidis. For example, nucleotides 2157459-2157528 of accession AE002098.2 encompasses the promoter of the porB gene of N. meningitidis strain MC58(5'-TAAATGCAAAGCTAAGCGGCTTG-GAAAGCCCGGCCGGCTTAA ATTTCTTAAC-CAAAAAAGGAATACAGCA-3'; SEQ ID NO:93). Similarly, the promoter of opaA of N. gonorrhoeae strain MS11 can be amplified by PCR using primers as described by Belland at al. 1997, Mol Microbial. 23:123-35.

Example 5

Recombinant PorA Elicit Cross-Reactivity to Epitopes of Heterologous PorA

Outer membrane vesicles (OMV) containing PorA proteins of the invention can be prepared from N. meningitidis and administered as vaccine. There are many well known methods for preparation of OMV vaccines, and their preparation with or without adjuvant such as Aluminium salts, as described in Frasch et al. (2001), Outer Membrane Protein Vesicle Vaccines for Meningococcal Disease. *Meningococcal Vaccines: Methods and Protocols*. A. Pollard and M. Maiden, eds, Humana Press. 66: 81-107.

Briefly, OMV proteins were isolated by deoxycholate method and protein concentration assessed by BCA assay, before adsorption to Aluminium Hydroxide gel (Sigma). Groups of 10 BALB/c mice were injected with 0.1-10 µg total protein on days 0, 21 and 28, followed by harvest of blood from terminal exsanguination 14 days after the final administration of vaccine. Serum can be prepared from blood by methods well known. Briefly, blood was clotted at room temperature for 1-2 hours, and incubated at 4° C. overnight. Serum was harvested as supernatant after 10 minutes centrifugation at 10,000×g 5 minutes. at 4° C. Serum was diluted in PBS and used in Western immunoblot against sarkosyl-insoluble proteins of four strains and their isogenic ΔporA:: tet mutants. The secondary antibody was goat anti-mouse IgG alkaline-phosphatase conjugate (Sigma), and binding was detected clourimetrically using NBT/BCIP (Sigma). This indicated that serum from mice vaccinated with OMVs comprising an isolated protein from strain 1728-2 (expressing PorA with VR1 replaced with loop 7 and VR2 replaced with loop 8; SEQ ID NO:15) recognised PorA from all strains (see Table 5 and FIG. 5). The strains used (and their relevant PorA serosubtype) were MC58 (P1.7,16-2), BZ133 (P1.18-1,3), BZ232 (P1.5-2, 2-2) and 400 (P1.19,15).

Example 6

Recombinant PorA Proteins Elicit Cross-Reactivity to Surface Epitopes of Heterologous PorA by ELISA Bacteria from overnight culture on solid media (BHI agar) were subcultured for 4 hours before resuspending to A600 nm=0.1, heat killing (56° C. 30 minutes) before coating flat bottom 96 well plates (Nunc immunosorp). Sera were harvested from mice that had been vaccinated with 0.1-0.5 µg protein prepared as OMVs described in Example 5. Sera from vaccinated mice were tested for their ability to recognize bacterial cells in this assay. Secondary antibodies was goat anti-mouse immunoglobulins HRP conjugate (DAKO P 0447, raised against mouse immunoglobulins, mainly IgG). The reciprocal geometric mean titre reported in FIGS. 6A and 6B and Table 6 is the last dilution at which the reading was above negative control (defined as mean of negative control OD plus 3SD). In each case, sera were tested against parental strains (400, BZ133, and BZ232) and the respective isogenic PorA mutant strains. Surprisingly, OMV from strains 1728-2 (expressing PorA with VR1 replaced with loop 7 and VR2 replaced with loop 8; SEQ ID NO:15) and from strain D145 (expressing PorA with loops 1, 4, and 5 deleted; SEQ ID NO:5) elicited antibodies that recognized the three test strains with higher titres than the three test PorA mutant strains. Conversely, OMV from strains ¢9 (expressing PorA P1.7,16-2), strain 027-3 (expressing PorA of SEQ ID NO:13) and strain 028-10 (expressing PorA of SEQ ID NO:14) did not consistently elicit murine antibodies that recognized wild-type strains better than PorA mutant strains in this experiment.

Example 7

Bactericidal Assay to Assess Capacity of OMVs with Variant PorA to Target Autologous or Heterologous Strains This assay is performed by a modification of the method described by Hoogerhout et. al. 1995 Infection and Immunity 63: 3473-3478). Briefly, bacteria are grown overnight on BHI plates at 37° C. in 5% $CO_2$. Bacteria from this overnight culture are subcultured under the same conditions for 4-6 hours before suspension in 1 mL PBS. The bacterial suspension is adjusted to approximately $10^5$ cfu/mL in PBS. Sera to be tested are heat inactivated at 56° C. for 45 minutes. Baby rabbit complement is obtained from commercial supplier (e.g. PelFreez). The assay is carried out in sterile polystyrene flat-bottomed 96 well microtitre plate. The total volume in each well is 24 µL including: 12 µL of twofold serially diluted serum in PBS and 6 µL of bacterial suspension (containing between 300-900 bacteria). Sera and bacteria were incubated at room temperature for 10 minutes before addition of 6 µl., of 80% complement in PBS (final concentration 20% vol/vol). Controls are a) PBS, bacteria and complement, b) PBS, bacteria and serum. After addition of all components and mixing, a 7 µL aliquot from each control well is transferred to a Bill agar plate. The microtitre plate is incubated at 37° C. in 5% $CO_2$ for 60 minutes. After this incubation, a 7 µL aliquot from each well is transferred to BHI agar plates. All BHI plates are incubated for 14-18 hours at 37° C. in 5% $CO_2$ and bacterial colonies counted. Serum bactericidal killing is reported as the highest reciprocal dilution at which at least 90% of bacteria are killed. In each case, individual or pooled mouse sera are tested against MC58, MC58por::tet and against strains expressing heterologous PorA or their PorA mutants (MC58 PorA is P1.7, 16.2, whilst strains 2996 and M990 for example are P1.5,1,2-2 and P1.18,25 respectively; see FIG. 3A).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLE 1

Loop sequences of MC58 PorA (P1.7, 16, accession number AF226344). Bold indicates residues identical or conserved between serosubtypes. Extent of loops follows the precedent of the PorA model proposed by van der Ley et al., 1991, supra, or Derrick et al., 1999, supra.

| Loop | Sequence |
|---|---|
| 1 | VEGRNYQLQLTEAQAANGGASGQVKVTKVTKAKRKSRIRTKI (SEQ ID NO: 47) |
| 2 | VSV-GGGATQWGNR (SEQ ID NO: 48) |
| 3 | ASQAIDPWDSNNDVASQLGIFKRHDD (SEQ ID NO: 49) |
| 4 (VR2) | PIQNSKSAYTPAYYTKNTNNNLTLVPAVVGKPGS (SEQ ID NO: 50) |
| 5 (SVR1) | RHANVGRDAFELFLLGSGSDQAKGTDPLKNH (SEQ ID NO: 51) |
| 6 (SVR2) | LSENGDK-TKNSTTE (SEQ ID NO: 52) |
| 7 | FDLIERGKKGENTS (SEQ ID NO: 53) |
| 8 | KRNTGIGNYTQIN (SEQ ID NO: 54) |

TABLE 2

Expression constructs for bacterial expression of SEQ ID NOS: 1-10

| Plasmid | | | Primers used or method |
|---|---|---|---|
| pPorA | | | Plasmid containing porA allele identical to the reading frame of locus NMB1429 | PorAF1: 5' GTTCGGTCGTTTCCGATAA-3' (SEQ ID NO: 55) PorARev1: 5' TTTGAAACCCTGACCCTCTG-3' (SEQ ID NO: 56) |
| pPorDel | | porA gene deleted | porDELup 5'-TATACCCGGGTCG CAT ATC GGC TTC CTT TTG TAA ATT TGA-3' (SEQ ID NO: 57) porDELdown 5'-TCC GTC GGT TTG CGC CAC AAA TTC-3' (SEQ ID NO: 58) |
| pPorDel: LacZkan | | pPorDel with LacZkan inserted | LacZKan amplified using laczstuF: GTGAAAAGGCCTGATCCCGTCGTTTTACAA (SEQ ID NO: 59) lacStukanR: GTGAAAAGGCCTCAATTCTGATTAGAAAAACTC (SEQ ID NO: 60) digested with StuI and ligated into SmaI digested pPorDel |
| pPorDel: SacB | | pPorDel with TetR SacB KanR inserted | TetR-SacB-Kan excised from pJJ260 with SmaI and ligated into SmaI digested pPorDel |
| pPorDel: Tet | | pPorDel with TetS inserted | TetM gene excised from pGEMTetM-B with HincII and ligated to Sma I digested pPorDel |
| pPorDelSacFixG | | | Synthesized sequence incorporating G5AG5 cloned into SphI-RsrII site of pPorDel: SacB |
| pPorΔL1 | ΔLoop1 amino acids 38-63 deleted | | DEL_Loop1_up_5'-CTG GTA GTT CCT GCC TTC CACG-3' (SEQ ID NO: 61) DEL_Loop1_down 5'-AGC CAA GCC GCT AAC GGT GGA-3' (SEQ ID NO: 62) pPorA as template |
| pPorΔL4 | | ΔLoop4 amino acids 187-211 deleted | DEL_L4up 5'-GAT CGG AAC GAA TTG AAC GCT GC-3' (SEQ ID NO: 63) DEL_L4down 5'GTT GTC GGC AAG CCC GGA TC-3' (SEQ ID NO: 64) pPorA as template |
| pPorΔL1-4 | ΔLoop1 amino acids 38-63 deleted | ΔLoop4 amino acids 187-211 deleted | DEL_L4up DEL_L4down using pPorΔL1 as template |

TABLE 2-continued

Expression constructs for bacterial expression of SEQ ID NOS: 1-10

| Plasmid | | | | Primers used or method |
|---|---|---|---|---|
| pPorD145 | ΔLoop1 amino acids 38-63 deleted | ΔLoop4 amino acids 187-211 deleted | ΔLoop5 amino acids 248-268 deleted | DEL_L5_up_5'-TCC GAC ATT GGC GTG TCT CGC-3' (SEQ ID NO: 65) DEL_L5-down 5'-TTG AAA AAC CAT CAG GTA CAC CGT CTG-3' (SEQ ID NO: 66) pPorΔL1-4 as template |
| pDELVR1 | ΔVR1 amino acids 43-63 deleted | | | delVR1_up 5' TTC AGT CAA TTG CAG CTG GTA GTT CCT-3' (SEQ ID NO: 67) DEL_Loop1_down 5'-AGC CAA GCC GCT AAC GGT GGA-3' (SEQ ID NO: 68) pPorA as template |
| pDELVR2 | | ΔVR2 amino acids 197-209 deleted | | Synthesized region including deletion, used to replace BssHII-KpnI fragment encompassing VR2 region of pPorA |
| pDELVR1-2 | ΔVR1 amino acids 43-63 deleted | ΔVR2 amino acids 197-209 deleted | | Synthesized region including deletion, used to replace BssHII-KpnI fragment encompassing VR2 region of pDELVR1 |
| pDELVR1-2-5 | ΔVR1 amino acids 43-63 deleted | ΔVR2 amino acids 197-209 deleted | ΔLoop5 amino acids 248-268 deleted | DEL_L5_up_5'-TCC GAC ATT GGC GTG TCT CGC-3' (SEQ ID NO: 69) DEL_L5-down 5'-TTG AAA AAC CAT CAG GTA CAC CGT CTG-3' (SEQ ID NO: 70) pDELVR1-2 as template |
| pDELVR1-2-5-6 | ΔVR1 amino acids 43-63 deleted | ΔVR2 amino acids 197-209 deleted | ΔLoop5 amino acids 248-268 deleted | Also has amino acids 298-306 of loop 6 deleted, DEL_L6_up 5'AGA CAA ATC CAA CTG AGC CGC CAA (SEQ ID NO: 71) DEL_L6_down 5'AGT ACG ACC GAA ATT GCC GCC ACT-3' (SEQ ID NO: 72) Using pDELVR1-2-5 as template |

TABLE 3

Expression constructs for bacterial expression of SEQ ID NOS: 11-19

| Plasmid name | VR1 | VR2 | Primers used |
|---|---|---|---|
| pVR2-7 | WT | aa 197-209 replaced with aa 331-344 | Loop4-7up 5' ACC GCG TTC GAT AAA GTC GAA AGC CGG CGT ATA GGC GGA CTT-3' (SEQ ID NO: 73) Loop4-7down_5'-AAA AAA GGC GAA AAT ACC AGC CCG GCT GTT GTC GGC AAG C-3' (SEQ ID NO: 74) pPorA as PCR template |
| pVR2-8 | WT | aa 197-209 replaced with aa 370-382 | Loop4-8up 5' GCC GGT ATT GCG TTT AGC CGG CGT ATA GGC GGA CTT (SEQ ID NO: 75) Loop4-8down 5'-ATC GGC AAC TAC ACT CAA ATT AAT CCG GCT GTT GTC GGC AAG C-3' (SEQ ID NO: 76 pPorA as template |
| pΔVR1VR2-7 | ΔVR1 amino acids 43-63 deleted | aa 197-209 replaced with aa 331-344 | Primers used: delVR1_up, DEL_Loop1_down pVR2-7 as template |
| pΔVR1VR2-8 | ΔVR1 amino acids 43-63 deleted | aa 197-209 replaced with aa 370-382 | Primers used: delVR1_up, DEL_Loop1_down pVR2-8 as template |
| pVR1-7VR2-8 | aa 43-63 replaced with aa 331-344 | aa 197-209 replaced with aa 370-382 | Loop1-7up_5' ACC GCG TTC GAT AAA GTC GAA TTC AGT CAA TTG CAG CTG GTA GGT CCT-3' (SEQ ID NO: 77) Loop1-7down 5'-AAA AAA GGC GAA AAT ACC AGC AGC CAA GCC GCT AAC GGT GGA-3' (SEQ ID NO: 78) pVR2-8 as template |

TABLE 3-continued

Expression constructs for bacterial expression of SEQ ID NOS: 11-19

| Plasmid name | VR1 | VR2 | Primers used |
|---|---|---|---|
| pVR1-7VR2-8Del5 | aa 43-63 replaced with aa 331-344 | aa 197-209 replaced with aa 370-382 | ΔLoop5<br>amino acids 248-268 deleted using primers<br>DEL_L5_up_5'-TCC GAC ATT GGC GTG TCT CGC-3' (SEQ ID NO: 79)<br>DEL_L5-down 5'-TTG AAA AAC CAT CAG GTA CAC CGT CTG-3' (SEQ ID NO: 80) |
| pPor7in1 | Loop7 into VR1: aa 331-344 inserted into VR1 | | 7into1up: 5' ACC GCG TTC GAT AAA GTC GAA CGC TCC ACC GTT AGC GGC TTG TGC-3' (SEQ ID NO: 81)<br>7into1down: 5'-5'-AAA AAA GGC GAA AAT ACC AGC AGC GGT CAG GTA AAA GTT ACT AAA GTT ACT AAG-3'-3' (SEQ ID NO: 82)<br>pPorA as template |
| pPor8in4 | Loop7 into VR1: aa 331-344 inserted into VR1 | Loop 8 inserted into VR2: aa 370-382 inserted into VR2 | 8into4up: 5' GCC GGT ATT GCG TTT GTT TGT ATT CTT AGT ATA ATA AGC-3' (SEQ ID NO: 83)<br>8into4down: 5'-ATC GGC AAC TAC ACT CAA ATT AAT AAC AAT CTT ACT CTC GTT CCG GCT GTT-3' (SEQ ID NO: 84)<br>pPorA as template |
| pPor7in1-8in4 | Loop7 into VR1: aa 331-344 inserted into VR1 | Loop 8 inserted into VR2: aa 370-382 inserted into VR2 | Primers: 8into4up & 8into4down<br>pPor7in1 as template |

TABLE 4

Derivation of *N. meningitidis* recombinant strains

| Donor Allele/ recipient strain | Plasmid/PCR/genomic | Resulting *N. meningitidis* clone |
|---|---|---|
| PorDel:Tet | pPorDel:Tet into ¢9 | 9ΔPorTa |
| PorDel:LacZkan | pPorDel:LacZkan into ¢9 | ¢2ΔPorlacZkan |
| PorDel:LacZkan | gDNA of ¢2ΔPorlacZkan into cut9ΔPorTa | ¢9ΔPorlac |
| PorDel: SacB | pPorSacB into MC58 | 58PorSac1 |
| PorSacB | gDNA of 58PorSac1 into ¢9ΔPorlac | ¢9delPorASacb |
| PorDelSacFixG | pPorDelSacFixG into ¢3 | ¢3Fix3A |
| PorA:SacB Kan 11G | gDNA from ¢3Fix3A into ¢9 | 9-Fix |

TABLE 5

*N. meningitidis* recombinant strains used for vaccine studies

| Allele | Plasmid/PCR/genomic DONOR DNA into recipient strain: | Resulting *N. meningitidis* Clone (comment) |
|---|---|---|
| PorDel:Tet | pPorDel:Tet into ¢9 | 9ΔPorTa |
| WT porA | pPorA into 9-Fix | 9-5, (11G in promoter) |
| WT porA | pPorA into 9-Fix | 9-1, (10G in promoter) |
| 1728 | pVR1-7VR2-8 into 9-Fix | 1728-2, (11G in promoter) |
| 0-27 | PCR product of pΔVR1 VR2-7 (Primers OMWF and AR1) into 9-Fix | 027-3 (11G in promoter) |
| 0-28 | PCR product of pΔVR1 VR2-8 (Primers OMWF and AR1) into 9-Fix | 028-10 (11G in promoter) |
| ΔL1ΔL4ΔL5 | PCR product of pΔL1ΔL4ΔL5 (Primers OMWF and AR1) into 9-Fix | 145-5 (11G in promoter) |

TABLE 6

Tabulated data from of Experiment 2 of Example 6. Pooled sera from 10 mice vaccinated with 0.1-0.5 μg dexoycholate OMV were used as primary antibody in serial two fold dilutions against heat killed bacteria of the strains listed ("Strains tested") in an ELISA assay. In this table, P- denotes strain with porA gene disrupted.

| Strain | Immunogen: | | | | | |
|---|---|---|---|---|---|---|
| tested | ¢9 | ¢9 P- | 1728-2 | D145 | 027-3 | 028-10 |
| 400 | 16000 | 32000 | 406375 | 256000 | 3177 | 15996 |
| 400P- | 12699 | 64000 | 40317 | 64000 | 7998 | 31989 |
| BZ133 | 8000 | 64000 | 203187 | 128000 | 5035 | 50816 |
| BZ133P- | 8000 | 64000 | 50797 | 64000 | 7998 | 15996 |
| BZ232 | 6350 | 32000 | 161270 | 80635 | 12706 | 15996 |
| BZ232P- | 6350 | 40317 | 64000 | 40317 | 50816 | 40272 |

TABLE 7

Summary of protein constructs.

| Construct | SEQ ID NOS |
|---|---|
| Deletions of V regions only | 2-10 |
| Deletions of V region replaced by conserved loops | 11-16 and 20-22 |
| Insertion of conserved loops into V regions | 17-19 |

The invention claimed is:

1. An isolated protein comprising the amino acid sequence of a PorA protein of *Neisseria meningitides*, wherein:
   one or more variable regions of the PorA protein are disrupted by replacing the one or more variable regions or a plurality of contiguous amino acids of the one or more variable regions with one or more entire PorA conserved regions, or at least six (6) contiguous conserved region amino acids of the one or more entire PorA conserved regions;

the one or more variable regions are selected from the group consisting of: variable region 1 (VR1), variable region 2 (VR2), a semi-variable region 1 (SVR1), and semi-variable region 2 (SVR2); and the PorA conserved region is selected from the group consisting of loop 2, loop 3, loop 7, and loop 8 amino acid sequences.

2. The isolated protein of claim 1, wherein the one or more variable regions are selected from the group consisting of: a VR1 region; and a VR2 region.

3. The isolated protein of claim 1, wherein the one or more variable regions are absent.

4. The isolated protein of claim 1, wherein the one or more variable regions are replaced by one or more entire loop 8 PorA conserved regions, or at least six (6) loop 8 conserved region amino acids.

5. The isolated protein of claim 1, comprising the amino acid sequence set forth in SEQ ID NO:14.

6. An isolated protein which is a variant of the isolated protein of claim 1 comprising at least 95% sequence identity to SEQ ID NO:14, and wherein the isolated protein is not a wild-type PorA protein.

7. An Outer Membrane Protein Vesicle (OMV) comprising the isolated protein of claim 1.

8. A pharmaceutical composition comprising: an isolated protein according to claim 1 and a pharmaceutically acceptable carrier, diluent, or excipient.

9. The pharmaceutical composition of claim 8 comprising the isolated protein in an Outer Membrane Protein Vesicle (OMV).

10. The pharmaceutical composition of claim 8, wherein the isolated protein is present as a recombinant protein expressed in a host cell.

11. The pharmaceutical composition of claim 10, wherein the host cell is a bacterium.

12. The composition of claim 10, wherein the host cell is *Neisseria meningitidis*.

13. A method of treating an *N. meningitidis* infection in a human, the method comprising administering an isolated protein according to claim 1 to the human to thereby treat the *N. meningitidis* infection in the human.

14. The method of claim 13, wherein the isolated protein is in an Outer Membrane Protein Vesicle (OMV).

15. The method of claim 13, wherein the isolated protein is present as a recombinant protein expressed in a host cell.

16. The method of claim 15, wherein the host cell is a bacterium.

17. The method of claim 15, wherein the host cell is *Neisseria meningitidis*.

* * * * *